(12) United States Patent
Marraffini et al.

(10) Patent No.: US 11,299,732 B2
(45) Date of Patent: Apr. 12, 2022

(54) COMPOSITIONS AND METHODS FOR TRANSCRIPTION-BASED CRISPR-CAS DNA EDITING

(71) Applicant: THE ROCKEFELLER UNIVERSITY, New York, NY (US)

(72) Inventors: Luciano Marraffini, New York, NY (US); Gregory Goldberg, New York, NY (US); Poulami Samai, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 15/501,640

(22) PCT Filed: Aug. 7, 2015

(86) PCT No.: PCT/US2015/044236
§ 371 (c)(1),
(2) Date: Feb. 3, 2017

(87) PCT Pub. No.: WO2016/022931
PCT Pub. Date: Feb. 11, 2016

(65) Prior Publication Data
US 2017/0233729 A1    Aug. 17, 2017

Related U.S. Application Data

(60) Provisional application No. 62/034,684, filed on Aug. 7, 2014.

(51) Int. Cl.
*C12N 15/11* (2006.01)
*C12N 15/10* (2006.01)
*C12N 15/63* (2006.01)
*C12N 9/22* (2006.01)
*C12N 15/52* (2006.01)

(52) U.S. Cl.
CPC ............... *C12N 15/11* (2013.01); *C12N 9/22* (2013.01); *C12N 15/102* (2013.01); *C12N 15/52* (2013.01); *C12N 15/63* (2013.01); *C12N 2310/20* (2017.05)

(58) Field of Classification Search
None
See application file for complete search history.

(56) References Cited

U.S. PATENT DOCUMENTS 8,697,359 B1 * 4/2014 Zhang ............... C12N 15/85
435/6.1
2014/0186958 A1    7/2014 Zhang et al.

OTHER PUBLICATIONS

Hatoum-Aslan et al., PNAS, 2011, vol. 102, No. 52, pp. 21218-21222.*
Hatoum-Aslan et al., PNAS, 2011, vol. 108 pp. 21218-21222.*
Gasiunas et al., PNAS, 2012, E2579-E2586.*
Waldrip et al., "A CRISPR-based approach for proteomic analysis of a single genomic locus" 9(9) Epigenetics 1207-1211 (Jul. 18, 2014) (Year: 2014).*
Hatoum-Aslan, A., et al., A Ruler Protein in a Complex for Antiviral Defense Determines the Length of Small Interfering CRISPR RNAs., Journal of Biological Chemistry, Aug. 9, 2013, vol. 288, No. 39, pp. 27888-27897.
Samai, P., et al., Co-transcriptional DNA and RNA Cleavage during Type III CRISPR-Cas Immunity, Cell, May 7, 2015, vol. 161, pp. 1164-1174.
Hatoum-Aslan, A., et al., Genetic Characterization of Antiplasmid Immunity Through a Type III-A CRISPR-Cas system, Journal of Bacteriology, Nov. 1, 2013, vol. 196, No. 2, pp. 310-317.
Hrle, A., et al. Structure and RNA-binding properties of the Type 111-A CRISPR-associated protein Csm3, RNA Biology, Sep. 30, 2013, vol. 10, No. 11, pp. 1670-1678.
Marraffini. L.A., et al., Self vs. non-self discrimination during CRISPR RNA-directed immunity, Nature, Jan. 13, 2010, vol. 463, pp. 568-571.
Horinouchi, S., et al. Nucleotide Sequence and Functional Map of pC194, a Plasmid That Specifies Inducible Chloramphenicol Resistance, Journal of Bacteriology, May 1982, vol. 150, No. 2, pp. 815-825.

* cited by examiner

*Primary Examiner* — Nancy J Leith
(74) *Attorney, Agent, or Firm* — Hodgson Russ LLP

(57) ABSTRACT

Provided are compositions and methods for cleaving a DNA sequence in a cell. The methods involve comprising introducing into a cell a recombinant vector containing a clustered regularly interspaced short palindromic repeats (CRISPR) system. The system includes a CRISPR RNA (crRNA) targeted to a DNA sequence in the cell that is operatively linked to a promoter; and CRISPR-associated enzymes (Cas) 10, Cas6, and at least one Csm protein. The Cas 10 cleaves the DNA sequence only during transcription of the DNA sequence that is operatively linked to the promoter. Also provided are recombinant vectors for modifying cells, cells that contain the recombinant vectors and modifications introduced by them, and kits that include the modified vectors.

7 Claims, 23 Drawing Sheets

Specification includes a Sequence Listing.

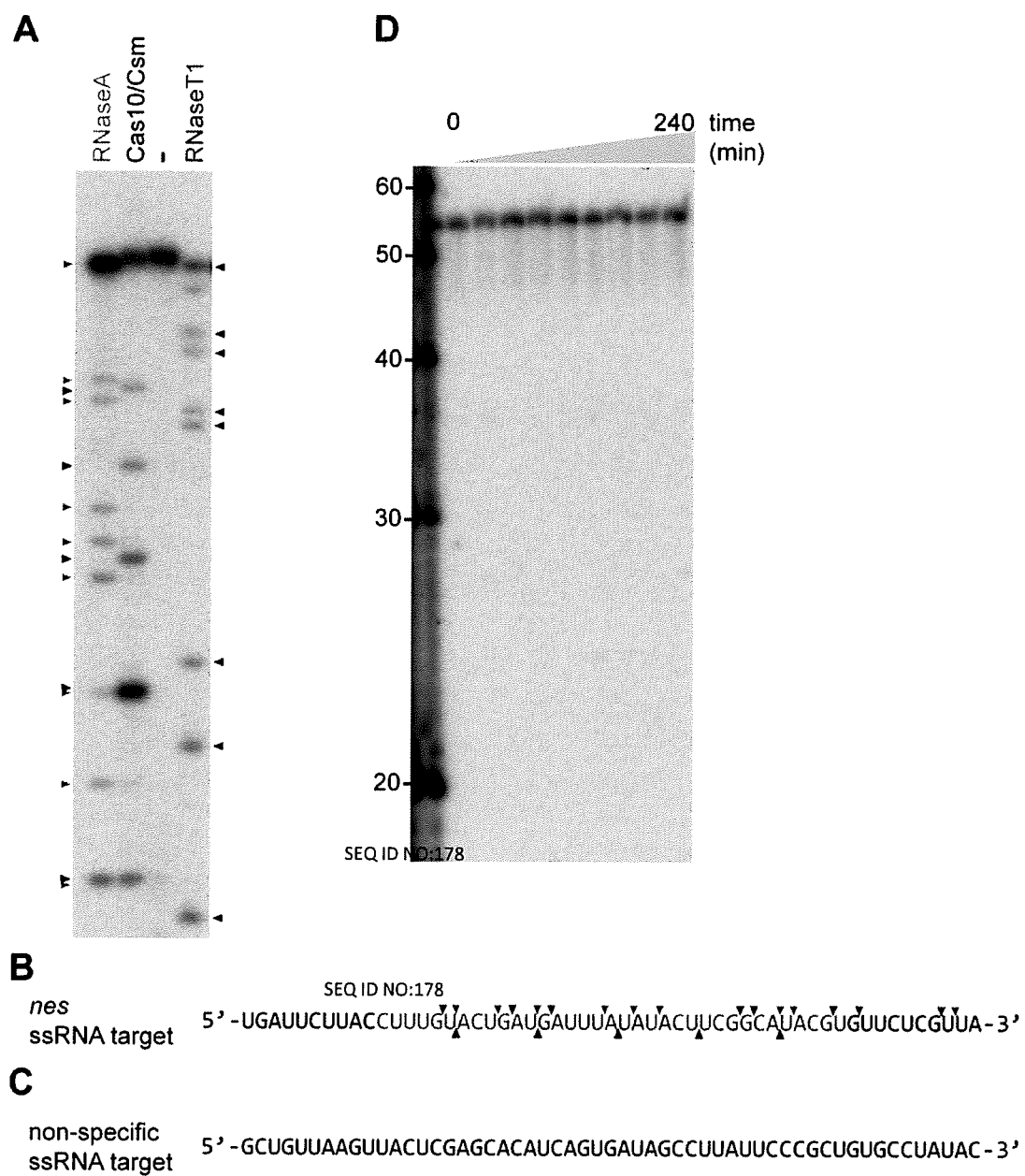

SEQUENCE LISTING

<160> NUMBER OF SEQ ID NOS: 192

<210> SEQ ID NO 1
<211> LENGTH: 4627
<212> TYPE: DNA
<213> ORGANISM: artificial sequence
<220> FEATURE:
<223> OTHER INFORMATION: Plasmid

<400> SEQUENCE: 1

```
ctctgtaact gcttatttgc cttctgtaac tcatccttaa cttcttgcag ttcctgttta      60
tgaaatacag tatctttctt gtactgatcc atcgctttat gttctcgttc tgtaacctct     120
ttggacgtgc ctctttcaag ttcataacct ttctcattca catactcatt aaatctatct     180
tgtaattgag taaagtcttt cttgttgcct aactgttctt ttgcagacaa tctcccgtcc     240
tctgttaaag ggacaaaacc aaagtgcata tgtgggactc tttcatccag atggacagtc     300
gcatacagca tattttcctt accgtattca ttttctagaa actccaagct atctttaaaa     360
aatcgttcta tttcttctcc gcttaaatca tcaaagaaat ctttatcact tgtaaccagt     420
ccgtccacat gtcgaattgc atctgaccga attttacgtt tccctgaata attctcatca     480
```

```
atcgtttcat caattttatc tttatacttt atattttgtg cgttaatcaa atcataattt    540
ttatatgttt cctcatgatt tatgtcttta ttattatagt ttttattctc tctttgatta    600
tgtctttgta tcccgtttgt attacttgat cctttaactc tggcaaccct caaaattgaa    660
tgagacatgc tacacctccg gataataaat atatataaac gtatatagat ttcataaagt    720
ctaacacact agacttattt acttcgtaat taagtcgtta aaccgtgtgc tctacgacca    780
aaactataaa acctttaaga actttctttt tttacaagaa aaaagaaatt agataaatct    840
ctcatatctt ttattcaata atcgcatccg attgcagtat aaatttaacg atcactcgtt    900
accatcacgg aaaaaggtta tgctgctttt aagacccact ttcacattta agttgttttt    960
ctaatccgca tatgatcaat tcaaggccga ataagaaggc tggctctgca ccttggtgat   1020
caaataattc gatagcttgt cgtaataatg gcggcatact atcagtagta ggtgtttccc   1080
tttcttcttt agcgacttga tgctcttgat cttccaatac gcaacctaaa gtaaaatgcc   1140
ccacagcgct gagtgcatat aatgcattct ctagtgaaaa accttgttgg cataaaaagg   1200
ctaattgatt ttcgagagtt tcatactgtt tttctgtagg ccgtgtacct aaatgtactt   1260
ttgctccatc gcgatgactt agtaaagcac atctaaaact tttagcgtta ttacgtaaaa   1320
aatcttgcca gctttccccT tctaaagggc aaaagtgagt atggtgccta tctaacatct   1380
caatggctaa ggcgtcgagc aaagcccgct tattttttac atgccaatac aatgtaggct   1440
gctctacacc tagcttctgg gcgagtttac ggggttgttaa accttcgatt ccgacctcat   1500
taagcagctc taatgcgctg ttaatcactt tacttttatc taatctagac atcattaatt   1560
cctccttttt gttgacatta tatcattgat agagttattt gtcaaactag ttttttattt   1620
ggatcccctc gagttcatga aaaactaaaa aaaatattga cactctatca ttgatagagc   1680
ataattaaaa taagctctct atcattgata gagtgatatc cggaggcata tcaaatgacc   1740
taggagatct gtgattctta cctttgtact gatgatttat atacttcggc atacgttctc   1800
taaatatctt gttcatattt atcagagctc gtgctataat tatactaatt ttataaggag   1860
gaaaaaatat gggcattttt agtatttttg taatcagcac agttcattat caaccaaaca   1920
aaaaataagt ggttataatg aatcgttaat aagcaaaatt catataacca aattaaagag   1980
ggttataatg aacgagaaaa atataaaaca cagtcaaaac tttattactt caaaacataa   2040
tatagataaa ataatgacaa atataagatt aaatgaacat gataatatct ttgaaatcgg   2100
ctcaggaaaa ggccatttta cccttgaatt agtaaagagg tgtaatttcg taactgccat   2160
tgaaatagac cataaattat gcaaaactac agaaaataaa cttgttgatc acgataattt   2220
ccaagtttta aacaaggata tattgcagtt taaatttcct aaaaaccaat cctataaaat   2280
atatggtaat ataccttata acataagtac ggatataata cgcaaaattg tttttgatag   2340
tatagctaat gagatttatt taatcgtgga atacggtttt gctaaaagat tattaaatac   2400
aaaacgctca ttggcattac ttttaatggc agaagttgat atttctatat taagtatggt   2460
tccaagagaa tattttcatc ctaaacctaa agtgaatagc tcacttatca gattaagtag   2520
aaaaaaatca agaatatcac acaaagataa acaaagtat aattatttcg ttatgaaatg    2580
ggttaacaaa gaatacaaga aaatatttac aaaaaatcaa tttaacaatt ccttaaaaca   2640
tgcaggaatt gacgatttaa acaatattag ctttgaacaa ttcttatctc ttttcaatag   2700 ctataaaatta tttaataagt aagttaaggg atgcataaac tgcatcccctt aacttgtttt   2760 tcgtgtgcct atttttgtg aatcgattat gtcttttgcg cagtcggctt aaaccagttt   2820
tcgctggtgc gaaaaaagag tgtcttgtga cacctaaatt caaaatctat cggtcagatt   2880
```

```
tataccgatt tgattttata tattcttgaa taacatacgc cgagttatca cataaaagcg    2940
ggaaccaatc atcaaattta aacttcattg cataatccat taaactctta aattctacga    3000
ttccttgttc atcaataaac tcaatcattt ctttaattaa tttatatcta tctgttgttg    3060
ttttctttaa taattcatca acatctacac cgccataaac tatcatatct tcttttttgat   3120 atttaaattt attaggatcg tccatgtgaa gcatatatct cacaagacct ttcacacttc    3180
ctgcaatctg cggaatagtc gcattcaatt cttctgttaa ttattttat ctgttcataa     3240 gatttattac cctcatacat cactagaata tgataatgct ctttttcat cctaccttct     3300 gtatcagtat ccctatcatg taatggagac actacaaatt gaatgtgtaa ctcttttaaa    3360
tactctaacc actcggcttt tgctgattct ggatataaaa caaatgtcca attacgtcct    3420
cttgaatttt tcttgttttc agtttctttt attacatttt cgctcatgat ataataacgg    3480
tgctaataca cttaacaaaa tttagtcata gataggcagc atgccagtgc tgtctatctt    3540
tttttgttta aaatgcaccg tattcctcct ttgcatattt ttttattaga ataccggttg    3600
catctgattt gctaatatta tatttttctt tgattctatt taatatctca ttttcttctg    3660
ttgtaagtct taaagtaaca gcaacttttt tctcttcttt tctatctaca accatcactg    3720
tacctcccaa catctgtttt tttcacttta acataaaaaa caaccttta acattaaaaa     3780 cccaatattt atttatttgt ttggacaatg gacaatggac acctagggg gaggtcgtag     3840 taccccccta tgttttctcc cctaaataac cccaaaaatc taagaaaaaa agacctcaaa    3900
aaggtcttta attaacatct caaatttcgc atttattcca atttccttt tgcgtgtgat     3960 gcgctgcgtc cattaaaaat cctagagctt tgcaaccgaa agttaatagc tgtcgctact    4020
actttcgctt acgctctaag tatattttaa ggactgtcac acgcaaaaag ttttctcggc    4080
ataaaagtac ctctacatct ctaaatcgtc tgtacgctgt ttctcacgct ttctatcgac    4140
cttctggaca ttatcctgta caacatccat aaactgtccc acacgctcaa atttggaatc    4200
attaaagaat ttctctttaa gcctattaaa ccctttctca aacccaggga aattcgccct    4260
cgcagcacga tataaagtca ctgtactagc ttgaaatttc tctgatacat tcaactgctc    4320
attcaaacta tcattctctc gctttaattt attaacctct ttactttttt cgtgataccc    4380
ctctttccat gtattcacta cttctttcaa actctctcta cgtttttta attcttgatt    4440 ttctgtgtaa tagtctgtgc tcttaatatt ttcgtaatca tcaacaatcc gttctgcaga    4500
agagattgtt tcttgcaggc gttcaaattc atcagcagtt aatatctttc taccagtctc    4560
ttcacgtcca gagaacaaac ctgtacgctc attttcataa tcaagggtt tcgtagacct    4620 catatgc                                                              4627
```

<210> SEQ ID NO 2
<211> LENGTH: 757
<212> TYPE: PRT
<213> ORGANISM: artificial sequence
<220> FEATURE:
<223> OTHER INFORMATION: CRISPR associated enzyme

<400> SEQUENCE: 2

Met Asn Lys Lys Asn Ile Leu Met Tyr Gly Ser Leu Leu His Asp Ile
1               5                   10                  15

Gly Lys Ile Ile Tyr Arg Ser Gly Asp His Thr Phe Ser Arg Gly Thr
            20                  25                  30

His Ser Lys Leu Gly His Gln Phe Leu Ser Gln Phe Ser Glu Phe Lys
        35                  40                  45

-continued

```
Asp Asn Glu Val Leu Asp Asn Val Ala Tyr His His Tyr Lys Glu Leu
        50                  55                  60
Ala Lys Ala Asn Leu Asp Asn Asp Asn Thr Ala Tyr Ile Thr Tyr Ile
 65                  70                  75                  80
Ala Asp Asn Ile Ala Ser Gly Ile Asp Arg Arg Asp Ile Ile Glu Glu
                 85                  90                  95
Gly Asp Glu Glu Tyr Glu Lys Gln Leu Phe Asn Phe Asp Lys Tyr Thr
                100                 105                 110
Pro Leu Tyr Ser Val Phe Asn Ile Val Asn Ser Glu Lys Leu Lys Gln
            115                 120                 125
Thr Asn Gly Lys Phe Lys Phe Ser Asn Glu Ser Asn Ile Glu Tyr Pro
        130                 135                 140
Lys Thr Glu Asn Ile Gln Tyr Ser Ser Gly Asn Tyr Thr Thr Leu Met
145                 150                 155                 160
Lys Asp Met Ser His Asp Leu Glu His Lys Leu Ser Ile Lys Glu Gly
                165                 170                 175
Thr Phe Pro Ser Leu Leu Gln Trp Thr Glu Ser Leu Trp Gln Tyr Val
                180                 185                 190
Pro Ser Ser Thr Asn Lys Asn Gln Leu Ile Asp Ile Ser Leu Tyr Asp
            195                 200                 205
His Ser Arg Ile Thr Cys Ala Ile Ala Ser Cys Ile Phe Asp Tyr Leu
        210                 215                 220
Asn Glu Asn Asn Ile His Asn Tyr Lys Asp Glu Leu Phe Ser Lys Tyr
225                 230                 235                 240
Glu Asn Thr Lys Ser Phe Tyr Gln Lys Glu Ala Phe Leu Leu Leu Ser
                245                 250                 255
Met Asp Met Ser Gly Ile Gln Asp Phe Ile Tyr Asn Ile Ser Gly Ser
                260                 265                 270
Lys Ala Leu Lys Ser Leu Arg Ser Arg Ser Phe Tyr Leu Glu Leu Met
            275                 280                 285
Leu Glu Val Ile Val Asp Gln Leu Leu Glu Arg Leu Glu Leu Ala Arg
        290                 295                 300
Ala Asn Leu Leu Tyr Thr Gly Gly His Ala Tyr Leu Leu Val Ser
305                 310                 315                 320
Asn Thr Asp Lys Val Lys Lys Ile Thr Gln Phe Asn Asn Glu Leu
                325                 330                 335
Lys Lys Trp Phe Met Ser Glu Phe Thr Thr Asp Leu Ser Leu Ser Met
            340                 345                 350
Ala Phe Glu Lys Cys Ser Gly Asp Asp Leu Met Asn Thr Ser Gly Asn
        355                 360                 365
Tyr Arg Thr Ile Trp Arg Asn Val Ser Ser Lys Leu Ser Asp Ile Lys
        370                 375                 380
Ala His Lys Tyr Ser Ala Glu Asp Ile Leu Lys Leu Asn His Phe His
385                 390                 395                 400
Ser Tyr Gly Asp Arg Glu Cys Lys Glu Cys Leu Arg Ser Asp Ile Asp
                405                 410                 415
Ile Asn Asp Asp Gly Leu Cys Ser Ile Cys Glu Gly Ile Ile Asn Ile
                420                 425                 430
Ser Asn Asp Leu Arg Asp Lys Ser Phe Phe Val Leu Ser Glu Thr Gly
            435                 440                 445
Lys Leu Lys Met Pro Phe Asn Lys Phe Ile Ser Val Ile Asp Tyr Glu
450                 455                 460
```

```
Glu Ala Glu Met Leu Val Gln Asn Asn Asn Gln Val Arg Ile Tyr Ser
465                 470                 475                 480

Lys Asn Lys Pro Tyr Ile Gly Ile Gly Ile Ser Thr Asn Leu Trp Met
            485                 490                 495

Cys Asp Tyr Asp Tyr Ala Ser Gln Asn Gln Asp Met Arg Glu Lys Gly
                500                 505                 510

Ile Gly Ser Tyr Val Asp Arg Glu Glu Gly Val Lys Arg Leu Gly Val
            515                 520                 525

Val Arg Ala Asp Ile Asp Asn Leu Gly Ala Thr Phe Ile Ser Gly Ile
530                 535                 540

Pro Glu Lys Tyr Asn Ser Ile Ser Arg Thr Ala Thr Leu Ser Arg Gln
545                 550                 555                 560

Leu Ser Leu Phe Phe Lys Tyr Glu Leu Asn His Leu Leu Glu Asn Tyr
                565                 570                 575

Gln Ile Thr Ala Ile Tyr Ser Gly Gly Asp Asp Leu Phe Leu Ile Gly
                580                 585                 590

Ala Trp Asp Asp Ile Ile Glu Ala Ser Ile Tyr Ile Asn Asp Lys Phe
                595                 600                 605

Lys Glu Phe Thr Leu Asp Lys Leu Thr Leu Ser Ala Gly Val Gly Met
610                 615                 620

Phe Ser Gly Lys Tyr Pro Val Ser Lys Met Ala Phe Glu Thr Gly Arg
625                 630                 635                 640

Leu Glu Glu Ala Ala Lys Thr Gly Glu Lys Asn Gln Ile Ser Leu Trp
                645                 650                 655

Leu Gln Glu Lys Val Tyr Asn Trp Asp Glu Phe Lys Lys Asn Ile Leu
                660                 665                 670

Glu Glu Lys Leu Leu Val Leu Gln Gln Gly Phe Ser Gln Thr Asp Glu
                675                 680                 685

His Gly Lys Ala Phe Ile Tyr Lys Met Leu Ala Leu Leu Arg Asn Asn
                690                 695                 700

Glu Ala Ile Asn Ile Ala Arg Leu Ala Tyr Leu Leu Ala Arg Ser Lys
705                 710                 715                 720

Met Asn Glu Asp Phe Thr Ser Lys Ile Phe Asn Trp Ala Gln Asn Asp
                725                 730                 735

Lys Asp Lys Asn Gln Leu Ile Thr Ala Leu Glu Tyr Tyr Ile Tyr Gln
                740                 745                 750

Ile Arg Glu Ala Asp
            755

<210> SEQ ID NO 3
<211> LENGTH: 141
<212> TYPE: PRT
<213> ORGANISM: artificial sequence
<220> FEATURE:
<223> OTHER INFORMATION: CRISPR associated enzyme

<400> SEQUENCE: 3

Met Ile Leu Ala Lys Thr Lys Ser Gly Lys Thr Ile Asp Leu Thr Phe
1               5                   10                  15

Ala His Glu Val Val Lys Ser Asn Val Lys Asn Val Lys Asp Arg Lys
            20                  25                  30

Gly Lys Glu Lys Gln Val Leu Phe Asn Gly Leu Thr Thr Ser Lys Leu
        35                  40                  45

Arg Asn Leu Met Glu Gln Val Asn Arg Leu Tyr Thr Ile Ala Phe Asn
50                  55                  60
```

```
Ser Asn Glu Asp Gln Leu Asn Glu Glu Phe Ile Asp Glu Leu Glu Tyr
 65                  70                  75                  80

Leu Lys Ile Lys Phe Tyr Tyr Glu Ala Gly Arg Glu Lys Ser Val Asp
                 85                  90                  95

Glu Phe Leu Lys Lys Thr Leu Met Phe Pro Ile Ile Asp Arg Val Ile
            100                 105                 110

Lys Lys Glu Ser Lys Lys Phe Phe Leu Asp Tyr Cys Lys Tyr Phe Glu
        115                 120                 125

Ala Leu Val Ala Tyr Ala Lys Tyr Tyr Gln Lys Glu Asp
    130                 135                 140
```

<210> SEQ ID NO 4
<211> LENGTH: 214
<212> TYPE: PRT
<213> ORGANISM: artificial sequence
<220> FEATURE:
<223> OTHER INFORMATION: CRISPR-associated enzyme

<400> SEQUENCE: 4

```
Met Tyr Ser Lys Ile Lys Ile Ser Gly Thr Ile Glu Val Val Thr Gly
  1               5                  10                  15

Leu His Ile Gly Gly Gly Gly Glu Ser Ser Met Ile Gly Ala Ile Asp
             20                  25                  30

Ser Pro Val Val Arg Asp Leu Gln Thr Lys Leu Pro Ile Ile Pro Gly
         35                  40                  45

Ser Ser Ile Lys Gly Lys Met Arg Asn Leu Leu Ala Lys His Phe Gly
 50                  55                  60

Leu Lys Met Lys Gln Glu Ser His Asn Gln Asp Glu Arg Val Leu
 65                  70                  75                  80

Arg Leu Phe Gly Ser Ser Glu Lys Gly Asn Ile Gln Arg Ala Arg Leu
                 85                  90                  95

Gln Ile Ser Asp Ala Phe Phe Ser Glu Lys Thr Lys Glu His Phe Ala
            100                 105                 110

Gln Asn Asp Ile Ala Tyr Thr Glu Thr Lys Phe Glu Asn Thr Ile Asn
        115                 120                 125

Arg Leu Thr Ala Val Ala Asn Pro Arg Gln Ile Glu Arg Val Thr Arg
    130                 135                 140

Gly Ser Glu Phe Asp Phe Val Phe Ile Tyr Asn Val Asp Glu Glu Ser
145                 150                 155                 160

Gln Val Glu Asp Asp Phe Glu Asn Ile Glu Lys Ala Ile His Leu Leu
                165                 170                 175

Glu Asn Asp Tyr Leu Gly Gly Gly Thr Arg Gly Asn Gly Arg Ile
            180                 185                 190

Gln Phe Lys Asp Thr Asn Ile Glu Thr Val Val Gly Tyr Asp Ser
        195                 200                 205

Thr Asn Leu Lys Ile Lys
    210
```

<210> SEQ ID NO 5
<211> LENGTH: 304
<212> TYPE: PRT
<213> ORGANISM: artificial sequence
<220> FEATURE:
<223> OTHER INFORMATION: CRISPR-associated enzyme

<400> SEQUENCE: 5

```
Met Thr Leu Ala Thr Lys Val Phe Lys Leu Ser Phe Lys Thr Pro Val
  1               5                  10                  15
```

His Phe Gly Lys Lys Arg Leu Ser Asp Gly Glu Met Thr Ile Thr Ala
            20                  25                  30

Asp Thr Leu Phe Ser Ala Leu Phe Ile Glu Thr Leu Gln Leu Gly Lys
        35                  40                  45

Asp Thr Asp Trp Leu Leu Asn Asp Leu Ile Ile Ser Asp Thr Phe Pro
    50                  55                  60

Tyr Glu Asn Glu Leu Tyr Tyr Leu Pro Lys Pro Leu Ile Lys Ile Asp
65                  70                  75                  80

Ser Lys Glu Glu Asp Asn His Lys Ala Phe Lys Lys Leu Lys Tyr Val
                85                  90                  95

Pro Val His His Tyr Asn Gln Tyr Leu Asn Gly Glu Leu Ser Ala Glu
            100                 105                 110

Asp Ala Thr Asp Leu Asn Asp Ile Phe Asn Ile Gly Tyr Phe Ser Leu
        115                 120                 125

Gln Thr Lys Val Ser Leu Ile Ala Gln Glu Thr Asp Ser Ser Ala Asp
    130                 135                 140

Ser Glu Pro Tyr Ser Val Gly Thr Phe Thr Phe Glu Pro Glu Ala Gly
145                 150                 155                 160

Leu Tyr Phe Ile Ala Lys Gly Ser Glu Glu Thr Leu Asp His Leu Asn
                165                 170                 175

Asn Ile Met Thr Ala Leu Gln Tyr Ser Gly Leu Gly Gly Lys Arg Asn
            180                 185                 190

Ala Gly Tyr Gly Gln Phe Glu Tyr Glu Ile Ile Asn Asn Gln Gln Leu
        195                 200                 205

Ser Lys Leu Leu Asn Gln Asn Gly Lys His Ser Ile Leu Leu Ser Thr
    210                 215                 220

Ala Met Ala Lys Lys Glu Glu Ile Glu Ser Ala Leu Lys Glu Ala Arg
225                 230                 235                 240

Tyr Ile Leu Thr Lys Arg Ser Gly Phe Val Gln Ser Thr Asn Tyr Ser
                245                 250                 255

Glu Met Leu Val Lys Lys Ser Asp Phe Tyr Ser Phe Ser Ser Gly Ser
            260                 265                 270

Val Phe Lys Asn Ile Phe Asn Gly Asp Ile Phe Asn Val Gly His Asn
        275                 280                 285

Gly Lys His Pro Val Tyr Arg Tyr Ala Lys Pro Leu Trp Leu Glu Val
    290                 295                 300

<210> SEQ ID NO 6
<211> LENGTH: 340
<212> TYPE: PRT
<213> ORGANISM: artificial sequence
<220> FEATURE:
<223> OTHER INFORMATION: CRISPR-associated enzyme

<400> SEQUENCE: 6

Met Thr Ile Lys Asn Tyr Glu Val Val Ile Lys Thr Leu Gly Pro Ile
1               5                   10                  15

His Ile Gly Ser Gly Gln Val Met Lys Lys Gln Asp Tyr Ile Tyr Asp
            20                  25                  30

Phe Tyr Asn Ser Lys Val Tyr Met Ile Asn Gly Asn Lys Leu Val Lys
        35                  40                  45

Phe Leu Lys Arg Lys Asn Leu Leu Tyr Thr Tyr Gln Asn Phe Leu Arg
    50                  55                  60

Tyr Pro Pro Lys Asn Pro Arg Glu Asn Gly Leu Lys Asp Tyr Leu Asp
65                  70                  75                  80

Ala Gln Asn Val Lys Gln Ser Glu Trp Glu Ala Phe Val Ser Tyr Ser
                85                  90                  95

Glu Lys Val Asn Gln Gly Lys Lys Tyr Gly Asn Thr Arg Pro Lys Pro
            100                 105                 110

Leu Asn Asp Leu His Leu Met Val Arg Asp Gly Gln Asn Lys Val Tyr
        115                 120                 125

Leu Pro Gly Ser Ser Ile Lys Gly Ala Ile Lys Thr Thr Leu Val Ser
    130                 135                 140

Lys Tyr Asn Asn Glu Lys Asn Lys Asp Ile Tyr Ser Lys Ile Lys Val
145                 150                 155                 160

Ser Asp Ser Lys Pro Ile Asp Glu Ser Asn Leu Ala Ile Tyr Gln Lys
                165                 170                 175

Ile Asp Ile Asn Lys Ser Glu Lys Ser Met Pro Leu Tyr Arg Glu Cys
            180                 185                 190

Ile Asp Val Asn Thr Glu Ile Lys Phe Lys Leu Thr Ile Glu Asp Glu
        195                 200                 205

Ile Tyr Ser Ile Asn Glu Ile Glu Gln Ser Ile Gln Asp Phe Tyr Lys
    210                 215                 220

Asn Tyr Tyr Asp Lys Trp Leu Val Gly Phe Lys Glu Thr Lys Gly Gly
225                 230                 235                 240

Arg Arg Phe Ala Leu Glu Gly Gly Ile Pro Asp Val Leu Asn Gln Asn
                245                 250                 255

Ile Leu Phe Leu Gly Ala Gly Thr Gly Phe Val Ser Lys Thr Thr His
            260                 265                 270

Tyr Gln Leu Lys Asn Arg Lys Gln Ala Lys Gln Asp Ser Phe Glu Ile
        275                 280                 285

Leu Thr Lys Lys Phe Arg Gly Thr Tyr Gly Lys Met Lys Glu Ile Pro
    290                 295                 300

Ser Asn Val Pro Val Ala Leu Lys Gly Thr Thr Asn Gln Ser Arg His
305                 310                 315                 320

Thr Ser Tyr Gln Gln Gly Met Cys Lys Val Ser Phe Gln Glu Leu Asn
                325                 330                 335

Asn Glu Val Leu
            340

<210> SEQ ID NO 7
<211> LENGTH: 422
<212> TYPE: PRT
<213> ORGANISM: artificial sequence
<220> FEATURE:
<223> OTHER INFORMATION: CRISPR-associated enzyme

<400> SEQUENCE: 7

Met Lys Ile Leu Phe Ser Pro Ile Gly Asn Ser Asp Pro Trp Arg Asn
1               5                   10                  15

Asp Arg Asp Gly Ala Met Leu His Ile Val Arg His Tyr Asn Leu Asp
            20                  25                  30

Lys Val Val Leu Tyr Phe Thr Arg Thr Ile Trp Glu Gly Asn Glu Asn
        35                  40                  45

Arg Lys Gly His Lys Ile Tyr Glu Trp Glu Lys Ile Ile Gln Thr Val
    50                  55                  60

Ser Pro Asn Thr Glu Val Glu Ile Ile Glu Asn Val Asp Asn Ala
65                  70                  75                  80

Gln Asp Tyr Asp Val Phe Lys Glu Lys Phe His Lys Tyr Leu Lys Ile
                85                  90                  95

```
Ile Glu Asp Ser Tyr Glu Asp Cys Glu Ile Ile Leu Asn Val Thr Ser
                100                 105                 110

Gly Thr Pro Gln Met Glu Ser Thr Leu Cys Leu Glu Tyr Ile Val Tyr
            115                 120                 125

Pro Glu Asn Lys Lys Cys Val Gln Val Ser Thr Pro Thr Lys Asp Ser
        130                 135                 140

Asn Ala Gly Ile Glu Tyr Ser Asn Pro Lys Asp Lys Val Glu Glu Phe
145                 150                 155                 160

Glu Ile Val Asn Glu Val Lys Lys Ser Glu Lys Arg Cys Lys Glu
                165                 170                 175

Ile Asn Ile Leu Ser Phe Arg Glu Ala Met Ile Arg Ser Gln Ile Leu
            180                 185                 190

Gly Leu Ile Asp Asn Tyr Asp Tyr Glu Gly Ala Leu Asn Leu Val Ser
        195                 200                 205

Asn Gln Lys Ser Phe Arg Asn Gly Lys Leu Leu Arg Lys Lys Leu Leu
        210                 215                 220

Ser Leu Thr Lys Gln Ile Lys Thr His Glu Val Phe Pro Glu Ile Asn
225                 230                 235                 240

Glu Lys Tyr Arg Asp Asp Ala Leu Lys Lys Ser Leu Phe His Tyr Leu
                245                 250                 255

Leu Leu Asn Met Arg Tyr Asn Arg Leu Asp Val Ala Glu Thr Leu Ile
            260                 265                 270

Arg Val Lys Ser Ile Ala Glu Phe Ile Leu Lys Thr Tyr Ile Glu Ile
        275                 280                 285

His Trp Pro Thr Leu Ile Ile Glu Lys Asp Gly Lys Pro Tyr Leu Asn
        290                 295                 300

Asp Glu Asp Asn Leu Ser Phe Val Tyr Lys Tyr Asn Leu Leu Leu Glu
305                 310                 315                 320

Lys Arg Lys Gln Asn Phe Asp Val Ser Arg Ile Leu Gly Leu Pro Ala
                325                 330                 335

Phe Ile Asp Ile Leu Thr Ile Leu Glu Pro Asn Ser Gln Leu Leu Lys
            340                 345                 350

Glu Val Asn Ala Val Asn Asp Ile Asn Gly Leu Arg Asn Ser Ile Ala
        355                 360                 365

His Asn Leu Asp Thr Leu Asn Leu Asp Lys Asn Lys Asn Tyr Lys Lys
        370                 375                 380

Ile Met Leu Ser Val Glu Ala Ile Lys Asn Met Leu His Ile Ser Phe
385                 390                 395                 400

Pro Glu Ile Glu Glu Asp Tyr Asn Tyr Phe Glu Glu Lys Asn Lys
                405                 410                 415

Glu Phe Lys Glu Leu Leu
            420

<210> SEQ ID NO 8
<211> LENGTH: 244
<212> TYPE: PRT
<213> ORGANISM: artificial sequence
<220> FEATURE:
<223> OTHER INFORMATION: CRISPR-associated enzyme

<400> SEQUENCE: 8

Met Ile Asn Lys Ile Thr Val Glu Leu Asp Leu Pro Glu Ser Ile Arg
1               5                   10                  15

Phe Gln Tyr Leu Gly Ser Val Leu His Gly Val Leu Met Asp Tyr Leu
            20                  25                  30
```

Ser Asp Asp Ile Ala Asp Gln Leu His His Glu Phe Ala Tyr Ser Pro
        35                  40                  45

Leu Lys Gln Arg Ile Tyr His Lys Asn Lys Lys Ile Ile Trp Glu Ile
    50                  55                  60

Val Cys Met Ser Asp Asn Leu Phe Lys Glu Val Val Lys Leu Phe Ser
65                  70                  75                  80

Ser Lys Asn Ser Leu Leu Leu Lys Tyr Tyr Gln Thr Asn Ile Asp Ile
                85                  90                  95

Gln Ser Phe Gln Ile Glu Lys Ile Asn Val Gln Asn Met Met Asn Gln
            100                 105                 110

Leu Leu Gln Val Glu Asp Leu Ser Arg Tyr Val Arg Leu Asn Ile Gln
        115                 120                 125

Thr Pro Met Ser Phe Lys Tyr Gln Asn Ser Tyr Met Ile Phe Pro Asp
    130                 135                 140

Val Lys Arg Phe Phe Arg Ser Ile Met Ile Gln Phe Asp Ala Phe Phe
145                 150                 155                 160

Glu Glu Tyr Arg Met Tyr Asp Lys Glu Thr Leu Asn Phe Leu Glu Lys
                165                 170                 175

Asn Val Asn Ile Val Asp Tyr Leu Lys Ser Thr Arg Phe Asn Leu
            180                 185                 190

Glu Lys Val Lys Ile Pro Ser Phe Thr Gly Glu Ile Val Phe Lys Ile
        195                 200                 205

Lys Gly Pro Leu Pro Phe Leu Gln Leu Thr His Phe Leu Leu Lys Phe
    210                 215                 220

Gly Glu Phe Ser Gly Ser Gly Ile Lys Thr Ser Leu Gly Met Gly Lys
225                 230                 235                 240

Tyr Ser Ile Ile

<210> SEQ ID NO 9
<211> LENGTH: 469
<212> TYPE: DNA
<213> ORGANISM: artificial sequence
<220> FEATURE:
<223> OTHER INFORMATION: CRISPR locus

<400> SEQUENCE: 9
cgaaatataa aaagaaatga aaggttaaat taatattaat tttattaaat gaataggcta      60
aaccatctta aatgtagtat actattaata taaatgtaat tattataaaa tttgtcaaaa     120
aaagtgacat atcatataat cttgtactag tgattgtcat attttttgac agcaaaaatg     180
atgcttgaaa tatagttgtg atggcatttg ttaaagtatc ggatcgatac ccaccccgaa     240
gaaaagggga cgagaacacg tatgccgaag tatataaatc atcagtacaa aggatcgata     300
cccaccccga agaaaagggg acgagaacta gtaataattg tcatttgcat acgttacatc     360
gatgatcgat acccaccccg aagaaaaggg gacgagaact agtacggtcg tgaacatttt     420
ttcttgattc tctgatcgat agccaccccg aagaaaaggg ggcagagtg                 469

<210> SEQ ID NO 10
<211> LENGTH: 35
<212> TYPE: DNA
<213> ORGANISM: artificial sequence
<220> FEATURE:
<223> OTHER INFORMATION: oligonucleotide

<400> SEQUENCE: 10 aattttttaat ttaagttctt gttcatcgtc ataaa                                35

<210> SEQ ID NO 11
<211> LENGTH: 35
<212> TYPE: DNA
<213> ORGANISM: artificial sequence
<220> FEATURE:
<223> OTHER INFORMATION: oligonucleotide

<400> SEQUENCE: 11
tatttatgac gatgaacaag aacttaaatt aaaaa                              35

<210> SEQ ID NO 12
<211> LENGTH: 35
<212> TYPE: DNA
<213> ORGANISM: artificial sequence
<220> FEATURE:
<223> OTHER INFORMATION: oligonucleotide

<400> SEQUENCE: 12
aatttcgagg aagttgcaat tgataatgaa aaatt                              35

<210> SEQ ID NO 13
<211> LENGTH: 35
<212> TYPE: DNA
<213> ORGANISM: artificial sequence
<220> FEATURE:
<223> OTHER INFORMATION: oligonucleotide

<400> SEQUENCE: 13
aatttttcat tatcaattgc aacttcctcg aaatt                              35

<210> SEQ ID NO 14
<211> LENGTH: 30
<212> TYPE: DNA
<213> ORGANISM: artificial sequence
<220> FEATURE:
<223> OTHER INFORMATION: oligonucleotide

<400> SEQUENCE: 14
gaaatttcca gcagaaactt taccgaaata                                    30

<210> SEQ ID NO 15
<211> LENGTH: 34
<212> TYPE: DNA
<213> ORGANISM: artificial sequence
<220> FEATURE:
<223> OTHER INFORMATION: oligonucleotide

<400> SEQUENCE: 15
cattttgttt ctgttcatgc ctctgccgac tgct                               34

<210> SEQ ID NO 16
<211> LENGTH: 34
<212> TYPE: DNA
<213> ORGANISM: artificial sequence
<220> FEATURE:
<223> OTHER INFORMATION: oligonucleotide

<400> SEQUENCE: 16
agcagtcggc agaggcatga acagaaacaa aatg                               34

<210> SEQ ID NO 17
<211> LENGTH: 36
<212> TYPE: DNA
<213> ORGANISM: artificial seq
<220> FEATURE:

<223> OTHER INFORMATION: oligonucleotide

<400> SEQUENCE: 17
taataagttt tatgctcctc agtttttaaa tcactt                                    36

<210> SEQ ID NO 18
<211> LENGTH: 36
<212> TYPE: DNA
<213> ORGANISM: artificial sequence
<220> FEATURE:
<223> OTHER INFORMATION: oligonucleotide

<400> SEQUENCE: 18
aagtgattta aaaactgagg agcataaaac ttatta                                    36

<210> SEQ ID NO 19
<211> LENGTH: 35
<212> TYPE: DNA
<213> ORGANISM: artificial sequence
<220> FEATURE:
<223> OTHER INFORMATION: oligonucleotide

<400> SEQUENCE: 19
tttttaaaaa ttctttggtt accatgcatc tcgct                                     35

<210> SEQ ID NO 20
<211> LENGTH: 35
<212> TYPE: DNA
<213> ORGANISM: artificial sequence
<220> FEATURE:
<223> OTHER INFORMATION: oligonucleotide

<400> SEQUENCE: 20
agcgagatgc atggtaacca agaatttttt aaaaa                                     35

<210> SEQ ID NO 21
<211> LENGTH: 36
<212> TYPE: DNA
<213> ORGANISM: artificial sequence
<220> FEATURE:
<223> OTHER INFORMATION: oligonucleotide

<400> SEQUENCE: 21
ttaaatcttt gattgctctt agctctagtt atgtat                                    36

<210> SEQ ID NO 22
<211> LENGTH: 36
<212> TYPE: DNA
<213> ORGANISM: artificial sequence
<220> FEATURE:
<223> OTHER INFORMATION: oligonucleotide

<400> SEQUENCE: 22
gtaaaccttt gattgctctt agctcgagtt atgtgc                                    36

<210> SEQ ID NO 23
<211> LENGTH: 36
<212> TYPE: DNA
<213> ORGANISM: artificial sequence
<220> FEATURE:
<223> OTHER INFORMATION: oligonucleotide

<400> SEQUENCE: 23
atacataact agagctaaga gcaatcaaag atttaa                                    36

```
<210> SEQ ID NO 24
<211> LENGTH: 36
<212> TYPE: DNA
<213> ORGANISM: artificial sequence
<220> FEATURE:
<223> OTHER INFORMATION: oligonucleotide

<400> SEQUENCE: 24
attcgtcatc ttcaagtaat gcctctaaat caataa                              36

<210> SEQ ID NO 25
<211> LENGTH: 36
<212> TYPE: DNA
<213> ORGANISM: artificial sequence
<220> FEATURE:
<223> OTHER INFORMATION: oligonucleotide

<400> SEQUENCE: 25
ttattgattt agaggcatta cttgaagatg acgaat                              36

<210> SEQ ID NO 26
<211> LENGTH: 30
<212> TYPE: DNA
<213> ORGANISM: artificial sequence
<220> FEATURE:
<223> OTHER INFORMATION: oligonucleotide

<400> SEQUENCE: 26
acttcacaca agataacatt attgatttag                                     30

<210> SEQ ID NO 27
<211> LENGTH: 35
<212> TYPE: DNA
<213> ORGANISM: artificial sequence
<220> FEATURE:
<223> OTHER INFORMATION: oligonucleotide

<400> SEQUENCE: 27
gcatgcacct tgcctgaatg ttttaaaaat tcatt                               35

<210> SEQ ID NO 28
<211> LENGTH: 35
<212> TYPE: DNA
<213> ORGANISM: artificial sequence
<220> FEATURE:
<223> OTHER INFORMATION: oligonucleotide

<400> SEQUENCE: 28
aatgaatttt taaaacattc aggcaaggtg catgc                               35

<210> SEQ ID NO 29
<211> LENGTH: 35
<212> TYPE: DNA
<213> ORGANISM: artificial sequence
<220> FEATURE:
<223> OTHER INFORMATION: oligonucleotide

<400> SEQUENCE: 29
atgtcaccta agtcaacacc atcatttttt attct                               35

<210> SEQ ID NO 30
<211> LENGTH: 35
<212> TYPE: DNA
<213> ORGANISM: artificial sequence
<220> FEATURE:
<223> OTHER INFORMATION: oligonucleotide
```

<400> SEQUENCE: 30
cttaggtgac attggctgtc gattttacac tgaag                           35

<210> SEQ ID NO 31
<211> LENGTH: 35
<212> TYPE: DNA
<213> ORGANISM: artificial sequence
<220> FEATURE:
<223> OTHER INFORMATION: oligonucleotide

<400> SEQUENCE: 31
ttatgatttt ttggagcata taaatcattt agtgt                           35

<210> SEQ ID NO 32
<211> LENGTH: 35
<212> TYPE: DNA
<213> ORGANISM: artificial sequence
<220> FEATURE:
<223> OTHER INFORMATION: oligonucleotide

<400> SEQUENCE: 32
cagaaagtgt attgcaacag attggctcaa aagtt                           35

<210> SEQ ID NO 33
<211> LENGTH: 34
<212> TYPE: DNA
<213> ORGANISM: artificial sequence
<220> FEATURE:
<223> OTHER INFORMATION: spacer sequence

<400> SEQUENCE: 33
ataaaagaaa agggattgat aaactatgaa atta                            34

<210> SEQ ID NO 34
<211> LENGTH: 36
<212> TYPE: DNA
<213> ORGANISM: artificial sequence
<220> FEATURE:
<223> OTHER INFORMATION: spacer sequence

<400> SEQUENCE: 34
tatgtattga tctcgattct cgttagtttc taaatt                          36

<210> SEQ ID NO 35
<211> LENGTH: 36
<212> TYPE: DNA
<213> ORGANISM: artificial sequence
<220> FEATURE:
<223> OTHER INFORMATION: spacer sequence

<400> SEQUENCE: 35
catttggaaa ctaacgagaa tcgagctcaa tacacg                          36

<210> SEQ ID NO 36
<211> LENGTH: 38
<212> TYPE: DNA
<213> ORGANISM: artificial sequence
<220> FEATURE:
<223> OTHER INFORMATION: spacer sequence

<400> SEQUENCE: 36
cacgctgtag tgaagtatag aaacggcatg agtacaat                        38

<210> SEQ ID NO 37
<211> LENGTH: 38

```
<212> TYPE: DNA
<213> ORGANISM: artificial sequence
<220> FEATURE:
<223> OTHER INFORMATION: spacer sequence

<400> SEQUENCE: 37
attgtactca tgccgtttct atacttcact acagcgtg                                38

<210> SEQ ID NO 38
<211> LENGTH: 35
<212> TYPE: DNA
<213> ORGANISM: artificial sequence
<220> FEATURE:
<223> OTHER INFORMATION: spacer sequence

<400> SEQUENCE: 38
acgtatgccg aagtatataa atcatcagta caaag                                  35

<210> SEQ ID NO 39
<211> LENGTH: 35
<212> TYPE: DNA
<213> ORGANISM: artificial sequence
<220> FEATURE:
<223> OTHER INFORMATION: spacer sequence

<400> SEQUENCE: 39
ctttgtactg atgatttata tacttcggca tacgt                                  35

<210> SEQ ID NO 40
<211> LENGTH: 35
<212> TYPE: DNA
<213> ORGANISM: artificial sequence
<220> FEATURE:
<223> OTHER INFORMATION: spacer sequence

<400> SEQUENCE: 40
tagtaataat tgtcatttgc atacgttaca tcgat                                  35

<210> SEQ ID NO 41
<211> LENGTH: 35
<212> TYPE: DNA
<213> ORGANISM: artificial sequence
<220> FEATURE:
<223> OTHER INFORMATION: spacer sequence

<400> SEQUENCE: 41
atcgatgtaa catatgcaaa tgacaattat tacta                                  35

<210> SEQ ID NO 42
<211> LENGTH: 34
<212> TYPE: DNA
<213> ORGANISM: artificial sequence
<220> FEATURE:
<223> OTHER INFORMATION: spacer sequence

<400> SEQUENCE: 42
tagaatgtta ttatctaagt ggtcgatgta ttcc                                   34

<210> SEQ ID NO 43
<211> LENGTH: 34
<212> TYPE: DNA
<213> ORGANISM: artificial sequence
<220> FEATURE:
<223> OTHER INFORMATION: spacer sequence

<400> SEQUENCE: 43
```
ggaatacatc gaccacatag ataataacat ccta                    34

<210> SEQ ID NO 44
<211> LENGTH: 35
<212> TYPE: DNA
<213> ORGANISM: artificial sequence
<220> FEATURE:
<223> OTHER INFORMATION: spacer sequence

<400> SEQUENCE: 44
aagttaacgg cattacctaa taaaaatatt ttagg                   35

<210> SEQ ID NO 45
<211> LENGTH: 35
<212> TYPE: DNA
<213> ORGANISM: artificial sequence
<220> FEATURE:
<223> OTHER INFORMATION: spacer sequence

<400> SEQUENCE: 45
cctaaaatgt ttttattagg taatgcggtc aactt                   35

<210> SEQ ID NO 46
<211> LENGTH: 33
<212> TYPE: DNA
<213> ORGANISM: artificial sequence
<220> FEATURE:
<223> OTHER INFORMATION: spacer sequence

<400> SEQUENCE: 46
tcatctttca tgtcactgat taattcattt gta                     33

<210> SEQ ID NO 47
<211> LENGTH: 33
<212> TYPE: DNA
<213> ORGANISM: artificial sequence
<220> FEATURE:
<223> OTHER INFORMATION: spacer sequence

<400> SEQUENCE: 47
tacaaatgaa ttaatcaatg atatgaaaga tga                     33

<210> SEQ ID NO 48
<211> LENGTH: 35
<212> TYPE: DNA
<213> ORGANISM: artificial sequence
<220> FEATURE:
<223> OTHER INFORMATION: spacer sequence

<400> SEQUENCE: 48
ccaaaccatt tagcacgata tttattaaaa ccata                   35

<210> SEQ ID NO 49
<211> LENGTH: 35
<212> TYPE: DNA
<213> ORGANISM: artificial sequence
<220> FEATURE:
<223> OTHER INFORMATION: spacer sequence

<400> SEQUENCE: 49
tacggattta ataaatatcg tgccaaatgg tttgg                   35

<210> SEQ ID NO 50
<211> LENGTH: 35
<212> TYPE: DNA
<213> ORGANISM: artificial sequence

```
<220> FEATURE:
<223> OTHER INFORMATION: spacer sequence

<400> SEQUENCE: 50
tatttttctc ctttagcaat cattctgtct agtac                          35

<210> SEQ ID NO 51
<211> LENGTH: 35
<212> TYPE: DNA
<213> ORGANISM: artificial sequence
<220> FEATURE:
<223> OTHER INFORMATION: spacer sequence

<400> SEQUENCE: 51
gtattagaca gaatgattgc tagaggagaa caata                          35

<210> SEQ ID NO 52
<211> LENGTH: 34
<212> TYPE: DNA
<213> ORGANISM: artificial sequence
<220> FEATURE:
<223> OTHER INFORMATION: oligonucleotide

<400> SEQUENCE: 52
ctttgtactg atgatttata tacttcggca tacg                           34

<210> SEQ ID NO 53
<211> LENGTH: 20
<212> TYPE: DNA
<213> ORGANISM: artificial sequence
<220> FEATURE:
<223> OTHER INFORMATION: oligonucloetide

<400> SEQUENCE: 53
taaatctaac aacactctaa                                           20

<210> SEQ ID NO 54
<211> LENGTH: 33
<212> TYPE: DNA
<213> ORGANISM: artificial sequence
<220> FEATURE:
<223> OTHER INFORMATION: oligonucleotide

<400> SEQUENCE: 54
aaaggtacca aatttaatgc tattttcctt cgc                            33

<210> SEQ ID NO 55
<211> LENGTH: 31
<212> TYPE: DNA
<213> ORGANISM: artificial sequence
<220> FEATURE:
<223> OTHER INFORMATION: oligonucleotide

<400> SEQUENCE: 55
aaaagatcta ataatgtatt tacgctgggg c                              31

<210> SEQ ID NO 56
<211> LENGTH: 62
<212> TYPE: DNA
<213> ORGANISM: artificial sequence
<220> FEATURE:
<223> OTHER INFORMATION: oligonucleotide

<400> SEQUENCE: 56
gttctcgtcc ccttttcttc ggggtgggta tcgatccttt gtactgatga tttatatact   60
``` tc                                                                      62

<210> SEQ ID NO 57
<211> LENGTH: 61
<212> TYPE: DNA
<213> ORGANISM: artificial sequence
<220> FEATURE:
<223> OTHER INFORMATION: oligonucleotide

<400> SEQUENCE: 57
agcagtcggc agaggcatga acagaaacaa aatgtaaatc taacaacact ctaaaaatt      60 g                                                                       61

<210> SEQ ID NO 58
<211> LENGTH: 62
<212> TYPE: DNA
<213> ORGANISM: artificial sequence
<220> FEATURE:
<223> OTHER INFORMATION: oligonucleotide

<400> SEQUENCE: 58
tatttatgac gatgaacaag aacttaaatt aaaaataaat ctaacaacac tctaaaaat      60 tg                                                                      62

<210> SEQ ID NO 59
<211> LENGTH: 62
<212> TYPE: DNA
<213> ORGANISM: artificial sequence
<220> FEATURE:
<223> OTHER INFORMATION: oligonucleotide

<400> SEQUENCE: 59
agcgagatgc atggtaacca aagaattttt aaaaataaat ctaacaacac tctaaaaat      60 tg                                                                      62

<210> SEQ ID NO 60
<211> LENGTH: 62
<212> TYPE: DNA
<213> ORGANISM: artificial sequence
<220> FEATURE:
<223> OTHER INFORMATION: oligonucleotide

<400> SEQUENCE: 60 aatgaattt taaacattc aggcaaggtg catgctaaat ctaacaacac tctaaaaat        60 tg                                                                      62

<210> SEQ ID NO 61
<211> LENGTH: 63
<212> TYPE: DNA
<213> ORGANISM: artificial sequence
<220> FEATURE:
<223> OTHER INFORMATION: oligonucleotide

<400> SEQUENCE: 61
ttaaatcttt gattgctctt agctctagtt atgtattaaa tctaacaaca ctctaaaaaa      60
ttg                                                                     63

<210> SEQ ID NO 62
<211> LENGTH: 63
<212> TYPE: DNA
<213> ORGANISM: artificial sequence
<220> FEATURE:
<223> OTHER INFORMATION: oligonucleotide

<400> SEQUENCE: 62
gtaaaccttt gattgctctt agctcgagtt atgtgctaaa tctaacaaca ctctaaaaaa    60
ttg    63

<210> SEQ ID NO 63
<211> LENGTH: 62
<212> TYPE: DNA
<213> ORGANISM: artificial sequence
<220> FEATURE:
<223> OTHER INFORMATION: oligonucleotide

<400> SEQUENCE: 63
cttaggtgac attggctgtc gattttacac tgaagtaaat ctaacaacac tctaaaaat    60 tg    62

<210> SEQ ID NO 64
<211> LENGTH: 62
<212> TYPE: DNA
<213> ORGANISM: artificial sequence
<220> FEATURE:
<223> OTHER INFORMATION: oligonucleotide

<400> SEQUENCE: 64
cagaaagtgt attgcaacag attggctcaa aagtttaaat ctaacaacac tctaaaaat    60 tg    62

<210> SEQ ID NO 65
<211> LENGTH: 62
<212> TYPE: DNA
<213> ORGANISM: artificial sequence
<220> FEATURE:
<223> OTHER INFORMATION: oligonucleotide

<400> SEQUENCE: 65
atgtcaccta agtcaacacc atcatttttt attcttaaat ctaacaacac tctaaaaat    60 tg    62

<210> SEQ ID NO 66
<211> LENGTH: 62
<212> TYPE: DNA
<213> ORGANISM: artificial sequence
<220> FEATURE:
<223> OTHER INFORMATION: oligonucleotide

<400> SEQUENCE: 66
ttatgatttt ttggagcata taaatcattt agtgttaaat ctaacaacac tctaaaaat    60 tg    62

<210> SEQ ID NO 67
<211> LENGTH: 61
<212> TYPE: DNA
<213> ORGANISM: artificial sequence
<220> FEATURE:
<223> OTHER INFORMATION: oligonucleotide

<400> SEQUENCE: 67
cattttgttt ctgttcatgc ctctgccgac tgcttaaatc taacaacact ctaaaaatt    60 g    61

<210> SEQ ID NO 68

```
<211> LENGTH: 62
<212> TYPE: DNA
<213> ORGANISM: artificial sequence
<220> FEATURE:
<223> OTHER INFORMATION: oligonucleotide

<400> SEQUENCE: 68 aattttctcat tatcaattgc aacttcctcg aaatttaaat ctaacaacac tctaaaaaat      60
tg                                                                     62

<210> SEQ ID NO 69
<211> LENGTH: 62
<212> TYPE: DNA
<213> ORGANISM: artificial sequence
<220> FEATURE:
<223> OTHER INFORMATION: oligonucleotide

<400> SEQUENCE: 69
aatttcgagg aagttgcaat tgataatgaa aaatttaaat ctaacaacac tctaaaaaat      60
tg                                                                     62

<210> SEQ ID NO 70
<211> LENGTH: 63
<212> TYPE: DNA
<213> ORGANISM: artificial sequence
<220> FEATURE:
<223> OTHER INFORMATION: oligonucleotide

<400> SEQUENCE: 70
atacataact agagctaaga gcaatcaaag atttaataaa tctaacaaca ctctaaaaaa      60
ttg                                                                    63

<210> SEQ ID NO 71
<211> LENGTH: 63
<212> TYPE: DNA
<213> ORGANISM: artificial sequence
<220> FEATURE:
<223> OTHER INFORMATION: oligonucleotide

<400> SEQUENCE: 71
attcgtcatc ttcaagtaat gcctctaaat caataataaa tctaacaaca ctctaaaaaa      60
ttg                                                                    63

<210> SEQ ID NO 72
<211> LENGTH: 58
<212> TYPE: DNA
<213> ORGANISM: artificial sequence
<220> FEATURE:
<223> OTHER INFORMATION: oligonucleotide

<400> SEQUENCE: 72
tgagaccagt ctcggaagct caaaggtctc ttaaatctaa caacactcta aaaaattg       58

<210> SEQ ID NO 73
<211> LENGTH: 40
<212> TYPE: DNA
<213> ORGANISM: artificial sequence
<220> FEATURE:
<223> OTHER INFORMATION: oligonucleotide

<400> SEQUENCE: 73
gaacttattg atttagaggc attacttgaa gatgacgaat                            40
```

```
<210> SEQ ID NO 74
<211> LENGTH: 40
<212> TYPE: DNA
<213> ORGANISM: artificial sequence
<220> FEATURE:
<223> OTHER INFORMATION: oligonucleotide

<400> SEQUENCE: 74
tttaattcgt catcttcaag taatgcctct aaatcaataa                              40

<210> SEQ ID NO 75
<211> LENGTH: 39
<212> TYPE: DNA
<213> ORGANISM: artificial sequence
<220> FEATURE:
<223> OTHER INFORMATION: oligonucleotide

<400> SEQUENCE: 75
gaacaatttt taatttaagt tcttgttcat cgtcataaa                               39

<210> SEQ ID NO 76
<211> LENGTH: 39
<212> TYPE: DNA
<213> ORGANISM: artificial sequence
<220> FEATURE:
<223> OTHER INFORMATION: oligonucleotide

<400> SEQUENCE: 76
tttatttatg acgatgaaca agaacttaaa ttaaaaatt                               39

<210> SEQ ID NO 77
<211> LENGTH: 39
<212> TYPE: DNA
<213> ORGANISM: artificial sequence
<220> FEATURE:
<223> OTHER INFORMATION: oligonucleotide

<400> SEQUENCE: 77 gaactttta aaaattcttt ggttaccatg catctcgct                                39

<210> SEQ ID NO 78
<211> LENGTH: 39
<212> TYPE: DNA
<213> ORGANISM: artificial sequence
<220> FEATURE:
<223> OTHER INFORMATION: oligonucleotide

<400> SEQUENCE: 78
tttaagcgag atgcatggta accaaagaat ttttaaaaa                               39

<210> SEQ ID NO 79
<211> LENGTH: 39
<212> TYPE: DNA
<213> ORGANISM: artificial sequence
<220> FEATURE:
<223> OTHER INFORMATION: oligonucleotide

<400> SEQUENCE: 79
gaacgcatgc accttgcctg aatgttttaa aaattcatt                               39

<210> SEQ ID NO 80
<211> LENGTH: 39
<212> TYPE: DNA
<213> ORGANISM: artificial sequence
<220> FEATURE:
<223> OTHER INFORMATION: oligonucleotide
```

<400> SEQUENCE: 80
tttaaatgaa tttttaaaac attcaggcaa ggtgcatgc    39

<210> SEQ ID NO 81
<211> LENGTH: 40
<212> TYPE: DNA
<213> ORGANISM: artificial sequence
<220> FEATURE:
<223> OTHER INFORMATION: oligonucleotide

<400> SEQUENCE: 81
gaacaagtga tttaaaaact gaggagcata aaacttatta    40

<210> SEQ ID NO 82
<211> LENGTH: 40
<212> TYPE: DNA
<213> ORGANISM: artificial sequence
<220> FEATURE:
<223> OTHER INFORMATION: oligonucleotide

<400> SEQUENCE: 82
tttataataa gttttatgct cctcagtttt taaatcactt    40

<210> SEQ ID NO 83
<211> LENGTH: 40
<212> TYPE: DNA
<213> ORGANISM: artificial sequence
<220> FEATURE:
<223> OTHER INFORMATION: oligonucleotide

<400> SEQUENCE: 83
gaactaataa gttttatgct cctcagtttt taaatcactt    40

<210> SEQ ID NO 84
<211> LENGTH: 40
<212> TYPE: DNA
<213> ORGANISM: artificial sequence
<220> FEATURE:
<223> OTHER INFORMATION: oligonucleotide

<400> SEQUENCE: 84
tttaaagtga tttaaaaact gaggagcata aaacttatta    40

<210> SEQ ID NO 85
<211> LENGTH: 32
<212> TYPE: DNA
<213> ORGANISM: artificial sequence
<220> FEATURE:
<223> OTHER INFORMATION: oligonucleotide

<400> SEQUENCE: 85
aaactcgtgg attctgtgat ttggatcctt cc    32

<210> SEQ ID NO 86
<211> LENGTH: 32
<212> TYPE: DNA
<213> ORGANISM: artificial sequence
<220> FEATURE:
<223> OTHER INFORMATION: oligonucleotide

<400> SEQUENCE: 86
aaaaagatct tatgactgtt atgtggttat cg    32

<210> SEQ ID NO 87
<211> LENGTH: 31

<212> TYPE: DNA
<213> ORGANISM: artificial sequence
<220> FEATURE:
<223> OTHER INFORMATION: oligonucleotide

<400> SEQUENCE: 87
aaaaagatct tgcataattc acgctgacct c                                31

<210> SEQ ID NO 88
<211> LENGTH: 32
<212> TYPE: DNA
<213> ORGANISM: artificial sequence
<220> FEATURE:
<223> OTHER INFORMATION: oligonucleotide

<400> SEQUENCE: 88
aaaacacgag cgtttgttga actaatgggt gc                               32

<210> SEQ ID NO 89
<211> LENGTH: 53
<212> TYPE: DNA
<213> ORGANISM: artificial sequence
<220> FEATURE:
<223> OTHER INFORMATION: oligonucleotide

<400> SEQUENCE: 89
aaaaagcgca agaagaaatc aaccagcgca ctcgtagact attttgtct aaa         53

<210> SEQ ID NO 90
<211> LENGTH: 44
<212> TYPE: DNA
<213> ORGANISM: artificial sequence
<220> FEATURE:
<223> OTHER INFORMATION: oligonucleotide

<400> SEQUENCE: 90
acactgagac ttgttgagtt caaacgaaaa ttggataaag tggg                  44

<210> SEQ ID NO 91
<211> LENGTH: 27
<212> TYPE: DNA
<213> ORGANISM: artificial sequence
<220> FEATURE:
<223> OTHER INFORMATION: oligonucleotide

<400> SEQUENCE: 91
attatttctt aataactaaa aatatgg                                     27

<210> SEQ ID NO 92
<211> LENGTH: 44
<212> TYPE: DNA
<213> ORGANISM: artificial sequence
<220> FEATURE:
<223> OTHER INFORMATION: oligonucleotide

<400> SEQUENCE: 92
ctttatccaa ttttcgtttg aactcaacaa gtctcagtgt gctg                  44

<210> SEQ ID NO 93
<211> LENGTH: 35
<212> TYPE: DNA
<213> ORGANISM: artificial sequence
<220> FEATURE:
<223> OTHER INFORMATION: oligonucleotide

<400> SEQUENCE: 93
aaacacttca cacaagataa cattattgat ttagg          35

<210> SEQ ID NO 94
<211> LENGTH: 35
<212> TYPE: DNA
<213> ORGANISM: artificial sequence
<220> FEATURE:
<223> OTHER INFORMATION: oligonucleotide

<400> SEQUENCE: 94
aaaacctaaa tcaataatgt tatcttgtgt gaagt          35

<210> SEQ ID NO 95
<211> LENGTH: 35
<212> TYPE: DNA
<213> ORGANISM: artificial sequence
<220> FEATURE:
<223> OTHER INFORMATION: oligonucleotide

<400> SEQUENCE: 95
aaacgaaatt tccagcagaa actttaccga aatag          35

<210> SEQ ID NO 96
<211> LENGTH: 35
<212> TYPE: DNA
<213> ORGANISM: artificial sequence
<220> FEATURE:
<223> OTHER INFORMATION: oligonucletide

<400> SEQUENCE: 96
aaaactattt cggtaaagtt tctgctggaa atttc          35

<210> SEQ ID NO 97
<211> LENGTH: 21
<212> TYPE: DNA
<213> ORGANISM: artificial sequence
<220> FEATURE:
<223> OTHER INFORMATION: oligonucleotide

<400> SEQUENCE: 97
gaagctttag ctttgcagtg g          21

<210> SEQ ID NO 98
<211> LENGTH: 22
<212> TYPE: DNA
<213> ORGANISM: artificial sequence
<220> FEATURE:
<223> OTHER INFORMATION: oligonucleotide

<400> SEQUENCE: 98
ctgtaataga catcgttcgc ag          22

<210> SEQ ID NO 99
<211> LENGTH: 26
<212> TYPE: DNA
<213> ORGANISM: artificial sequence
<220> FEATURE:
<223> OTHER INFORMATION: oligonucleotide

<400> SEQUENCE: 99
gctacattaa ttatagggaa tcttac          26

<210> SEQ ID NO 100
<211> LENGTH: 23
<212> TYPE: DNA
<213> ORGANISM: artificial sequence
<220> FEATURE:
<223> OTHER INFORMATION: oligonucleotide

<400> SEQUENCE: 100
tcctaacaga aattgcgtta aag                                               23

<210> SEQ ID NO 101
<211> LENGTH: 26
<212> TYPE: DNA
<213> ORGANISM: artificial sequence
<220> FEATURE:
<223> OTHER INFORMATION: oligonucleotide

<400> SEQUENCE: 101
ttttatacaa tactatttat aagtgc                                            26

<210> SEQ ID NO 102
<211> LENGTH: 24
<212> TYPE: DNA
<213> ORGANISM: artificial sequence
<220> FEATURE:
<223> OTHER INFORMATION: oligonucleotide

<400> SEQUENCE: 102
catatagttt tatgcctaaa aacc                                              24

<210> SEQ ID NO 103
<211> LENGTH: 25
<212> TYPE: DNA
<213> ORGANISM: artificial sequence
<220> FEATURE:
<223> OTHER INFORMATION: oligonucleotide

<400> SEQUENCE: 103
atatatttat ttggctcata tttgc                                             25

<210> SEQ ID NO 104
<211> LENGTH: 28
<212> TYPE: DNA
<213> ORGANISM: artificial sequence
<220> FEATURE:
<223> OTHER INFORMATION: oligonucleotide

<400> SEQUENCE: 104
aaactcgagc gcgcaagctg gggatccg                                          28

<210> SEQ ID NO 105
<211> LENGTH: 33
<212> TYPE: DNA
<213> ORGANISM: artificial sequence
<220> FEATURE:
<223> OTHER INFORMATION: oligonucleotide

<400> SEQUENCE: 105
aaactcgagt aggtactaaa acaattcatc cag                                    33

<210> SEQ ID NO 106
<211> LENGTH: 30
<212> TYPE: DNA
<213> ORGANISM: artificial sequence
<220> FEATURE:
<223> OTHER INFORMATION: oligonucleotide

<400> SEQUENCE: 106
aaactcgagc tgagagtgca ccatatgcgg                                        30

<210> SEQ ID NO 107
<211> LENGTH: 31
<212> TYPE: DNA
<213> ORGANISM: artificial sequence
<220> FEATURE:
<223> OTHER INFORMATION: oligonucleotide

<400> SEQUENCE: 107
aaactcgagc ttaatagctc acgctatgcc g                              31

<210> SEQ ID NO 108
<211> LENGTH: 46
<212> TYPE: DNA
<213> ORGANISM: artificial sequence
<220> FEATURE:
<223> OTHER INFORMATION: oligonucleotide

<400> SEQUENCE: 108
taattcctcc tttttgttga cattatatca ttgatagagt tatttg              46

<210> SEQ ID NO 109
<211> LENGTH: 46
<212> TYPE: DNA
<213> ORGANISM: artificial sequence
<220> FEATURE:
<223> OTHER INFORMATION: oligonucleotide

<400> SEQUENCE: 109
actctatcaa tgatataatg tcaacaaaaa ggaggaatta atgatg              46

<210> SEQ ID NO 110
<211> LENGTH: 46
<212> TYPE: DNA
<213> ORGANISM: artificial sequence
<220> FEATURE:
<223> OTHER INFORMATION: oligonucleotide

<400> SEQUENCE: 110
tgacactcta tcattgatag agcataatta aaataagctt gatatc              46

<210> SEQ ID NO 111
<211> LENGTH: 46
<212> TYPE: DNA
<213> ORGANISM: artificial sequence
<220> FEATURE:
<223> OTHER INFORMATION: oligonucleotide

<400> SEQUENCE: 111
aagcttattt taattatgct ctatcaatga tagagtgtca atattt              46

<210> SEQ ID NO 112
<211> LENGTH: 33
<212> TYPE: DNA
<213> ORGANISM: artificial sequence
<220> FEATURE:
<223> OTHER INFORMATION: oligonucleotide

<400> SEQUENCE: 112
ttgatagagt gatatcgaat tcggaggcat atc                            33

<210> SEQ ID NO 113
<211> LENGTH: 32
<212> TYPE: DNA
<213> ORGANISM: artificial sequence
<220> FEATURE:
<223> OTHER INFORMATION: oligonucleotide

<400> SEQUENCE: 113
tgatagagag cttattttaa ttatgctcta tc                               32

<210> SEQ ID NO 114
<211> LENGTH: 65
<212> TYPE: DNA
<213> ORGANISM: artificial sequence
<220> FEATURE:
<223> OTHER INFORMATION: oligonucleotide

<400> SEQUENCE: 114
gatctcaaga taacattatt gatttagagg cattacttga agatgacgaa ttagaagcaa   60
accgc                                                              65

<210> SEQ ID NO 115
<211> LENGTH: 59
<212> TYPE: DNA
<213> ORGANISM: artificial sequence
<220> FEATURE:
<223> OTHER INFORMATION: oligonucleotide

<400> SEQUENCE: 115
ggtttgcttc taattcgtca tcttcaagta atgcctctaa atcaataatg ttatcttga    59

<210> SEQ ID NO 116
<211> LENGTH: 65
<212> TYPE: DNA
<213> ORGANISM: artificial sequence
<220> FEATURE:
<223> OTHER INFORMATION: oligonucleotide

<400> SEQUENCE: 116
gatcttttgc ttctaattcg tcatcttcaa gtaatgcctc taaatcaata atgttatctt   60
gccgc                                                              65

<210> SEQ ID NO 117
<211> LENGTH: 59
<212> TYPE: DNA
<213> ORGANISM: artificial sequence
<220> FEATURE:
<223> OTHER INFORMATION: oligonucleotide

<400> SEQUENCE: 117
ggcaagataa cattattgat ttagaggcat tacttgaaga tgacgaatta gaagcaaaa    59

<210> SEQ ID NO 118
<211> LENGTH: 24
<212> TYPE: DNA
<213> ORGANISM: artificial sequence
<220> FEATURE:
<223> OTHER INFORMATION: oligonucleotide

<400> SEQUENCE: 118
tcttattcaa gacaacactt acac                                         24

<210> SEQ ID NO 119
<211> LENGTH: 23
<212> TYPE: DNA
<213> ORGANISM: artificial sequence
<220> FEATURE:
<223> OTHER INFORMATION: oligonucleotide

<400> SEQUENCE: 119

```
atctaacatc tcaatggcta agg                                    23
```

<210> SEQ ID NO 120
<211> LENGTH: 47
<212> TYPE: DNA
<213> ORGANISM: artificial sequence
<220> FEATURE:
<223> OTHER INFORMATION: oligonucleotide

<400> SEQUENCE: 120

```
ccacatacct atatctgccc tttttctgcc cttttttatt tttaaag          47
```

<210> SEQ ID NO 121
<211> LENGTH: 39
<212> TYPE: DNA
<213> ORGANISM: artificial sequence
<220> FEATURE:
<223> OTHER INFORMATION: oligonucleotide

<400> SEQUENCE: 121

```
gtgtactaaa aggtaatcga tacggttata tttattccc                   39
```

<210> SEQ ID NO 122
<211> LENGTH: 41
<212> TYPE: DNA
<213> ORGANISM: artificial sequence
<220> FEATURE:
<223> OTHER INFORMATION: oligonucleotide

<400> SEQUENCE: 122

```
ggcagaaaaa gggcagatat aggtatgtgg ttttgtattg g                41
```

<210> SEQ ID NO 123
<211> LENGTH: 39
<212> TYPE: DNA
<213> ORGANISM: artificial sequence
<220> FEATURE:
<223> OTHER INFORMATION: oligonucleotide

<400> SEQUENCE: 123

```
tataaccgta tcgattacct tttagtacac aagttttc                    39
```

<210> SEQ ID NO 124
<211> LENGTH: 23
<212> TYPE: DNA
<213> ORGANISM: artificial sequence
<220> FEATURE:
<223> OTHER INFORMATION: oligonucleotide

<400> SEQUENCE: 124

```
gttaatgtta cgaatgatga acc                                    23
```

<210> SEQ ID NO 125
<211> LENGTH: 22
<212> TYPE: DNA
<213> ORGANISM: artificial sequence
<220> FEATURE:
<223> OTHER INFORMATION: oligonucleotide

<400> SEQUENCE: 125

```
ttggcaagtt ctgcaccttt ac                                     22
```

<210> SEQ ID NO 126
<211> LENGTH: 23
<212> TYPE: DNA
<213> ORGANISM: artificial sequence

```
<220> FEATURE:
<223> OTHER INFORMATION: oligonucleotide

<400> SEQUENCE: 126
aagatgcaac aatgggaacc aag                                              23

<210> SEQ ID NO 127
<211> LENGTH: 27
<212> TYPE: DNA
<213> ORGANISM: artificial sequence
<220> FEATURE:
<223> OTHER INFORMATION: oligonucleotide

<400> SEQUENCE: 127
ctaaatgtga tataataaaa taaaaag                                          27

<210> SEQ ID NO 128
<211> LENGTH: 23
<212> TYPE: DNA
<213> ORGANISM: artificial sequence
<220> FEATURE:
<223> OTHER INFORMATION: oligonucleotide

<400> SEQUENCE: 128
ataaagacac cgattcaact atg                                              23

<210> SEQ ID NO 129
<211> LENGTH: 24
<212> TYPE: DNA
<213> ORGANISM: artificial sequence
<220> FEATURE:
<223> OTHER INFORMATION: oligonucleotide

<400> SEQUENCE: 129
aagataaaga atttgctcaa gacg                                             24

<210> SEQ ID NO 130
<211> LENGTH: 23
<212> TYPE: DNA
<213> ORGANISM: artificial sequence
<220> FEATURE:
<223> OTHER INFORMATION: oligonucleotide

<400> SEQUENCE: 130
ttcatcagct gacattaact cac                                              23

<210> SEQ ID NO 131
<211> LENGTH: 23
<212> TYPE: DNA
<213> ORGANISM: artificial sequence
<220> FEATURE:
<223> OTHER INFORMATION: oligonucleotide

<400> SEQUENCE: 131
gcaagagagt taaaggtat acg                                               23

<210> SEQ ID NO 132
<211> LENGTH: 24
<212> TYPE: DNA
<213> ORGANISM: artificial sequence
<220> FEATURE:
<223> OTHER INFORMATION: oligonucleotide

<400> SEQUENCE: 132
ctgtatatcc ttgtatcaac tatc                                             24
```

<210> SEQ ID NO 133
<211> LENGTH: 23
<212> TYPE: DNA
<213> ORGANISM: artificial sequence
<220> FEATURE:
<223> OTHER INFORMATION: oligonucleotide

<400> SEQUENCE: 133
cctatctgac aattcctgaa tag                                    23

<210> SEQ ID NO 134
<211> LENGTH: 21
<212> TYPE: DNA
<213> ORGANISM: artificial sequence
<220> FEATURE:
<223> OTHER INFORMATION: oligonucleotide

<400> SEQUENCE: 134
taccctagtt aacgtctctt g                                      21

<210> SEQ ID NO 135
<211> LENGTH: 23
<212> TYPE: DNA
<213> ORGANISM: artificial sequence
<220> FEATURE:
<223> OTHER INFORMATION: oligonucleotide

<400> SEQUENCE: 135
cgtttcggta cttatttcaa cac                                    23

<210> SEQ ID NO 136
<211> LENGTH: 25
<212> TYPE: DNA
<213> ORGANISM: artificial sequence
<220> FEATURE:
<223> OTHER INFORMATION: oligonucleotide

<400> SEQUENCE: 136
gttaattcta tgtccatttg taacc                                  25

<210> SEQ ID NO 137
<211> LENGTH: 55
<212> TYPE: DNA
<213> ORGANISM: artificial sequence
<220> FEATURE:
<223> OTHER INFORMATION: oligonucleotide

<400> SEQUENCE: 137
ggggacaagt ttgtacaaaa aagcaggcta ttcgaaattg tacctgtttc atctc   55

<210> SEQ ID NO 138
<211> LENGTH: 46
<212> TYPE: DNA
<213> ORGANISM: artificial sequence
<220> FEATURE:
<223> OTHER INFORMATION: oligonucleotide

<400> SEQUENCE: 138
cgaaaaaaga gtgtcttgtg atggtatcat atcggtatca aataac            46

<210> SEQ ID NO 139
<211> LENGTH: 44
<212> TYPE: DNA
<213> ORGANISM: artificial sequence
<220> FEATURE:
<223> OTHER INFORMATION: oligonucleotide

<400> SEQUENCE: 139
tgataccgat atgataccat cacaagacac tcttttttcg cacc                        44

<210> SEQ ID NO 140
<211> LENGTH: 46
<212> TYPE: DNA
<213> ORGANISM: artificial sequence
<220> FEATURE:
<223> OTHER INFORMATION: oligonucleotide

<400> SEQUENCE: 140
ctatgaacat atttgattaa cgtatataga tttcataaag tctaac                      46

<210> SEQ ID NO 141
<211> LENGTH: 47
<212> TYPE: DNA
<213> ORGANISM: artificial sequence
<220> FEATURE:
<223> OTHER INFORMATION: oligonucleotide

<400> SEQUENCE: 141
ctttatgaaa tctatatacg ttaatcaaat atgttcatag cttgatg                     47

<210> SEQ ID NO 142
<211> LENGTH: 53
<212> TYPE: DNA
<213> ORGANISM: artificial sequence
<220> FEATURE:
<223> OTHER INFORMATION: oligonucleotide

<400> SEQUENCE: 142
ggggaccact ttgtacaaga aagctgggtc attagatata aagatgtata cgg              53

<210> SEQ ID NO 143
<211> LENGTH: 18
<212> TYPE: DNA
<213> ORGANISM: artificial sequence
<220> FEATURE:
<223> OTHER INFORMATION: oligonucleotide

<400> SEQUENCE: 143
tacgactcac tatagggg                                                     18

<210> SEQ ID NO 144
<211> LENGTH: 23
<212> TYPE: DNA
<213> ORGANISM: artificial sequence
<220> FEATURE:
<223> OTHER INFORMATION: oligonucleotide

<400> SEQUENCE: 144
tctacttaat ctgataagtg agc                                               23

<210> SEQ ID NO 145
<211> LENGTH: 28
<212> TYPE: DNA
<213> ORGANISM: artificial sequence
<220> FEATURE:
<223> OTHER INFORMATION: oligonucleotide

<400> SEQUENCE: 145
aaacccggga cgcaaaccgc ctctcccc                                          28

<210> SEQ ID NO 146

```
<211> LENGTH: 31
<212> TYPE: DNA
<213> ORGANISM: artificial sequence
<220> FEATURE:
<223> OTHER INFORMATION: oligonucleotide

<400> SEQUENCE: 146
cctccttata aaattagtat aattatagca c                              31

<210> SEQ ID NO 147
<211> LENGTH: 20
<212> TYPE: DNA
<213> ORGANISM: artificial sequence
<220> FEATURE:
<223> OTHER INFORMATION: oligonucleotide

<400> SEQUENCE: 147
gtgacctcct tgccattgtc                                           20

<210> SEQ ID NO 148
<211> LENGTH: 44
<212> TYPE: DNA
<213> ORGANISM: artificial sequence
<220> FEATURE:
<223> OTHER INFORMATION: oligonucleotide

<400> SEQUENCE: 148
tatacttcgg catacgtgtt ctcgttatct tgttcatatt tatc                44

<210> SEQ ID NO 149
<211> LENGTH: 44
<212> TYPE: DNA
<213> ORGANISM: artificial sequence
<220> FEATURE:
<223> OTHER INFORMATION: oligonucleotide

<400> SEQUENCE: 149
gataaatatg aacaagataa cgagaacacg tatgccgaag tata                44

<210> SEQ ID NO 150
<211> LENGTH: 58
<212> TYPE: DNA
<213> ORGANISM: artificial sequence
<220> FEATURE:
<223> OTHER INFORMATION: oligonucleotide

<400> SEQUENCE: 150
tgagaccagt ctcggaagct caaaggtctc ttaaatctaa caacactcta aaaaattg  58

<210> SEQ ID NO 151
<211> LENGTH: 58
<212> TYPE: DNA
<213> ORGANISM: artificial sequence
<220> FEATURE:
<223> OTHER INFORMATION: oligonucleotide

<400> SEQUENCE: 151
gttctcgtcc cctttcttc ggggtgggta tcgatccgat actttaacaa atgccatc   58

<210> SEQ ID NO 152
<211> LENGTH: 39
<212> TYPE: DNA
<213> ORGANISM: artificial sequence
<220> FEATURE:
<223> OTHER INFORMATION: oligonucleotide

<400> SEQUENCE: 152
```
gaacattcgt catcttcaag taatgcctct aaatcaata 39

<210> SEQ ID NO 153
<211> LENGTH: 39
<212> TYPE: DNA
<213> ORGANISM: artificial sequence
<220> FEATURE:
<223> OTHER INFORMATION: oligonucleotide

<400> SEQUENCE: 153
gatctattga tttagaggca ttacttgaag atgacgaat 39

<210> SEQ ID NO 154
<211> LENGTH: 50
<212> TYPE: DNA
<213> ORGANISM: artificial sequence
<220> FEATURE:
<223> OTHER INFORMATION: oligonucleotide

<400> SEQUENCE: 154
ggtaaatcaa aactaactaa caaatacatt agtttcccac ctctatcatc 50

<210> SEQ ID NO 155
<211> LENGTH: 50
<212> TYPE: DNA
<213> ORGANISM: artificial sequence
<220> FEATURE:
<223> OTHER INFORMATION: oligonucleotide

<400> SEQUENCE: 155
gatgatagag gtgggaaact aatgtatttg ttagttagtt ttgatttacc 50

<210> SEQ ID NO 156
<211> LENGTH: 55
<212> TYPE: DNA
<213> ORGANISM: artificial sequence
<220> FEATURE:
<223> OTHER INFORMATION: oligonucleotide

<400> SEQUENCE: 156
tatttagaga acgtatgccg aagtatataa atcatcagta caaaggtaag aatca 55

<210> SEQ ID NO 157
<211> LENGTH: 55
<212> TYPE: DNA
<213> ORGANISM: artificial sequence
<220> FEATURE:
<223> OTHER INFORMATION: oligonucleotide

<400> SEQUENCE: 157
tgattcttac ctttgtactg atgatttata tacttcggca tacgttctct aaata 55

<210> SEQ ID NO 158
<211> LENGTH: 90
<212> TYPE: DNA
<213> ORGANISM: artificial sequence
<220> FEATURE:
<223> OTHER INFORMATION: oligonucleotide

<400> SEQUENCE: 158
gcggtaattt taatgagata tttagagaac gtatgccgaa gtatataaat catcagtaca 60
aaggtaagaa tcacagtaaa cagcgcgcgg 90

<210> SEQ ID NO 159

<211> LENGTH: 90
<212> TYPE: DNA
<213> ORGANISM: artificial sequence
<220> FEATURE:
<223> OTHER INFORMATION: oligonucleotide

<400> SEQUENCE: 159
ccgcgcgctg tttactgtga ttcttacctt tgtactgatg atttatatac ttcggcatac    60
gttctctaaa tatctcatta aaattaccgc                                     90

<210> SEQ ID NO 160
<211> LENGTH: 58
<212> TYPE: DNA
<213> ORGANISM: artificial sequence
<220> FEATURE:
<223> OTHER INFORMATION: oligonucleotide

<400> SEQUENCE: 160
gcggcgtaga gaacgtatgc cgaagtatat aaatcatcag tacaaaggta aggcggcg      58

<210> SEQ ID NO 161
<211> LENGTH: 58
<212> TYPE: DNA
<213> ORGANISM: artificial sequence
<220> FEATURE:
<223> OTHER INFORMATION: oligonucleotide

<400> SEQUENCE: 161
cgccgcgaat ggccctttga ctacccccccc ccccaagccg cccttagag atcgccgc     58

<210> SEQ ID NO 162
<211> LENGTH: 58
<212> TYPE: DNA
<213> ORGANISM: artificial sequence
<220> FEATURE:
<223> OTHER INFORMATION: oligonucleotide

<400> SEQUENCE: 162
gcgcggctta cctttgtact gatgatttat atacttcggc atacgttctc tagcggcg      58

<210> SEQ ID NO 163
<211> LENGTH: 58
<212> TYPE: DNA
<213> ORGANISM: artificial sequence
<220> FEATURE:
<223> OTHER INFORMATION: oligonucleotide

<400> SEQUENCE: 163
cgccgcatct cttttccccg gcttccccccc ccccgtagtc tttcccccat tcccgcgc   58

<210> SEQ ID NO 164
<211> LENGTH: 54
<212> TYPE: DNA
<213> ORGANISM: artificial sequence
<220> FEATURE:
<223> OTHER INFORMATION: oligonucleotide

<400> SEQUENCE: 164
gaatctagta tgattggagc aattgcttct cctgtagtta gagatttgca aacc          54

<210> SEQ ID NO 165
<211> LENGTH: 54
<212> TYPE: DNA
<213> ORGANISM: artificial sequence
<220> FEATURE:
<223> OTHER INFORMATION: oligonucleotide

<400> SEQUENCE: 165
ggtttgcaaa tctctaacta caggagaagc aattgctcca atcatactag attc          54

<210> SEQ ID NO 166
<211> LENGTH: 90
<212> TYPE: DNA
<213> ORGANISM: artificial sequence
<220> FEATURE:
<223> OTHER INFORMATION: oligonucleotide

<400> SEQUENCE: 166
gcggtaattt taatgagata acgagaacac gtatgccgaa gtatataaat catcagtaca    60
aaggtaagaa tcacagtaaa cagcgcgcgg                                    90

<210> SEQ ID NO 167
<211> LENGTH: 90
<212> TYPE: DNA
<213> ORGANISM: artificial sequence
<220> FEATURE:
<223> OTHER INFORMATION: oligonucleotide

<400> SEQUENCE: 167
ccgcgcgctg tttactgtga ttcttacctt tgtactgatg atttatatac ttcggcatac    60
gtgttctcgt tatctcatta aaattaccgc                                    90

<210> SEQ ID NO 168
<211> LENGTH: 47
<212> TYPE: DNA
<213> ORGANISM: artificial sequence
<220> FEATURE:
<223> OTHER INFORMATION: oligonucleotide

<400> SEQUENCE: 168
ctgctatata ttcaggcggt gccgcttat ttttaatcgg tgcatgg                   47

<210> SEQ ID NO 169
<211> LENGTH: 47
<212> TYPE: DNA
<213> ORGANISM: artificial sequence
<220> FEATURE:
<223> OTHER INFORMATION: oligonucleotide

<400> SEQUENCE: 169
ccatgcaccg attaaaaata aagcggcacc gcctgaatat atagcag                  47

<210> SEQ ID NO 170
<211> LENGTH: 38
<212> TYPE: DNA
<213> ORGANISM: artificial sequence
<220> FEATURE:
<223> OTHER INFORMATION: oligonucleotide

<400> SEQUENCE: 170
ggcgaatttt caggttcagg tataaaaaca agcttagg                            38

<210> SEQ ID NO 171
<211> LENGTH: 38
<212> TYPE: DNA
<213> ORGANISM: artificial sequence
<220> FEATURE:
<223> OTHER INFORMATION: oligonucleotide

<400> SEQUENCE: 171

```
cctaagcttg tttttatacc tgaacctgaa aattcgcc                               38
```

<210> SEQ ID NO 172
<211> LENGTH: 25
<212> TYPE: DNA
<213> ORGANISM: artificial sequence
<220> FEATURE:
<223> OTHER INFORMATION: oligonucleotide

<400> SEQUENCE: 172

```
tgataaatat aatactctaa cgctg                                            25
```

<210> SEQ ID NO 173
<211> LENGTH: 25
<212> TYPE: DNA
<213> ORGANISM: artificial sequence
<220> FEATURE:
<223> OTHER INFORMATION: oligonucleotide

<400> SEQUENCE: 173

```
acagcgttag agtattatat ttatc                                            25
```

<210> SEQ ID NO 174
<211> LENGTH: 25
<212> TYPE: DNA
<213> ORGANISM: artificial sequence
<220> FEATURE:
<223> OTHER INFORMATION: oligonucleotide

<400> SEQUENCE: 174

```
aataacatct ttcatttttc catcc                                            25
```

<210> SEQ ID NO 175
<211> LENGTH: 24
<212> TYPE: DNA
<213> ORGANISM: artificial sequence
<220> FEATURE:
<223> OTHER INFORMATION: oligonucleotide

<400> SEQUENCE: 175

```
gggatggaaa aatgaaagat gtta                                             24
```

<210> SEQ ID NO 176
<211> LENGTH: 43
<212> TYPE: DNA
<213> ORGANISM: artificial sequence
<220> FEATURE:
<223> OTHER INFORMATION: oligonucleotide

<400> SEQUENCE: 176

```
cttcggggtg ggtatcgatc agagaccttt gagcttccga gac                        43
```

<210> SEQ ID NO 177
<211> LENGTH: 43
<212> TYPE: DNA
<213> ORGANISM: artificial sequence
<220> FEATURE:
<223> OTHER INFORMATION: oligonucleotide

<400> SEQUENCE: 177

```
aaaaggggac gagaactaaa tctaacaaca ctctaaaaaa ttg                        43
```

<210> SEQ ID NO 178
<211> LENGTH: 55
<212> TYPE: RNA
<213> ORGANISM: artificial sequence
<220> FEATURE:
<223> OTHER INFORMATION: RNA oligonucleotide

<400> SEQUENCE: 178
ugauucuuac cuuuguacug augauuuaua uacuucggca uacguucucu aaaua      55

<210> SEQ ID NO 179
<211> LENGTH: 55
<212> TYPE: RNA
<213> ORGANISM: artificial sequence
<220> FEATURE:
<223> OTHER INFORMATION: RNA oligonucleotide

<400> SEQUENCE: 179
gcuguuaagu uacucgagca caucagugau agccuuauuc ccgcugugcc uauac      55

<210> SEQ ID NO 180
<211> LENGTH: 55
<212> TYPE: RNA
<213> ORGANISM: artificial sequence
<220> FEATURE:
<223> OTHER INFORMATION: RNA oligonucleotide

<400> SEQUENCE: 180
ugauucuuac cuuuguacug augauuuaua uacuucggca uacguguucu cguua      55

<210> SEQ ID NO 181
<211> LENGTH: 10
<212> TYPE: RNA
<213> ORGANISM: artificial sequence
<220> FEATURE:
<223> OTHER INFORMATION: RNA oligonucleotide

<400> SEQUENCE: 181
guuuacugug                                                        10

<210> SEQ ID NO 182
<211> LENGTH: 10
<212> TYPE: RNA
<213> ORGANISM: artificial sequence
<220> FEATURE:
<223> OTHER INFORMATION: RNA oligonucleotide

<400> SEQUENCE: 182
uuaaugagau                                                        10

<210> SEQ ID NO 183
<211> LENGTH: 34
<212> TYPE: DNA
<213> ORGANISM: artificial sequence
<220> FEATURE:
<223> OTHER INFORMATION: spacer sequence

<400> SEQUENCE: 183
gtttttcata gttaatcaat cccttttctt tttt                             34

<210> SEQ ID NO 184
<211> LENGTH: 44
<212> TYPE: RNA
<213> ORGANISM: artificial sequence
<220> FEATURE:
<223> OTHER INFORMATION: crRNA

<400> SEQUENCE: 184
acgagaacuu aaaucuuuga uugcucuuag cucuaguuau guau                  44

<210> SEQ ID NO 185
<211> LENGTH: 60
<212> TYPE: DNA
<213> ORGANISM: artificial sequence
<220> FEATURE:
<223> OTHER INFORMATION: Target

<400> SEQUENCE: 185
aaacatacgc acataactcg agctaagagc aatcaaaggt ttacagttgt tgaggcagag    60

<210> SEQ ID NO 186
<211> LENGTH: 60
<212> TYPE: DNA
<213> ORGANISM: artificial sequence
<220> FEATURE:
<223> OTHER INFORMATION: Target

<400> SEQUENCE: 186
ctctgcctca acaactgtaa acctttgatt gctcttagct cgagttatgt gcgtatgttt    60

<210> SEQ ID NO 187
<211> LENGTH: 45
<212> TYPE: DNA
<213> ORGANISM: artificial sequence
<220> FEATURE:
<223> OTHER INFORMATION: Promoter

<400> SEQUENCE: 187
tacactttta ttatactatg aaaaatcgta attgcaaccc ttaaa                    45

<210> SEQ ID NO 188
<211> LENGTH: 45
<212> TYPE: DNA
<213> ORGANISM: artificial sequence
<220> FEATURE:
<223> OTHER INFORMATION: Promoter

<400> SEQUENCE: 188
tttaagggtt gcaattacga tttttcatag tataataaaa gtgta                    45

<210> SEQ ID NO 189
<211> LENGTH: 41
<212> TYPE: RNA
<213> ORGANISM: artificial sequence
<220> FEATURE:
<223> OTHER INFORMATION: spc1 crRNA

<400> SEQUENCE: 189
acgagaacac guaugccgaa guauauaaau caucaguaca a                        41

<210> SEQ ID NO 190
<211> LENGTH: 60
<212> TYPE: DNA
<213> ORGANISM: artificial sequence
<220> FEATURE:
<223> OTHER INFORMATION: gp43 target region (coding strand sequence)

<400> SEQUENCE: 190
gtgacttcac acaagataac attattgatt tagaggcatt acttgaagat gacgaattag    60

<210> SEQ ID NO 191
<211> LENGTH: 45
<212> TYPE: DNA
<213> ORGANISM: artificial sequence
<220> FEATURE:
<223> OTHER INFORMATION: nes target bottom strand

```
<400> SEQUENCE: 191
tttagagaac gtatgccgaa gtatataaat catcagtaca aaggt            45

<210> SEQ ID NO 192
<211> LENGTH: 45
<212> TYPE: DNA
<213> ORGANISM: artificial sequence
<220> FEATURE:
<223> OTHER INFORMATION: target

<400> SEQUENCE: 192
acctttgtac tgatgattta tatacttcgg catacgttct ctaaa            45
```

COMPOSITIONS AND METHODS FOR TRANSCRIPTION-BASED CRISPR-CAS DNA EDITING

CROSS REFERENCE TO RELATED APPLICATIONS

This application claims priority to U.S. provisional patent application No. 62/034,684, filed Aug. 7, 2014, the disclosure of which is incorporated herein by reference.

FIELD OF THE DISCLOSURE

The present disclosure is related to compositions and methods for selectively modifying transcribed DNA targets.

SEQUENCE LISTING

The instant application contains a Sequence Listing which has been submitted electronically in ASCII format and is hereby incorporated by reference in its entirety. Said ASCII copy, created on Feb. 3, 2017, is titled "CRISPR_Transcription_PCT.txt" and is 64,964 bytes in size.

BACKGROUND OF THE DISCLOSURE

There is an ongoing and unmet need for compositions and methods that can be used for editing of chromosomes and extra-chromosmal elements in a sequence specific, conditional manner. The present disclosure meets these and other needs.

BRIEF SUMMARY OF THE DISCLOSURE

The present disclosure provides compositions and methods for selectively modifying DNA targets comprising spacer sequences, wherein the modifications are made by modified clustered regularly interspaced short palindromic repeats (CRISPR) systems, and wherein the DNA targets are transcribed as a prerequisite to the modification.

In one aspect the disclosure includes a method for modification of a DNA sequence in a cell comprising introducing into the cell a recombinant vector comprising a clustered regularly interspaced short palindromic repeats (CRISPR) system. The CRISPR system comprises nucleotide sequences encoding i) a CRISPR RNA (crRNA) targeted to a DNA sequence in the cell that is operatively linked to a promoter, and ii) CRISPR-associated enzymes (Cas) 10, Cas6, and a Csm protein selected from the group consisting of Csm2, Csm3, Csm4, Csm5 and Csm6, and combinations thereof. The method functions such that the Cas10 modifies the DNA sequence only during transcription of the DNA sequence that is operatively linked to the promoter. In embodiments, the modification is a conditional modification of the DNA such that transcription of the DNA from the promoter is not constitutive transcription. For example, in certain embodiments, the promoter is an inducible promoter. In embodiments, the method comprises inducing transcription from the promoter such that the DNA sequence is modified by the Cas10. In embodiments, modification of the DNA comprises editing the DNA, and/or cleaving the DNA, and/or linearizing the DNA in the case of a circular DNA target, and/or nicking one strand of a dsDNA. In embodiments, modifying the target comprises exonucleolytic degradation of one or more DNA strand. In embodiments, modification of the DNA confers a change in phenotype of the cell, such as a change in morphology, growth rate, expression of a detectable or selectable marker, or the modification is lethal to the cell. In embodiments, the DNA sequence that is transcribed is present on a chromosome, or is present on an extrachromosomal element, including but not limited to a plasmid. In embodiments, the extrachromosomal element does not comprise a temperature sensitive (Ts) origin of replication, or does not comprise Ts promoter. In certain aspects, the disclosure includes transcription of the DNA target, editing of the target, and identification of the cell and/or the DNA target that was edited. Thus, in embodiments, the disclosure includes identification of one or more cells wherein the modification occurs, and/or identification of one or more cells in which the modification does not occur. In embodiments, identification of target sequences that are edited or are not edited when such cells comprise a CRISPR system of this disclosure provides an approach for transcriptional surveillance.

In another aspect the disclosure includes a recombinant vector suitable for use in embodiments of the disclosure. In general, the recombinant vector comprises a CRISPR system which includes i) a crRNA targeted to a DNA sequence that is operatively linked to a promoter; and ii) a sequence encoding a Cas10 enzyme, a Cas6 enzyme, and a Csm enzyme selected from the group consisting of a Csm2 enzyme, a Csm3 enzyme, a Csm4 enzyme, a Csm5 enzyme and a Csm6 enzyme, and combinations thereof. The disclosure includes methods of making such recombinant vectors, methods of introducing them into cells for maintenance or propagation of the vector or for editing targets in the cells, compositions comprising the recombinant vectors, eukaryotic and prokaryotic cells which include the recombinant vector, and kits comprising the recombinant vectors. In embodiments, a cell that comprises the recombinant vector will also comprise a target sequence that is operatively linked to a promoter, which may or may not be an inducible promoter. In embodiments, the target sequence in the cell that comprises the recombinant vector is present on a chromosomal or an extra-chromosomal element, including but not limited to a plasmid.

The present disclosure demonstrates, among other aspects, that transcription across the targets of the *Staphylococcus epidermidis* type III-A CRISPR-Cas system results in the cleavage of the target DNA and its transcripts, mediated by independent active sites within the Cas10-Csm ribonucleoprotein effector complex. Immunity against plasmids and DNA viruses requires DNA but not RNA cleavage activity. Thus, the disclosure encompasses a highly versatile mechanism of CRISPR immunity that can defend microorganisms against diverse DNA and RNA invaders, and is adaptable for a wide variety of approaches to selectively modifying DNA targets in vitro and in vivo.

Figure 9:
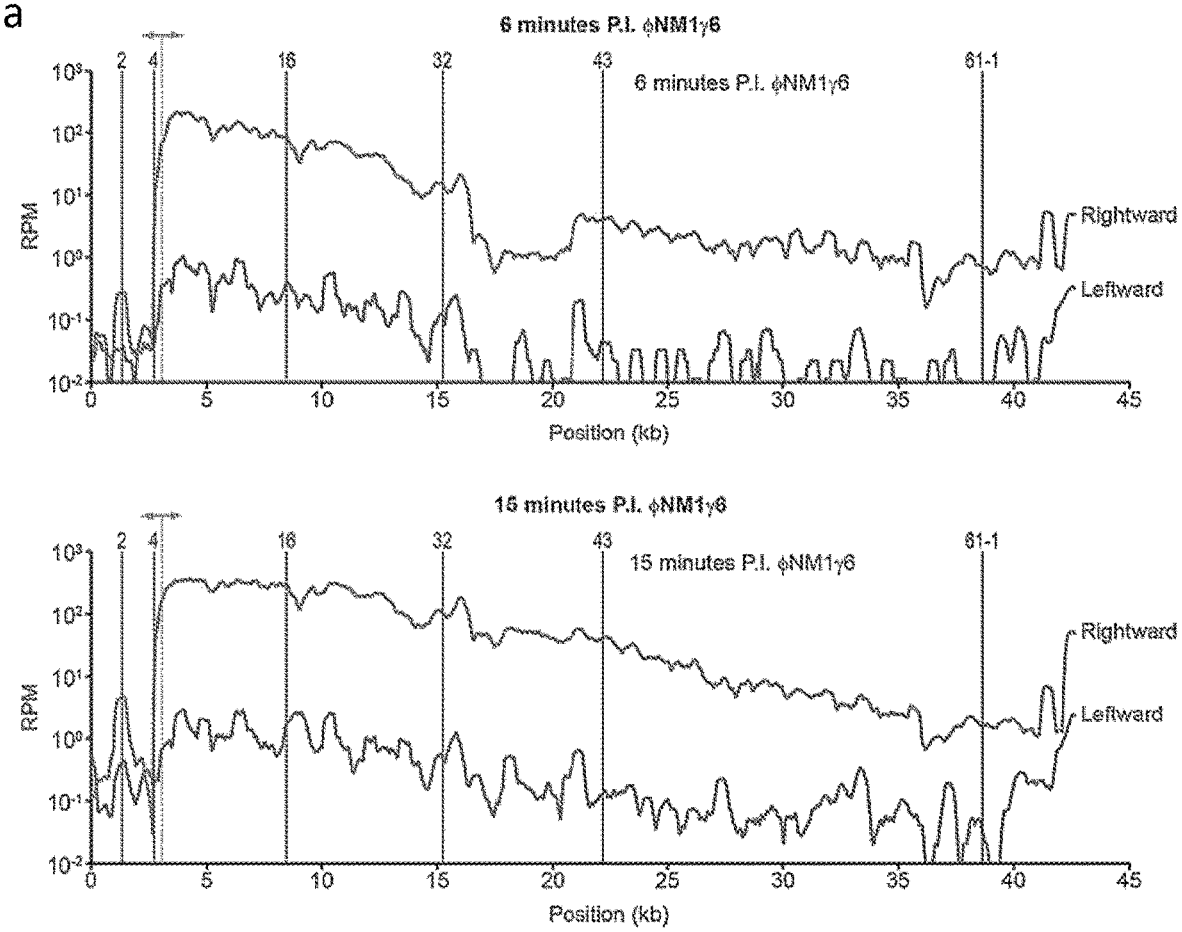
Figure 9:
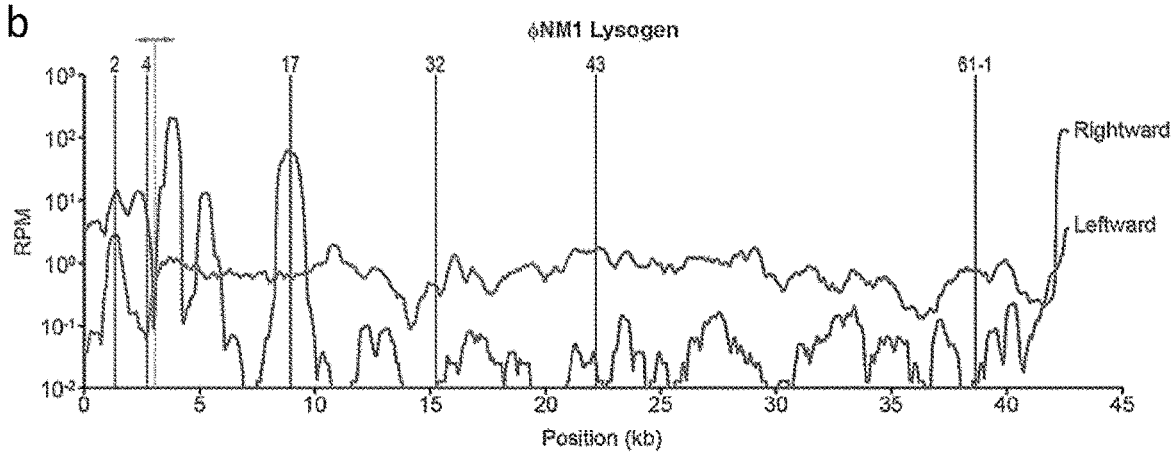

FIG. 9. Visualization of transcription profiles for ΦNM1γ6 and the ΦNM1 prophage. Graphical presentation is the same as in FIG. 7. a, ΦNM1γ6 transcription profiles 6 and 15 min post infection (MOI 20). Comparison with ΦNM1 samples at equivalent time points (FIG. 7) reveals a marked decrease in leftward transcription to the left of the central promoter region. We calculated the fold-change in RPM between ΦNM1 and ΦNM1γ6 samples 15 min post infection. Leftward expression within the region bounded by the start of the genome and the central promoter was reduced 32-fold, while only a 4-fold reduction in leftward expression was observed overall. Meanwhile, rightward expression was reduced 4-fold both overall and in this region. This suggests an ~8-fold net reduction in leftward transcription originating from the central promoter. b, ΦNM1 prophage transcription profiles. Strong leftward transcription originates from the central promoter and a few upstream regions which are presumed to be important for lysogenic maintenance. Rightward transcription was weaker than leftward transcription as expected, but not absent. Given the strength of rightward transcription observed during the lytic cycle (FIG. 7), however, this transcription may originate from a subpopulation of cells undergoing prophage induction, rather than the stable lysogen majority.

Figure 10:
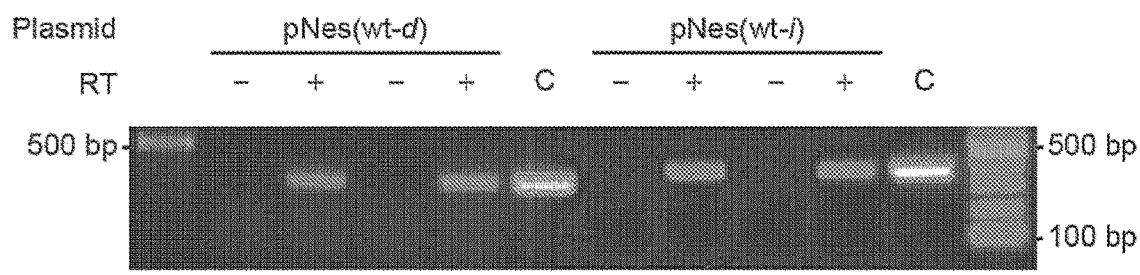

FIG. 10. Detection of transcription across target insertions for the pNes(wt-d) and pNes(wt-i) plasmids. For each target plasmid (ref. 24), reverse transcription was performed in both directions with DNase-treated total RNA from RN4220 cells harboring the indicated plasmids, using either forward or reverse primers for cDNA synthesis in two separate reactions. PCR was performed on cDNA products, or plasmid DNA templates for control (C) lanes. +/− indicate the presence or absence of reverse transcriptase enzyme in the RT reaction mixture used for PCR. 500 bp and 100 bp size markers are indicated.

Figure 3:
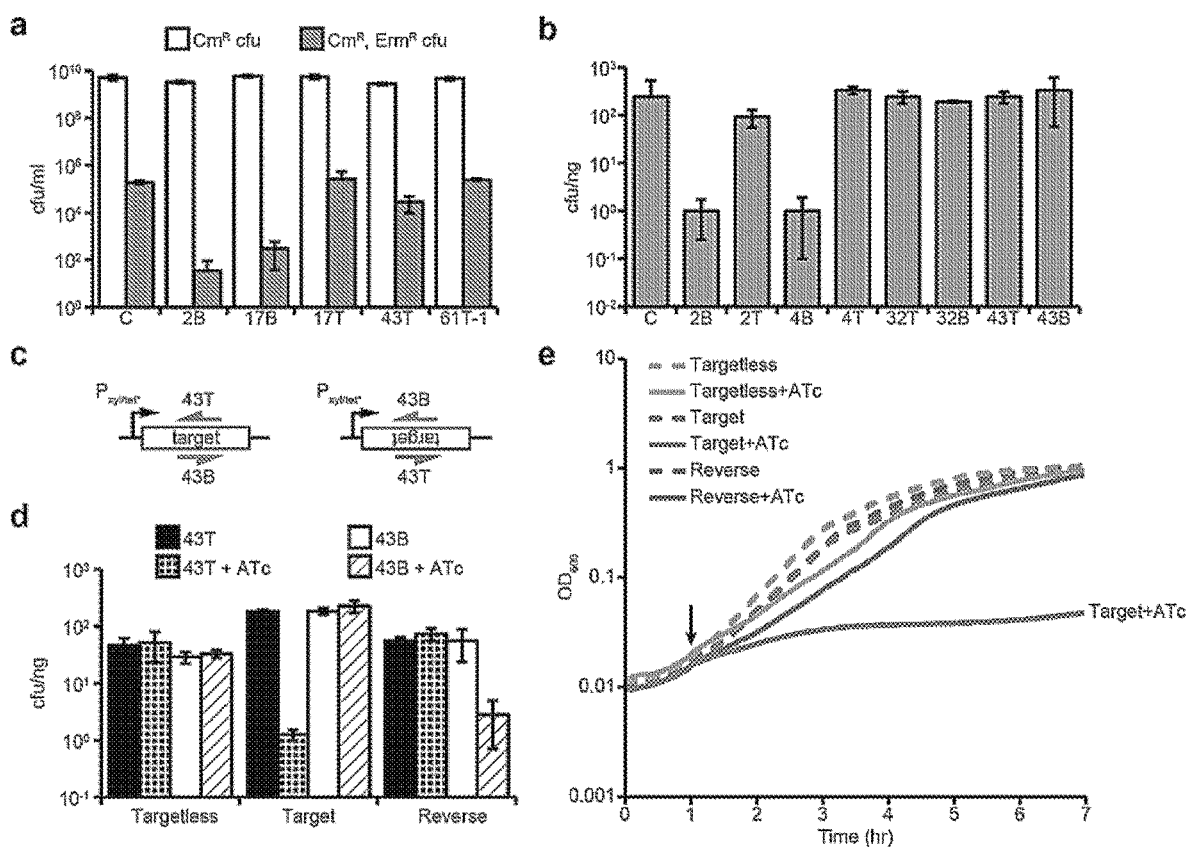
FIG. 3. Conditional tolerance is achieved via transcription-dependent CRISPR-Cas targeting. a, ΦNM1-Erm^R lysogenization for additional spacers. C, pGG3 non-targeting control. b, Transformation of ΦNM1-lysogenic competent cells with CRISPR-Cas plasmids containing different spacers (transformation efficiency is measured as cfu/ng of plasmid DNA). C, pGG3 non-targeting control. c, Integration of the 43T/B ΦNM1 target region into the chromosome of S. aureus. Target sequences (inserted in both forward and reverse orientations) are under the control of the tetracycline-inducible promoter $P_{xyl/tet*}$. The 43T/B crRNAs are shown annealing to either the top or bottom strands. d, Transformation of both strains shown in c, as well as an isogenic control strain lacking the target insertion, with CRISPR-Cas plasmids containing spacers 43T or 43B. Transformants were plated on selective plates with or without anhydrotetracycline (ATc) for induction of the $P_{xyl/tet*}$ promoter. e, Growth curve of strains shown in d expressing the spacer 43T CRISPR-Cas system, in the presence or absence of ATc addition at the indicated timepoint (black arrow). Error bars: mean±s.d.
Figure 11:
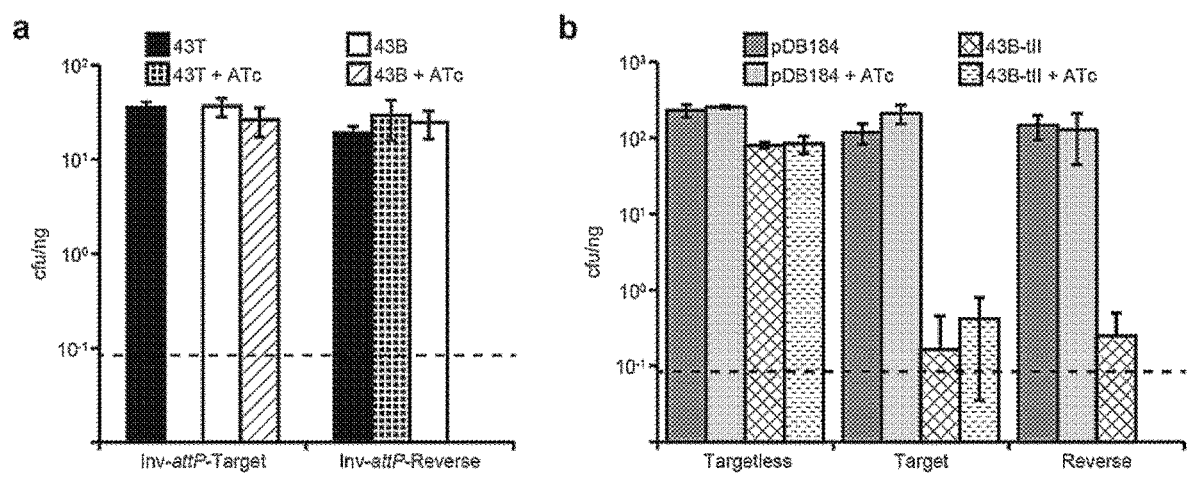

FIG. 11. Reverse CRISPR-immunity assays using inverted chromosomal target insertions or type II CRISPR-Cas plasmids. Values represent the average transformation efficiency of three transformations in colony forming units (cfu) per microgram (g) of plasmid DNA transformed. ATc, anhydrotetracycline at 0.5 μg/ml. Dotted lines represent the limit of detection for these assays. a, Reverse CRISPR-immunity assays using inverted target vector insertions and spacer 43T or 43B plasmid DNA. Inversion of the attP motif ('Inv-attP-') for forward and reverse insertion vectors causes integration in the opposite orientation relative to the chromosomal origin of replication. b, Reverse CRISPR-immunity assays using type II-A CRISPR plasmid DNA to transform strains from FIG. 3b. The pDB184 parent vector serves as a non-targeting control.

Figure 12:
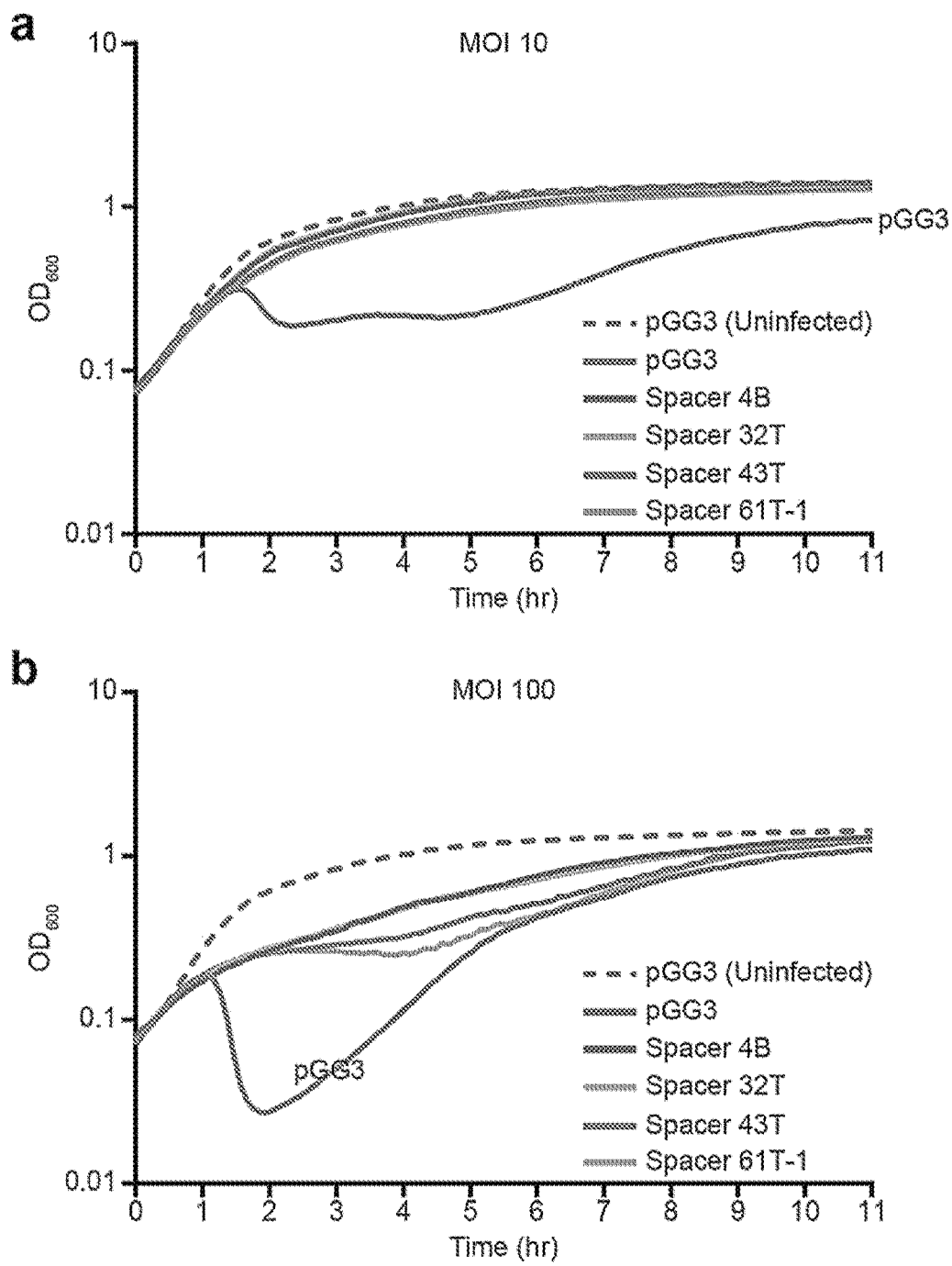

FIG. 12. Infection with ΦNM1 in liquid culture. Growth curves of RN4220 cells harboring the indicated CRISPR plasmids were infected at time zero with ΦNM1 at a MOI of 10 (a) or 100 (b). Growth of uninfected RN4220/pGG3 cultures is also shown.

Figure 13:
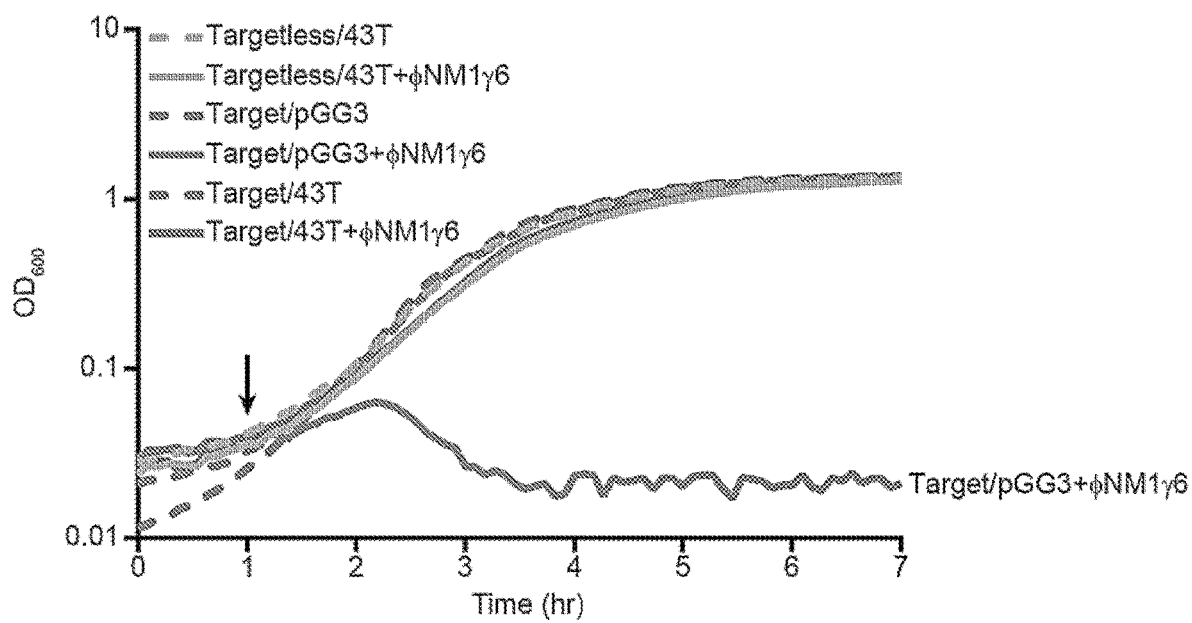

FIG. 13. Immunity to ΦNM1γ6 in liquid culture is unaffected by the presence of a tolerated chromosomal target. Growth curves of the indicated chromosomal insertion strains from FIG. 3 harboring either spacer 43T or pGG3 CRISPR plasmids, in the absence (dotted lines) or presence (solid lines) of ΦNM1γ6 addition at a MOI of 10. Black arrow denotes the time of phage addition; no ATc induction is utilized in this assay. The presence of a chromosomal target for spacer 43T has no discernable effect on culture growth during spacer 43T-mediated immunity to ΦNM1γ6.

Figure 14:
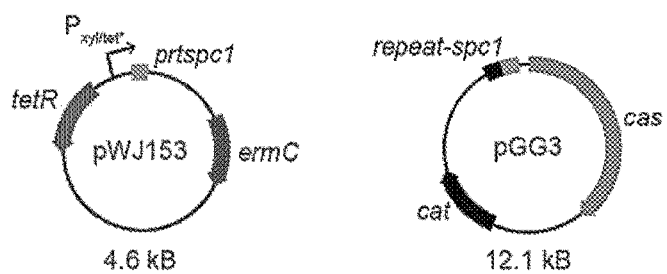
Figure 14:
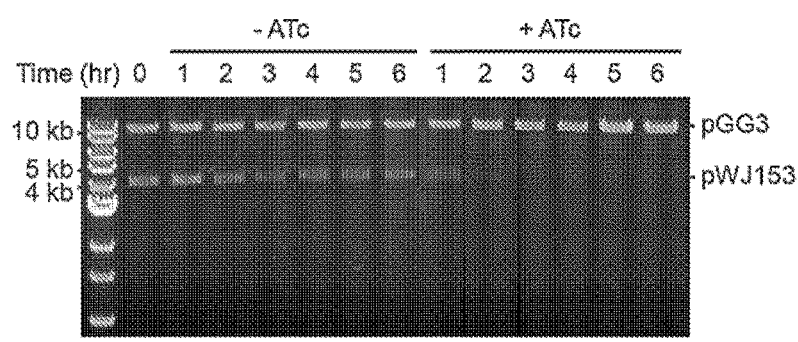
Figure 14:
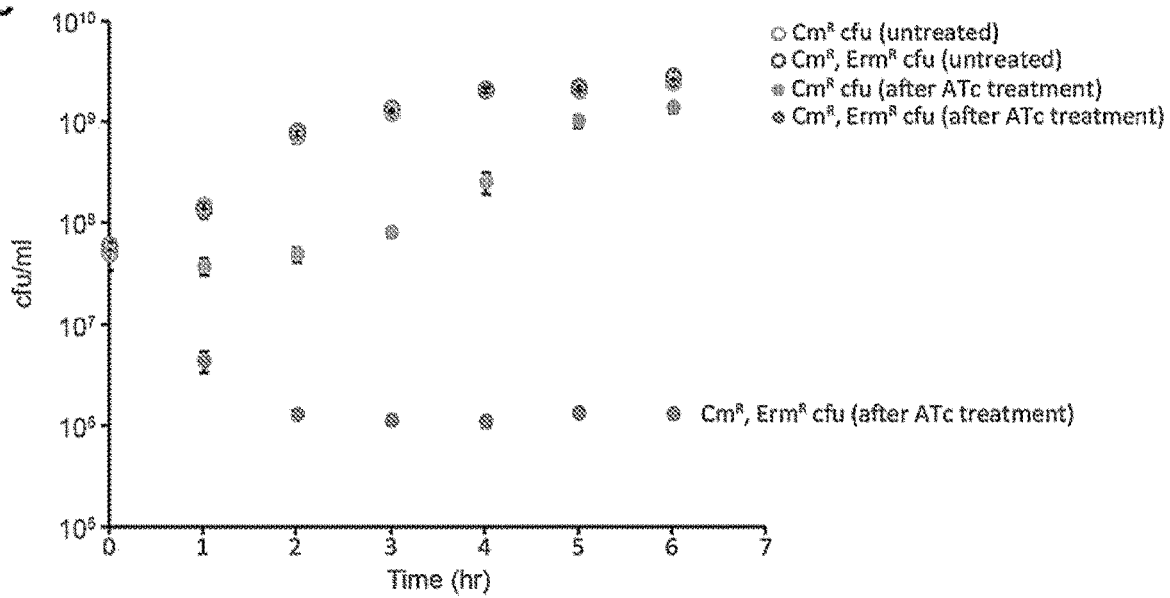

FIG. 14. Inducible curing of a target plasmid. a, Schematic diagram of plasmids utilized in the plasmid curing experiment. The pGG3 CRISPR plasmid harbors a single spacer ("spc1") targeting a sequence ("prtspc1") inserted downstream of the P$_{xyl/tet*}$ inducible promoter in pWJ153. b, Agarose gel electrophoresis of linearized plasmid DNA purified from both anhydrotetracycline-treated (+ATc) and untreated (−ATc) cultures at the indicated timepoints. 10 kb, 5 kb, and 4 kb size markers are indicated. c, Colony forming units (cfu) recovered from cultures analyzed in panel (b) at each time point. Cells were plated with selection for either Cm$^R$ cfu (green) or Cm$^R$, Erm$^R$ cfu (blue). Targeting of the pWJ153 plasmid via induction with ATc (filled circles) is accompanied by a severe drop in erythromycin-resistant cfu relative to untreated cultures (open circles).

Figure 15:
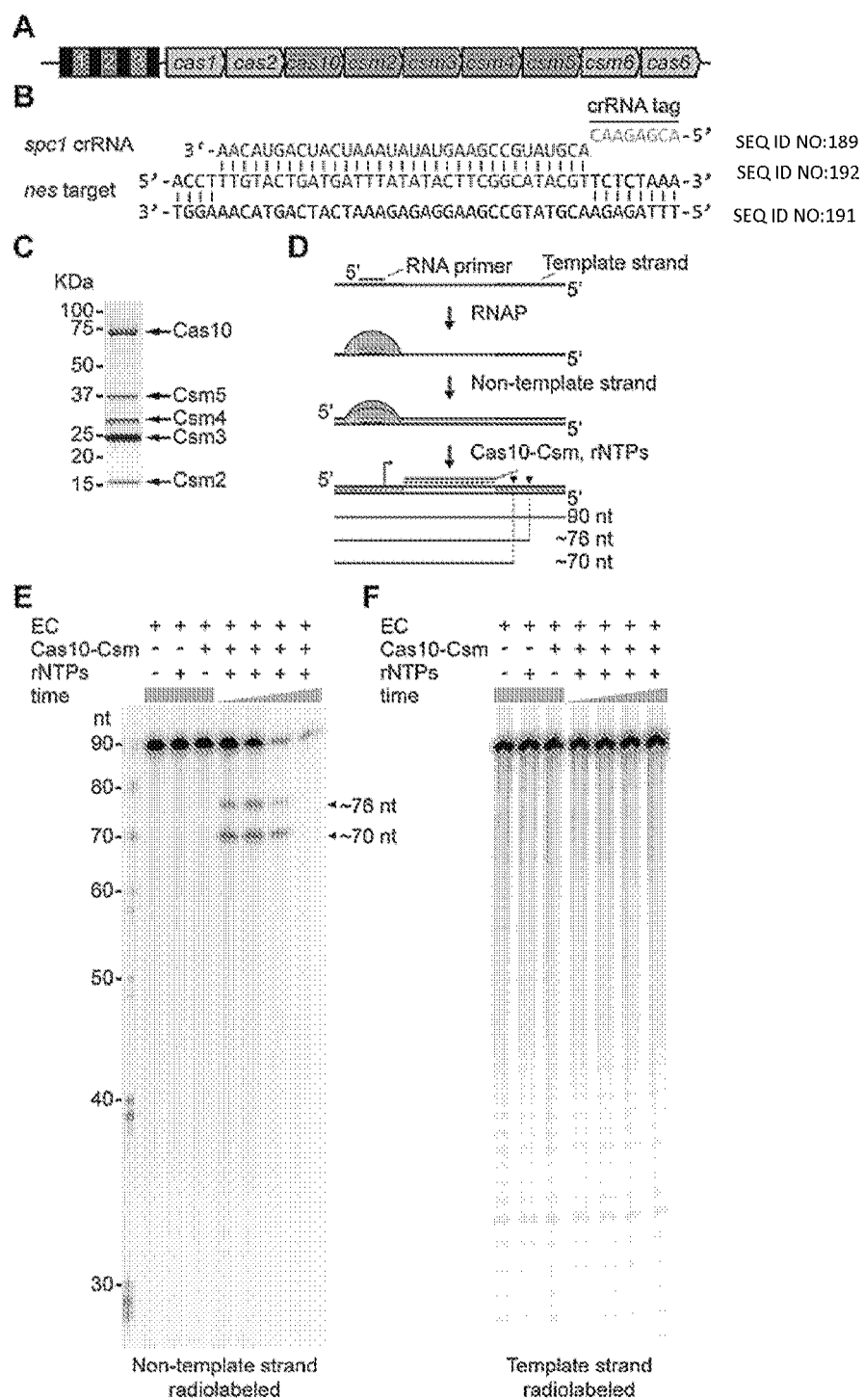

FIG. 15. crRNA-guided co-transcriptional DNA cleavage by the S. epidermidis Cas10-Csm complex. (A) S. epidermidis RP62a carries a CRISPR-Cas locus that harbors four repeats (black boxes), three spacers (colored boxes) and nine cas/csm genes, five of which (highlighted in blue) encode for the Cas10-Csm ribonucleoprotein complex. (B) The first spacer sequence (spc1) generates a mature crRNA that targets a complementary sequence in the nickase gene (nes) present in most staphylococcal conjugative plasmids (green). The most abundant mature crRNA species contains 33 nt of spacer sequence as well as 8 nt of repeat sequences at its 5' end, known as the crRNA tag, as labeled. (C) SDS-PAGE of the Cas10-Csm complex purified from E. coli. (D) Schematic of the co-transcriptional DNA cleavage assay of a dsDNA substrate containing the nes target. Arrowheads indicate the approximate cleavage site detected in panel E. The circle identifies the radiolabeled 5' end of substrate and products. (E, F) Denaturing PAGE and autoradiography of the products of two co-transcriptional dsDNA cleavage assays differing in the location of the radioactive label: E, non-template strand; F, template strand. Cleavage products were collected at 30, 60, 90 and 120 minutes. Reactions in which each of the components of the assay were omitted in a 120-minute assay are shown as controls.

Figure 16:
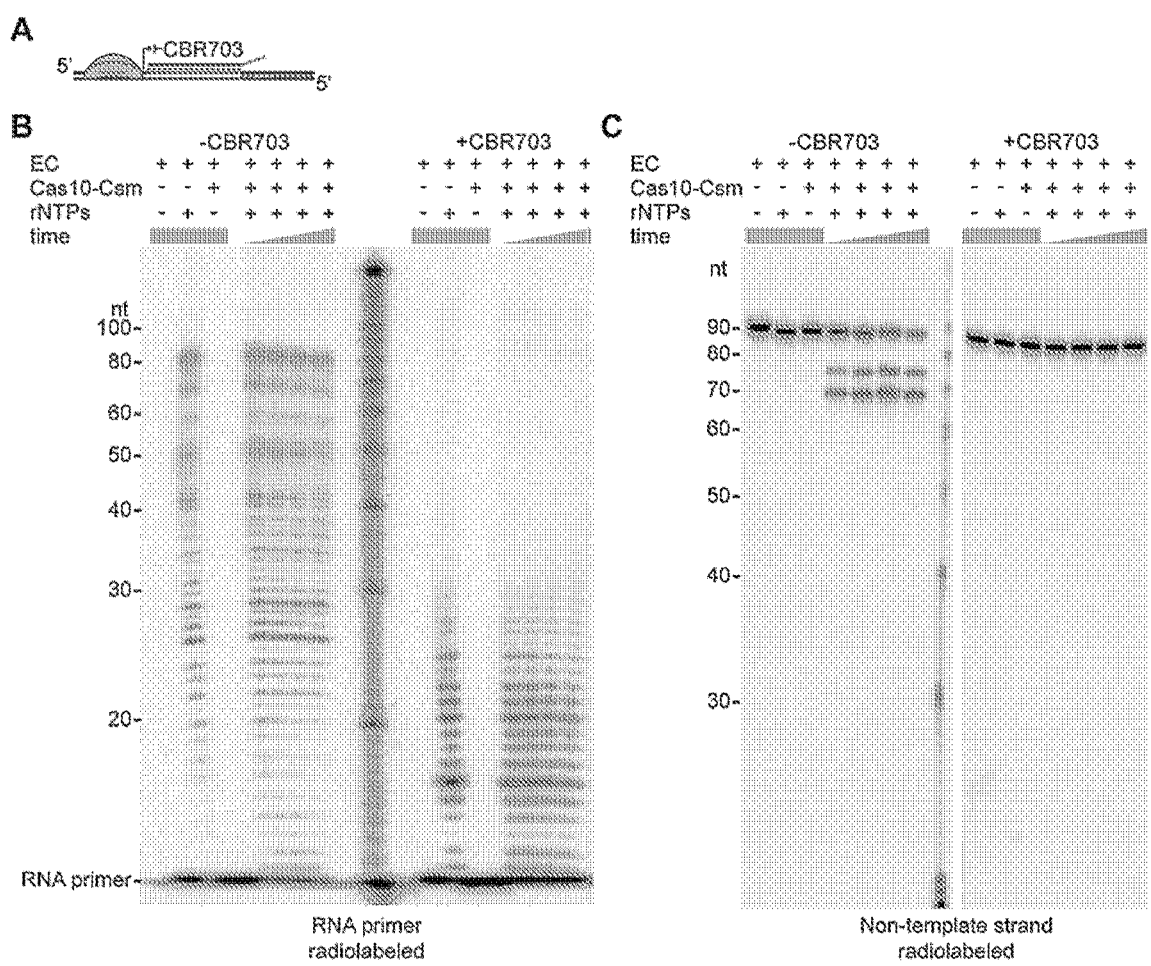

FIG. 16. RNAP elongation is required for Cas10-Csm target cleavage. (A) The small molecule CBR703 inhibits RNAP elongation and was tested in our DNA cleavage assay to corroborate the transcription requirement for cleavage. (B) CBR703 inhibits transcription elongation. Using a radiolabeled RNA primer we measured transcription elongation in different conditions in the presence (1 µM) or absence of CBR703. Extension products were collected at 30, 60, 90 and 120 minutes. Reactions in which each of the components of the assay were omitted in a 120-minute assay are shown as controls. (C) In vitro DNA cleavage assay using a radiolabeled non-template strand (as in FIG. 15E) in the presence (1 µM) or absence of CBR703. Reaction products were collected at 30, 60, 90 and 120 minutes. Reactions in which each of the components of the assay were omitted in a 120-minute assay are shown as controls.

Figure 17:
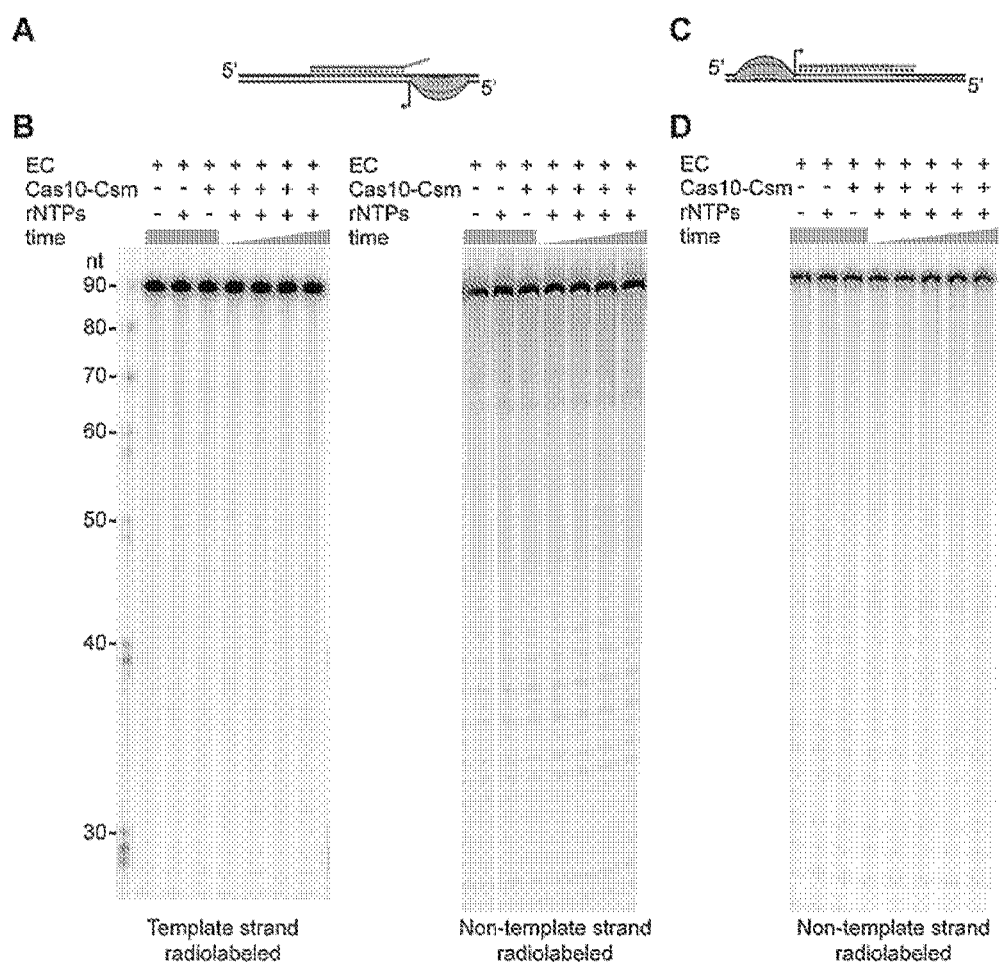

FIG. 17. In vitro cleavage reflects in vivo targeting. (A) Schematic of the substrate used to test for DNA cleavage in conditions where the crRNA matches the template strand. (B) In vitro DNA cleavage assay of the substrate show in panel A, with the radiolabel either in the template (left autoradiography) or non-template (right) strand. Reaction products were collected at 30, 60, 90 and 120 minutes. Reactions in which each of the components of the assay were omitted in a 120-minute assay are shown as controls. (C) Schematic of the "anti-tag" substrate in which the flanking sequence downstream on the nes target matches the 5' crRNA tag (light green), generating a full match between the crRNA and the DNA target. (D) In vitro DNA cleavage assay of the substrate show in panel C, with the non-template strand radiolabeled. Reaction products were collected at 30, 60, 90, 120 and 180 minutes. Reactions in which each of the components of the assay were omitted in a 120-minute assay are shown as controls.

Figure 18:
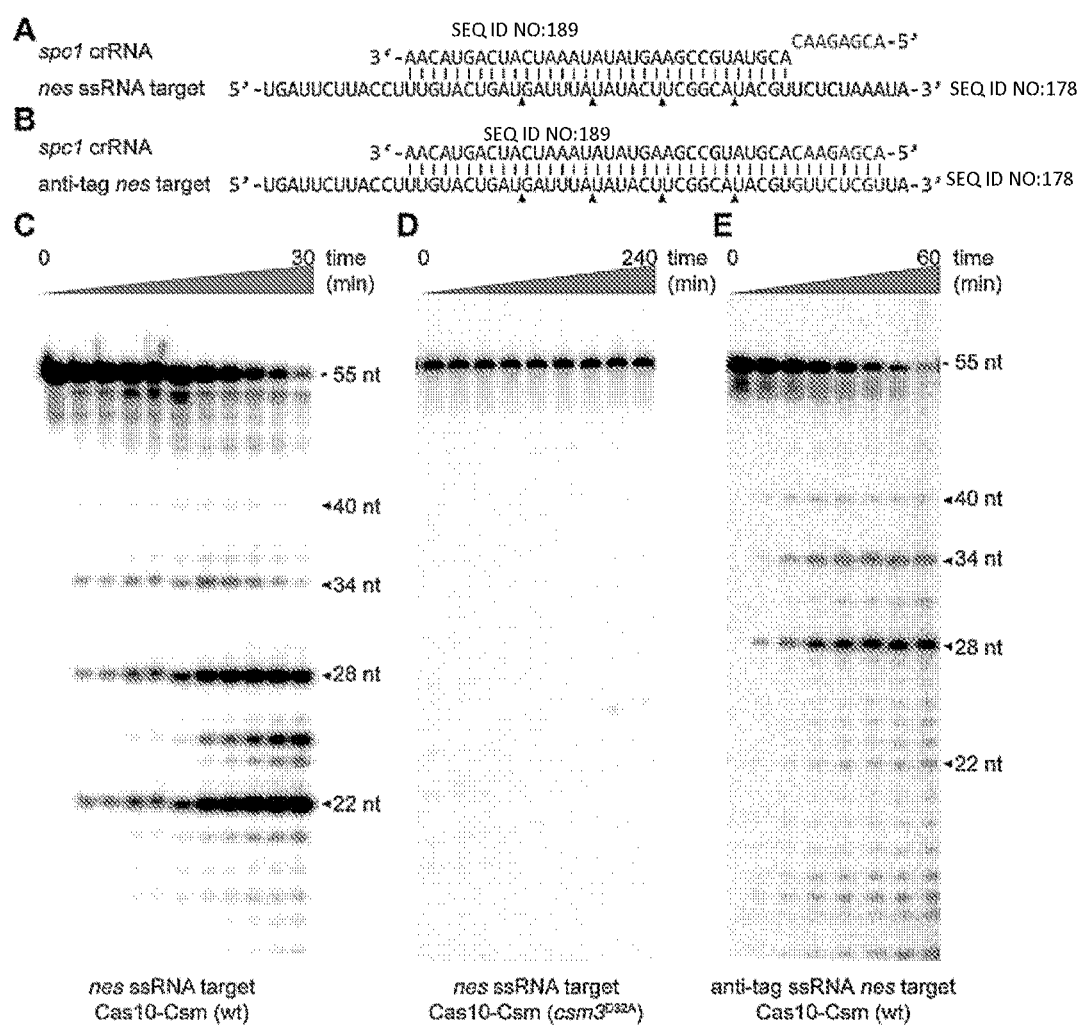

FIG. 18. crRNA-guided RNA cleavage of the *S. epidermidis* Cas10-Csm complex. (A) Base pair interaction between the nes crRNA and the 55-nt ssRNA target. Arrowheads showed the cleavage sites detected in panel C. (B) "Anti-tag" ssRNA substrate used to evaluate the effect of a full match between the crRNA guide and the ssRNA substrate. Arrowheads showed the cleavage sites detected in panel E. (C) In vitro ssRNA cleavage assay of the radiolabeled substrate show in panel A. Reaction products were collected at 0, 1, 2, 3, 4, 5, 7.5, 10, 15, 20 and 30 minutes, separated by denaturing PAGE and visualized by gel autoradiography. (D) Same assay as in panel C, using the mutant Cas10-Csm(Csm3$^{D32A}$) complex. Incubation times are 0, 5, 10, 20, 30, 60, 120, 180 ad 240 minutes. (E) Cleavage of the "anti-tag" ssRNA substrate shown in panel B; incubation times: 0, 5, 10, 15, 30 and 60 minutes.

Figure 19:
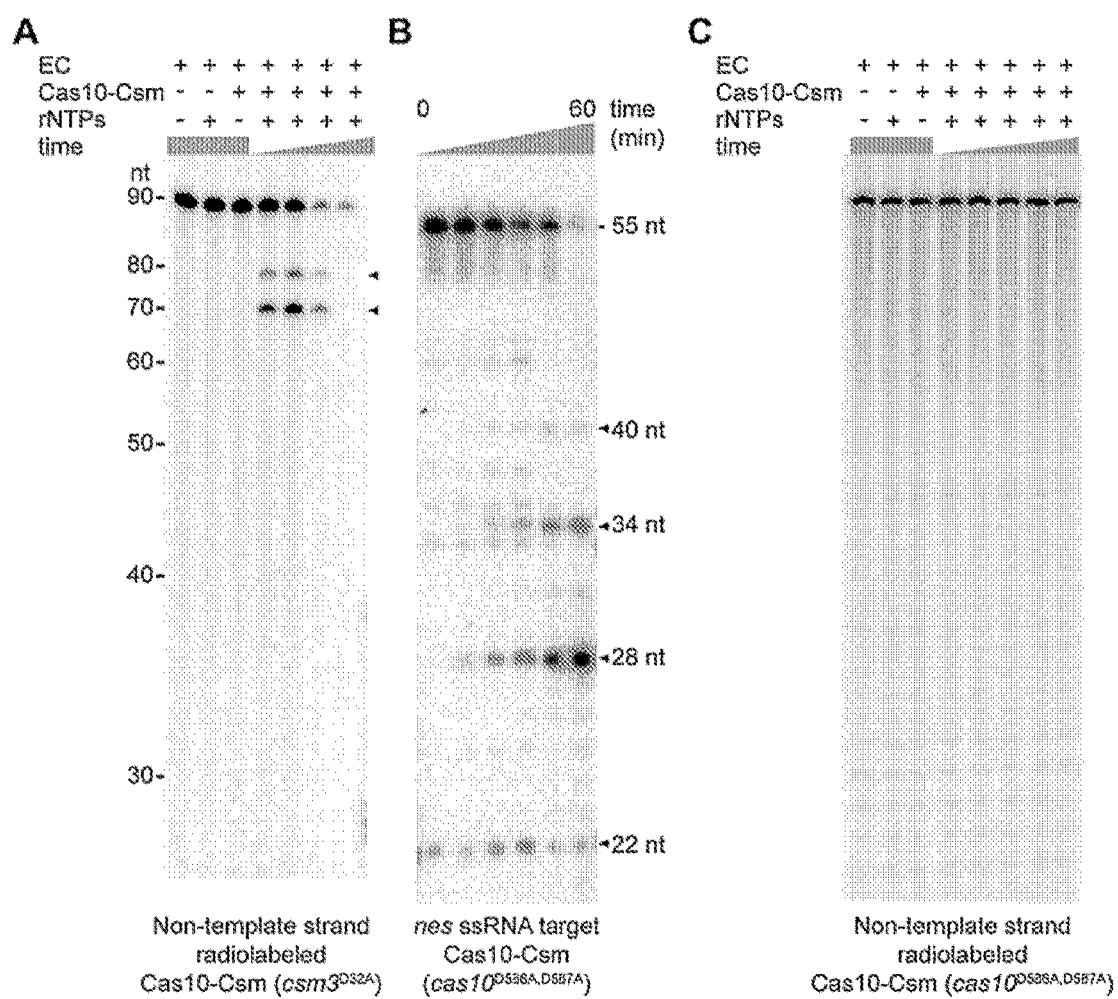

FIG. 19. The DNA and RNA cleavage activities of the Cas10-Csm complex are independent. (A) Same DNA cleavage assay shown in FIG. 15E using the Cas10-Csm (Csm3$^{D32A}$) complex. (B) Same ssRNA cleavage assay shown in FIG. 17C using the Cas10$^{D586A,D587A}$-Csm complex; incubation times: 0, 5, 10, 15, 30 and 60 minutes. (C) Same DNA cleavage assay shown in FIG. 15E using the Cas10$^{D586A,D587A}$-Csm complex. An extra time-point was taken at 180 minutes.

Figure 20:
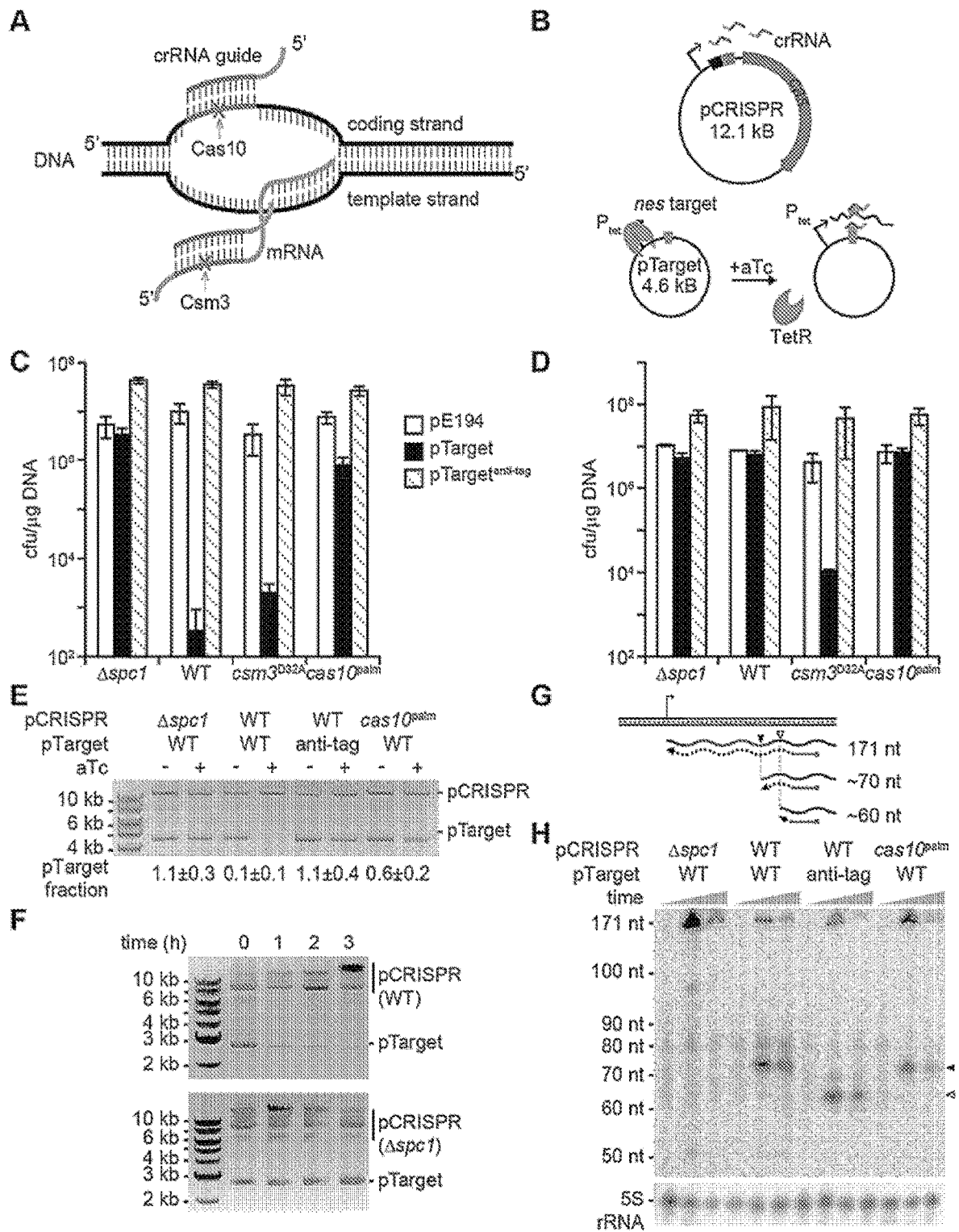

FIG. 20. CrRNA-guided co-transcriptional cleavage of plasmid DNA and its transcripts during type III-A CRISPR-Cas immunity. (A) Schematic of the dual crRNA-guided DNA and transcript RNA cleavage (shown as X). Target sequences are shown with base pairing between the crRNA guide and the DNA; the nuclease responsible for the cleavage of each nucleic acid is also indicated. (B) Inducible anti-plasmid CRISPR immunity assay. Staphylococci are transformed with two plasmids: pCRISPR carrying the type III-A CRISPR-Cas system of *S. epidermidis* and pTarget harboring the nes target under the control of the tetracycline-inducible promoter P$_{tet}$. In the absence of the anhydrotetracycine inducer (aTc) the tetracycline repressor (TetR) prevents nes transcription and therefore CRISPR immunity against pTarget. Addition of aTc triggers immunity, allowing following the fate of pTarget and its transcripts over time. (C) Transformation efficiencies of different pCRISPR plasmids (wild-type or the mutant variants Δspc1, cas10$^{palm}$ or csm3$^{D32A}$) into staphylococci harboring different target plasmids (pE194, pTarget and pTarget$^{anti-tag}$). Efficiency is calculated as the ratio of colony forming units (cfu) per µg of plasmid DNA transformed (mean±S.D. of three replicas). Colonies were enumerated in plates containing chloramphenicol and erythromycin for the selection of pCRISPR and pTarget, respectively, and aTc. (D) Same as panel C, but without supplementing plates with aTc. (E) pTarget transformants obtained in panel D were cultured in liquid media supplemented with chloramphenicol but without erythromycin. Cells were collected at the beginning of the exponential growth, before aTc was added (−), and after 10 hours of growth in the presence of the inducer (+). Plasmid DNA was extracted, digested with XhoI, separated by agarose gel electrophoresis and stained with ethidium bromide. The fraction of pTarget remaining after targeting relative to the pCRISPR control is shown at the bottom of the gel (mean±S.D. of three replicas). (F) Analysis of pTarget plasmid DNA at different times during type III-A CRISPR-Cas immunity (wild-type pCRISPR) or a non-targeting control (Δspc1 pCRISPR), without XhoI digestion. (G) Schematic of a primer extension assay designed to detect nes transcript cleavage during type III-A CRISPR-Cas immunity. A 5'-radiolabeled (red dot) primer (brown line) is used to initiate reverse transcription of the nes transcript, generating a 171 nt extension product in the absence of RNA cleavage, measured from the priming site to the +1 transcription start determined by the P$_{tet}$ promoter (arrow). The cleavage sites inferred from the results shown in panel H are indicated, approximately 70 and 60 nt from the priming site (black and grey arrowheads, respectively). (H) Primer extension analysis of the nes transcripts after addition of aTc in different targeting conditions. Times assayed: 0, 10 and 60 minutes. Arrowheads indicated the extension of the cleavage products.

Figure 21:
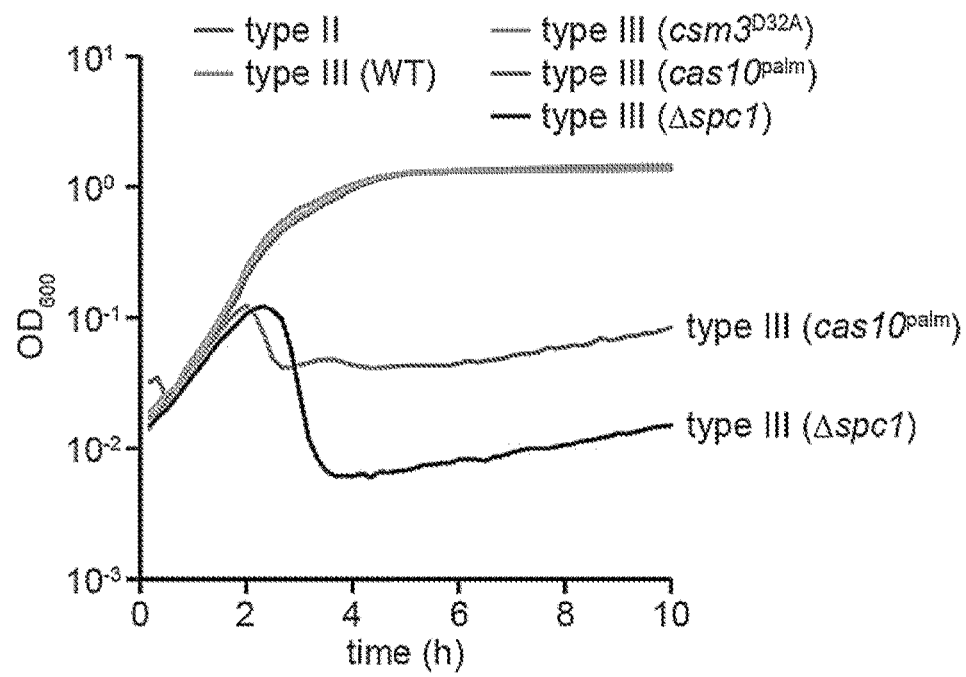

FIG. 21. Immunity against dsDNA viruses requires the DNA, but not the RNA cleavage activity of the Cas10-Csm complex. (A) Sequence of the gp43 gene of the φNM1γ6 staphylococcal dsDNA phage (22,390-22,449 bp) targeted by both type III-A (right-most box) and type II-A (left-most box) CRISPR-Cas systems. (B) Staphylococci harboring different CRISPR-Cas systems targeting the gp43 gene as shown in panel A were grown in liquid media and infected with φNM1γ6 phage (at 0 hours). Optical density was measured for the following 10 hours to monitor cell survival due to CRISPR immunity against the phage.

Figure 22:
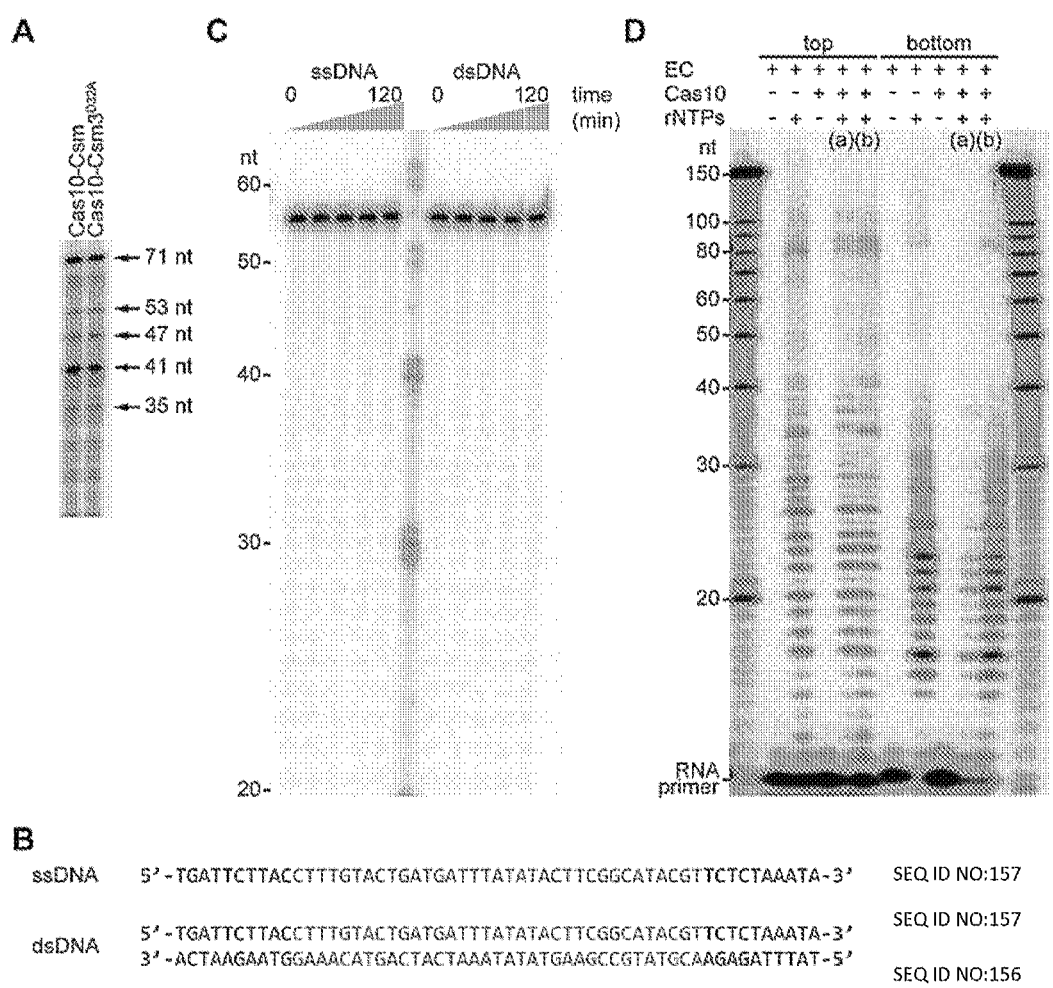

FIG. 22. (A) Analysis of crRNAs associated with the wild-type and csm3$^{D32A}$ Cas10-Csm complex. RNA was extracted from purified complexes, radiolabeled, separated by denaturing PAGE and visualized by gel autoradiography. (B) ssDNA and dsDNA substrates used in to determine the cleavage properties of the Cas10-Csm complex in the absence of transcription. (C) Radiolabeled substrates shown in panel B were incubated with the Cas10-Csm complex in the absence of transcription for 0, 10, 30, 60 and 120 minutes. (D) Transcription of the substrate shown in FIG. 15D followed as the extension of a radiolabeled RNA primer. Transcription is shown for both the assay of top (FIG. 15E) and bottom (FIG. 15F) strand cleavage. Lanes (a) and (b) differ in the order of addition of the Cas10-Csm complex with respect to the initiation of transcription. In lane (a) the Cas10-Csm complex was added to the elongation complex and incubated for 10 minutes prior to the initiation of transcription by the addition of rNTPs. In lane (b) the Cas10-Csm complex was added 10 minutes after transcription initiation by the addition of rNTPs to the elongation complex.

Figure 23:
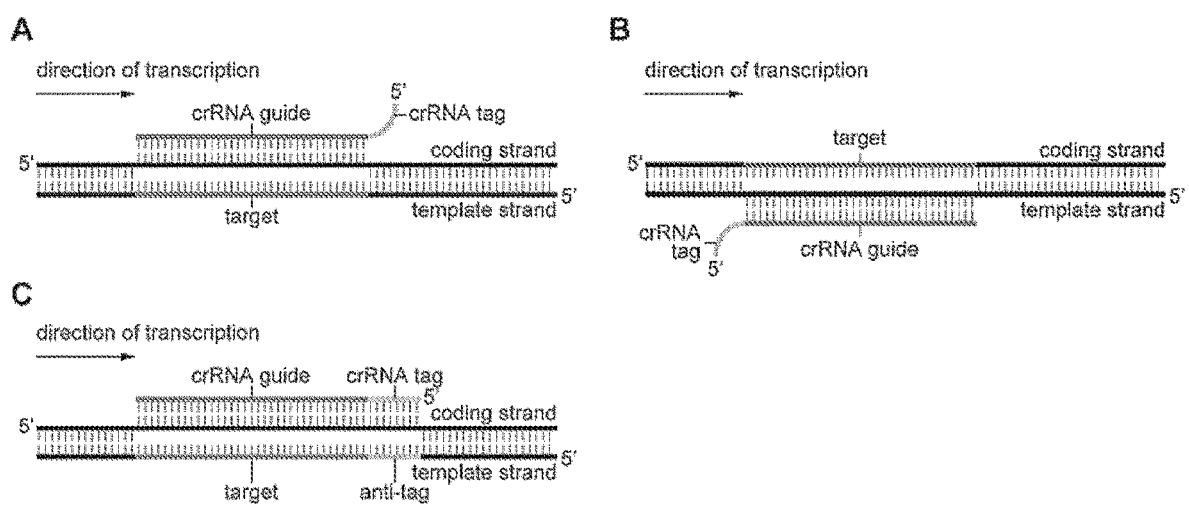

FIG. 23. (A) Target:crRNA configuration that licenses CRISPR-Cas immunity. crRNAs annealing to the coding strand of a transcribed region of the phage can provide robust immunity. The most abundant crRNA produced by the S. epidermidis type III-A CRISPR-Cas system in staphylococci contains 35 nt of spacer sequence, which acts as the guide for the Cas10-Csm complex (shown in lighter shading with base pairing between the crRNA guide sequence and coding strand, and lighter shading for the target sequence) on the template strand). At the 5' end of the guide sequence there are 8 nt of repeat sequence known as the crRNA tag (light green). (B) A crRNA guide complementary to the template strand of a transcribed phage does not support immunity. (C) The presence of an anti-tag sequence (complementary to the crRNA tag sequence) immediately upstream of the target prevents effective immunity, even if the crRNA guide anneals to the coding strand of a transcribed viral region.

FIG. 24. (A) Mapping of the RNA cleavage products shown in FIG. 17C. The Cas10-Csm cleavage products (black arrowheads) were compared to those of the RNases A (5' of adenine and uridine residues, light arrowheads) and T1 (5' of guanosine residues, dark arrowheads). (B) Analysis of the cleavage sites detected in panel A in relation with the ssRNA substrate sequence. (C) Sequence of a ssRNA substrate with a scrambled, non-specific sequence. (D) Cleavage of the radiolabeled substrate shown in panel C by the Cas10-Csm complex; incubation times: 0, 5, 10, 20, 30, 60, 120, 180 and 240 minutes. The sequence of the non-specific ssRNA target in FIG. 24(c) is SEQ ID NO:179.

DETAILED DESCRIPTION OF THE DISCLOSURE

The present disclosure provides in various aspects novel compositions and methods for using and adapting type III-A CRISPR-Cas systems to exploit a newly discovered transcription-dependent DNA targeting mechanism that these systems employ. Thus, the present disclosure relates generally to a fundamental feature of immune systems, namely the ability to distinguish pathogenic from self and commensal elements, and to attack the former but tolerate the latter[1]. In this regard, prokaryotic CRISPR-Cas immune systems defend against phage infection using Cas nucleases and small RNA guides that specify one or more target sites for cleavage of the viral genome[2,3]. In the present disclosure, we use temperate phages and engineered derivatives thereof to demonstrate a novel mechanism by which type III CRISPR-Cas systems function, and extend this discovery to provide new compositions and methods that incorporate this mechanism. The phage related examples are used to illustrate the generally applicability of this approach for transcription dependent CRISPR targeting in any cell, but is not meant to be limited in any way for use with temperate phages only.

Unless defined otherwise herein, all technical and scientific terms used herein have the same meaning as commonly understood by one of ordinary skill in the art to which this disclosure pertains.

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

In general, the instant disclosure includes compositions and methods that facilitate site-directed modification of a target DNA sequence, with the proviso that the modification is only made when and if the target DNA sequence is transcribed. In particular, this disclosure uses temperate phages and engineered derivatives thereof to demonstrate site specific and transcription-dependent CRISPR/Cas10 mediated endonuclease activity. Isolated and/or purified enzymes and methods of using them for site-directed modification of a DNA target sequence are also provided. It will be recognized that modification of the target DNA sequence comprises cleavage of a DNA strand, wherein "cleavage" means breaking a phosphodiester bond. In embodiments, only the non-template strand is cleaved. The non-template strand is the strand that is complementary to the template DNA strand that is transcribed by the RNA polymerase. Thus, in embodiments, the non-template strand comprises a polynucleotide sequence that is identical to the transcribed RNA sequence, with the exception of the substitution of U for T in the transcribed RNA.

With respect to temperate phages, as is known in the art, they are viruses of bacteria that can integrate into the bacterial chromosome, and can carry genes that provide a fitness advantage to the lysogenic host. However, CRISPR-Cas targeting that relies strictly on DNA sequence recognition provides indiscriminate immunity to both lytic and lysogenic infection by temperate phages—compromising the genetic stability of these potentially beneficial elements altogether. In this disclosure we demonstrate that a representative CRISPR-Cas Type III-A system can prevent lytic infection but tolerate lysogenization by temperate phages, and for the first time show that such conditional tolerance is achieved through CRISPR-Cas mediated transcription-dependent DNA targeting. This strategy ensures that targeting resumes upon induction of the prophage lytic cycle. Our results provide evidence for the functional divergence of CRISPR-Cas systems and the importance of targeting mechanism diversity and extend the concept of 'tolerance to non-self' to the prokaryotic branch of adaptive immunity. Further, they provide the basis for a new class of compositions and methods that are suitable for use in a wide variety of practical applications as described further herein.

Further, the present disclosure provides in various embodiments in vivo and in vitro demonstration using the type III-A CRISPR-Cas system of S. epidermidis to show dual crRNA-guided cleavage of the target DNA and its transcripts. In particular, we show that purified Cas10-Csm complexes cleave double-stranded DNA targets. Without intending to be constrained by any particular theory, it is considered that this reaction requires transcription across the target and it is inhibited by the presence of homology between the crRNA tag and the 5' target flanking sequence. The same complex is also capable of crRNA-guided RNA cleavage in vitro, and this reaction is not prevented by crRNA tag homology. In vivo, type III-A targeting of a plasmid shows degradation of the DNA upon induction of transcription across the target, as well as a precise cut of the target transcript. We also show that DNA and RNA targeting are independent events. Whereas DNA targeting requires an intact Cas10 palm polymerase domain, RNA targeting requires a nucleolytic active site in Csm3, both in vitro and in vivo. Mutations that affect DNA cleavage do not affect RNA cleavage and vice versa. Moreover, in vivo experiments described herein show that DNA, but not RNA, cleavage is required for immunity against plasmids and DNA viruses. These results consolidate distinct mechanistic observations of type III-A targeting into a single model and reveal a highly elaborated targeting strategy distinct from the type I and type II CRISPR-Cas systems.

In general, the present disclosure involves providing and using modified type III CRISPR-Cas systems and/or purified or isolated proteins, and endogenous or engineered targets for transcription-restricted targeting of DNA sequences. As such the disclosure includes compositions and methods for recombinant expression of the cas10 gene, cas10 being a hallmark of type III CRISPR systems. In addition to a cas10 gene, the disclosure includes use of one or more polynucleotides which encode, in addition to cas10, cas6 and a Csm protein selected from the group consisting of Csm2, Csm3, Csm4, Csm5 and Csm6, and combinations thereof. In embodiments, the disclosure includes one or more recombinant polynucleotides that encode each of cas10, cas6, Csm2, Csm3, Csm4, Csm5 and Csm6. In embodiments, only two, three, or four Csm proteins are encoded by the expression vector.

It is expected that the cas and csm gene sequences can be any naturally occurring sequences, or the sequences can be modified. In embodiments, one or more of the cas and csm sequences are encoded by the *S. epidermidis* genome. GenBank accession no. NC_002976.3 can be used to access *S. epidermidis* genome nucleotide sequences and the protein sequences encoded by it. Likewise, the amino acid sequences of the individual cas and csm genes and the polypeptides they encode are known in the art and are available under the following GenBank accession numbers: Cas10: AAW53330.1 (SERP2461); Csm2: AAW53329.1 (SERP2460); Csm3: AAW53328.1 (SERP2459); Csm4: AAW53327.1 (SERP2458); Csm5: AAW53326.1 (SERP2457); Csm6: AAW53325.1 (SERP2456); Cas6: AAW53324.1 (SERP2455). The parenthetical references designate locus tags for the corresponding nucleotide sequences in the aforementioned *S. epidermidis* genome. The sequences listed with each GenBank accession number described in this disclosure are incorporated herein by reference as those sequences existed in GenBank on the filing date of this application or patent. For every amino acid sequence described herein the disclosure includes each and every nucleotide sequence encoding it. In embodiments, the cas and csm genes and polypeptides encoded by them as used in this disclosure have between 80%-99% identity to the *S. epidermidis* sequences referenced herein. However, it is expected that cas and csm genes of other types of bacteria can also be used. In non-limiting embodiments, the disclosure includes the cas and csm nucleotide and protein sequences from other *staphylococcus* and *streptococcus* species and archaeal species, such as *Sulfolobus solfataricus, Methanopyrus kandleri* and *Thermus thermophilus* harboring type III CRISPR-Cas systems, as well as cas and csm genes and polypeptides encoded by other prokaryotes that have between 80%-99% identity to such non-*S. epidermidis* types of bacteria.

Representative Cas and Csm sequences include:

```
Cas10 (the italicized and bold DD couplet is
changed to AA in the cas10^palm mutant described
herein)
                                        (SEQ ID NO: 2)
MNKKNILMYGSLLHDIGKIIYRSGDHTFSRGTHSKLGHQFLSQFSEFKDN

EVLDNVAYHHYKELAKANLDNDNTAYITYIADNIASGIDRRDIIEEGDEE

YEKQLFNFDKYTPLYSVFNIVNSEKLKQTNGKFKFSNESNIEYPKTENIQ

YSSGNYTTLMKDMSHDLEHKLSIKEGTFPSLLQWTESLWQYVPSSTNKNQ

LIDISLYDHSRITCAIASCIFDYLNENNIHNYKDELFSKYENTKSFYQKE

AFLLLSMDMSGIQDFIYNISGSKALKSLRSRSFYLELMLEVIVDQLLERL

ELARANLLYTGGGHAYLLVSNTDKVKKKITQFNNELKKWFMSEFTTDLSL

SMAFEKCSGDDLMNTSGNYRTIWRNVSSKLSDIKAHKYSAEDILKLNHFH

SYGDRECKECLRSDIDINDDGLCSICEGIINISNDLRDKSFFVLSETGKL

KMPFNKFISVIDYEEAEMLVQNNNQVRIYSKNKPYIGIGISTNLWMCDYD

YASQNQDMREKGIGSYVDREEGVKRLGVVRADIDNLGATFISGIPEKYNS

ISRTATLSRQLSLFFKYELNHLLENYQITAIYSGGDDLFLIGAWDDIIEA

SIYINDKFKEFTLDKLTLSAGVGMFSGKYPVSKMAFETGRLEEAAKTGEK

NQISLWLQEKVYNWDEFKKNILEEKLLVLQQGFSQTDEHGKAFIYKMLAL

LRNNEAINIARLAYLLARSKMNEDFTSKIFNWAQNDKDKNQLITALEYYI

YQIREAD

Csm2
                                        (SEQ ID NO: 3)
MILAKTKSGKTIDLTFAHEVVKSNVKNVKDRKGKEKQVLFNGLTTSKLRN

LMEQVNRLYTIAFNSNEDQLNEEFIDELEYLKIKFYYEAGREKSVDEFLK

KTLMFPIIDRVIKKESKKFFLDYCKYFEALVAYAKYYQKED

Csm3
                                        (SEQ ID NO: 4)
MYSKIKISGTIEVVTGLHIGGGGESSMIGAIDSPVVRDLQTKLPIIPGSS

IKGKMRNLLAKHFGLKMKQESHNQDDERVLRLFGSSEKGNIQRARLQISD

AFFSEKTKEHFAQNDIAYTETKFENTINRLTAVANPRQIERVTRGSEFDF

VFIYNVDEESQVEDDFENIEKAIHLLENDYLGGGGTRGNGRIQFKDTNIE

TVVGEYDSTNLKIK

Csm4
                                        (SEQ ID NO: 5)
MTLATKVFKLSFKTPVHFGKKRLSDGEMTITADTLFSALFIETLQLGKDT

DWLLNDLIISDTFPYENELYYLPKPLIKIDSKEEDNHKAFKKLKYVPVHH

YNQYLNGELSAEDATDLNDIFNIGYFSLQTKVSLIAQETDSSADSEPYSV

GTFTFEPEAGLYFIAKGSEETLDHLNNIMTALQYSGLGGKRNAGYGQFEY
```

-continued

EIINNQQLSKLLNQNGKHSILLSTAMAKKEEIESALKEARYILTKRSGFV

QSTNYSEMLVKKSDFYSFSSGSVFKNIFNGDIFNVGHNGKHPVYRYAKPL

WLEV

Csm5
(SEQ ID NO: 6)
MTIKNYEVVIKTLGPIHIGSGQVMKKQDYIYDFYNSKVYMINGNKLVKFL

KRKNLLYTYQNFLRYPPKNPRENGLKDYLDAQNVKQSEWEAFVSYSEKVN

QGKKYGNTRPKPLNDLHLMVRDGQNKVYLPGSSIKGAIKTTLVSKYNNEK

NKDIYSKIKVSDSKPIDESNLAIYQKIDINKSEKSMPLYRECIDVNTEIK

FKLTIEDEIYSINEIEQSIQDFYKNYYDKWLVGFKETKGGRRFALEGGIP

DVLNQNILFLGAGTGFVSKTTHYQLKNRKQAKQDSFEILTKKFRGTYGKM

KEIPSNVPVALKGTTNQSRHTSYQQGMCKVSFQELNNEVL

Csm6
(SEQ ID NO: 7)
MKILFSPIGNSDPWRNDRDGAMLHIVRHYNLDKVVLYFTRTIWEGNENRK

GHKIYEWEKIIQTVSPNTEVEIIIENVDNAQDYDVFKEKFHKYLKIIEDS

YEDCEIILNVTSGTPQMESTLCLEYIVYPENKKCVQVSTPTKDSNAGIEY

SNPKDKVEEFEIVNEVEKKSEKRCKEINILSFREAMIRSQILGLIDNYDY

EGALNLVSNQKSFRNGKLLRKKLLSLTKQIKTHEVFPEINEKYRDDALKK

SLFHYLLLNMRYNRLDVAETLIRVKSIAEFILKTYIEIHWPTLIIEKDGK

PYLNDEDNLSFVYKYNLLLEKRKQNFDVSRILGLPAFIDILTILEPNSQL

LKEVNAVNDINGLRNSIAHNLDTLNLDKNKNYKKIMLSVEAIKNMLHISF

PEIEEEDYNYFEEKNKEFKELL

Cas6
(SEQ ID NO: 8)
MINKITVELDLPESIRFQYLGSVLHGVLMDYLSDDIADQLHHEFAYSPLK

QRIYHKNKKIIWEIVCMSDNLFKEVVKLFSSKNSLLLKYYQTNIDIQSFQ

IEKINVQNMMNQLLQVEDLSRYVRLNIQTPMSFKYQNSYMIFPDVKRFFR

SIMIQFDAFFEEYRMYDKETLNFLEKNVNIVDYKLKSTRFNLEKVKIPSF

TGEIVFKIKGPLPFLQLTHFLLKFGEFSGSGIKTSLGMGKYSII

In addition to these Cas and Csm coding regions, the disclosure includes at least one polynucleotide sequence that encodes a CRISPR RNA (crRNA) targeted to a DNA sequence that is operatively linked to a promoter. A "promoter" is a DNA sequence at which initiation and in certain instances the rate of transcription is controlled. A promoter can comprises genetic elements at which an RNA polymerase and regulatory proteins, such transcription factors, can bind with specificity. Many promoters that are pertinent to the instant disclosure are well known in the art, and can include any eukaryotic, prokaryotic, viral and bacteriophage promoters. The phrase "operatively linked" means that the promoter is in a correct functional location and/or orientation in relation to a nucleic acid sequence to control transcriptional initiation and/or expression of RNA from that sequence. The promoters which drive expression of coding regions that are targeted by the CRISPR systems described herein can be constitutively active promoters, inducible promoters, cell-specific or tissue-specific promoters, and/or promoters that are responsive to any other conditional stimuli, including but not limited to temperature, nutrients, antibiotics, oxygen concentration, cell cycle phases, quorum sensing, chemokines, cytokines, growth factors, or any other stimulus or compound that can drive gene expression from the particular promoter in question. In embodiments, the promoter is a prokaryotic promoter. In embodiments, the promoter is an RNA-polymerase II eukaryotic promoter.

Figure 1:
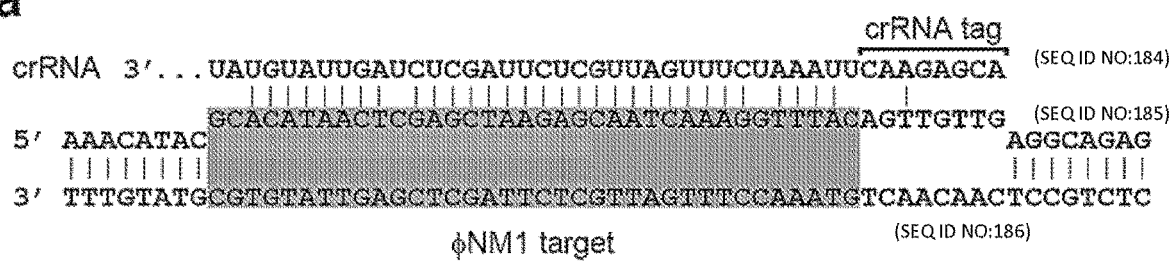
FIG. 1. Type III-A CRISPR immunity can block lytic infection but tolerate lysogenization. a, Base pairing interaction between crRNA 32T and its target in the ΦNM1 genome (highlighted in gray). The crRNA tag is a sequence transcribed from the CRISPR repeat that needs to be unpaired with the flanking region of the target to license immunity. The target gene is transcribed from left to right. crRNA is SEQ ID NO: 184 including tag. Top strand sequence is SEQ ID NO: 185 including offset 3' sequence. Bottom strand is SEQ ID NO:186. b, CRISPR immunity against ΦNM1 infection provided by spacers 32T and 32T* (similar to 32T but without mismatches), measured as a decrease in the number of plaque forming units (pfu) with respect to the non-targeting control pGG3 (C). c, Lysogenization with ΦNM1-Erm^R in the presence of spacers 32T and 32T* or the pGG3 control (C), measured as the number of chloramphenicol- and erythromycin-resistant colony forming units (cfu) per ml obtained after infection. Control cells lysogenized with ΦNM1 (C') lack the ermC insertion and do not yield erythromycin-resistant cfu. Error bars: mean±s.d.
Figure 1:
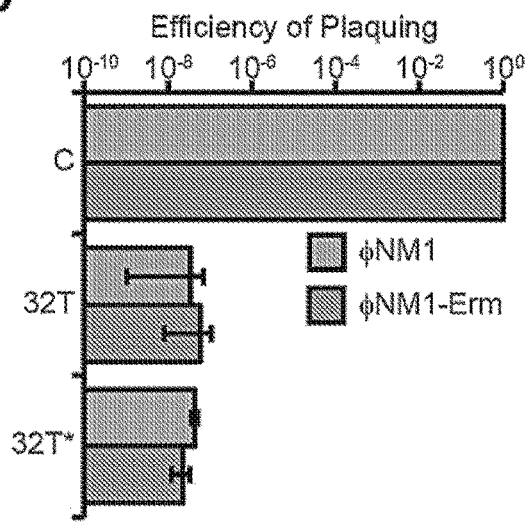
Figure 1:
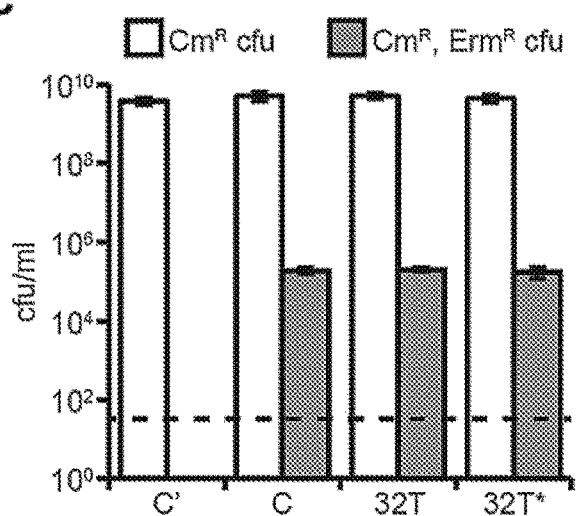

The type, sequence, and length of the RNA that is transcribed from the promoter can vary, and in embodiments the method is ambivalent to whether or not the RNA contains a protein coding sequence. In embodiments, the RNA is an unspliced RNA. In embodiments, the RNA is any RNA that has potential for post-transcriptional modifications, including but not limited to splicing and RNA editing. In an embodiment, the RNA is an mRNA. With respect to crRNA, as will be recognized by those skilled in the art, the structure of a naturally occurring CRISPR locus includes a number of short repeating sequences generally referred to as "repeats." The repeats occur in clusters and up to 249 repeats have been identified in a single CRISPR locus and are usually regularly spaced by unique intervening sequences referred to as "spacers." Typically, CRISPR repeats vary from about 24 to 47 bp in length and are partially palindromic. The repeats are generally arranged in clusters (up to about 20 or more per genome) of repeated units. The spacers are located between two repeats and typically each spacer has a unique sequence of about 20-72 bp in length. As it occurs naturally, during the crRNA biogenesis phase, repeat/spacer arrays are transcribed as a long precursor that is cleaved within repeat sequences and processed into smaller crRNAs by Cas endoribonucleases. crRNAs retain spacer sequences that specify the targets of CRISPR interference. In the targeting phase crRNAs are used as complementary guide in Cas/crRNA ribonucleoprotein complexes that cleave the nucleic acids of mobile genetic elements carrying a cognate sequence, known as the protospacer, also referred to herein and as noted above as a "spacer." The "crRNA tag" as the term is used herein comprises 8 nucleotides of repeat-derived sequence at the 5' end of the crRNA. A representative diagram of this is presented in FIG. 1A. When the spacer-derived sequence of the crRNA anneals to its DNA target (the spacer), the crRNA tag is located adjacent to the spacer, as depicted in FIG. 1A. As described herein, in type III CRISPR systems, targeting is prevented by excessive base pairing between the repeat-derived crRNA tag and its corresponding DNA sequence. Thus, in order for targeting to occur, the crRNA tag comprises sufficient mismatching between it and the corresponding DNA sequence adjacent to the spacer, again as outlined in FIG. 1a. In embodiments, the crRNA comprises 8 mismatches, i.e., no crRNA tag bases are complementary to the non-template sequence adjacent to the spacer. In embodiments the crRNA tag comprises 7, 6, 5, 4, 3, 2, or 1 mismatches relative to the non-template sequence adjacent to the spacer. FIG. 1a provides a non-limiting example wherein the crRNA tag comprises 7 mismatches relative to the 8 bases immediately 5' to the shaded spacer sequence that present in the non-template strand.

In an embodiment, a representative naturally occurring type III-A CRISPR locus comprises the following sequence, which contains 4 repeats (underlined) and 3 spacers (bold, italicized). Non-emphasized upstream sequences include a putative promoter:

(SEQ ID NO: 9)
```
CGAAATATAAAAAGAAATGAAAGGTTAAATTAATATTAATTTTATTAAATGAATAGGCTAAA

CCATCTTAAATGTAGTATACTATTAATATAAATGTAATTATTATAAAATTTGTCAAAAAAG

TGACATATCATATAATCTTGTACTAGTGATTGTCATATTTTTTGACAGCAAAAATGATGCTT

GAAATATAGTTGTGATGGCATTTGTTAAAGTATCGGATCGATACCCACCCCGAAGAAAAGGG

GACGAGAACACGTATGCCGAAGTATATAAATCATCAGTACAAAGGATCGATACCCACCCCGA

AGAAAAGGGGACGAGAACTAGTAATAATTGTCATTTGCATACGTTACATCGATGATCGATAC

CCACCCCGAAGAAAAGGGGACGAGAACTAGTACGGTCGTGAACATTTTTTCTTGATTCTCTG

ATCGATAGCCACCCCGAAGAAAAGGGGGCAGAGTG
```

In general, the present disclosure is pertinent to spacer sequences that are subject to cleavage by any Type III-A CRISPR system, provided that the spacer sequences are transcribed as a contingency to such cleavage. In embodiments, a crRNA comprises a segment that is the same as or complementary to a DNA target sequence (a spacer) in the targeted cell that is operatively linked to a promoter. The "top" or "bottom" strands of a DNA duplex can comprise the target spacer sequence. In general a mature crRNA, meaning a crRNA that is complexed with a Cas during cleavage of a DNA target sequence, will comprise or consist of from 31 or more nucleotides. In embodiments, a crRNA has at its 5' terminus an 8 nt sequence derived from an upstream repeat sequence, followed by a variable length of nucleotides derived from the spacer, and in some cases additional nucleotides derived from downstream sequences. Thus, in embodiments, a crRNA that is used in the present disclosure will comprise at least 31 nucleotides, with a minimum of 23 nucleotides derived from the spacer sequence. In embodiments, the longer mature crRNA species, e.g., a species with nucleotides derived from the downstream repeat or beyond, is referred to as an intermediate species so that it is distinguished from mature crRNAs which do not necessarily include nucleotides from sequences beyond the spacer. Thus, in embodiments the present disclosure involves pre-crRNA, intermediate crRNA and mature crRNA. In specific and non-limiting embodiments, the crRNA comprises or consists of a segment that targets any one of the genes and/or spacers that are described herein. It will be recognized that where T is presented in the sequences it will be replaced by U in the crRNA. The crRNA can therefore comprise a segment that itself comprises or consists of a sequence that is identical to the any of the sequences presented herein, wherein each T is replace by U, or the crRNA can comprise a segment that itself comprises or consists of a sequence that is the RNA complement of any of the sequences presented herein. DNA sequences encoding all of the sequences presented herein are also included with the scope of this disclosure. The disclosure also comprises mismatches between the crRNA and the spacer sequence. In this regard, it is known in the art that type III CRISPR systems can generally recognize their target despite a few mismatches within the target sequence. While FIG. 1a provides a non-limiting example of 5 mismatches between the crRNA and the non-template strand of the shaded spacer sequence, it is known in the art that more mismatches between the crRNA and spacer sequence can be tolerated and still facilitate cleavage of the target. For example, as many as 15 mismatches between the crRNA and spacer have been reported (see, for example, Manica, A. et al. Unexpectedly broad target recognition of the CRISPR-mediated virus defence system in the archaeon Sulfolobus solfataricus. Nucleic Acids Res. 41, 10509-10517 (2013)). Thus, the present disclosure includes mismatches between the crRNA and the spacer, including 1, 2, 3, 4, 5, 6, 7, 8, 9, 10, 11, 12, 13, 14, and 15 mismatches, and all ranges between 1 and 15 mismatches, including from 1-15 mismatches. More mismatches can also be tolerated so long as there is adequate complementarity between the crRNA and the spacer so that specific transcription-dependent cleavage of the target DNA is facilitated.

It will be apparent from the foregoing that, in one aspect, the present disclosure includes one or more recombinant polynucleotides comprising a CRISPR system, wherein the CRISPR system comprises nucleotide sequences encoding: i) at least one crRNA targeted to a DNA sequence that is operatively linked to a promoter in a cell; and ii) a Cas10 enzyme, a Cas6 protein, and a Csm protein selected from the group consisting of a Csm2 protein, a Csm3 protein, a Csm4 protein, a Csm5 protein and a Csm6 protein, and combinations thereof. In embodiments, a single polynucleotides encodes the crRNA, the Cas10 enzyme, the Cas6, and the Csm proteins. In embodiments, the polynucleotide is provided in an expression vector. Any suitable expression vector can be used. In embodiments, the expression vector is a plasmid, or is a modified viral vector. In an embodiment, the expression vector is a phagemid. In embodiments, the phagemid is provided as a component of a bacteriophage.

In embodiments, the polynucleotide encoding the CRISPR system is transiently present in a cell. In embodiments, the polynucleotide encoding the CRISPR system is stably present in the cell, and may be integrated into a chromosome. In embodiments, the expression vector is maintained in the cell using a selectable marker which is also encoded by the expression vector, such as an antibiotic resistance gene, or a gene that subjects the cell(s) comprising the vector to a nutritional selection. In embodiments, the expression vector is a yeast artificial chromosome (YAC) or a bacterial artificial chromosome (BAC). Expression vectors can be introduced into cells using any suitable technique and delivery system, many of which are known in the art and include but are not limited to electroporation, lipid-based transfection systems, standard plasmid transformation approaches, such as by using competent cells, phage or viral transduction, micro-injection, including direct injection of a CRISPR vector or CRISPR RNA itself. In embodiments, the cas and csm proteins can be directly injected into a cell configured to express a suitable crRNA.

In embodiments, the crRNA coding region itself can be operatively linked to an inducible promoter on the expression vector, or to a promoter on the expression vector that is sensitive to another stimulus. In embodiments, the promoter that drives transcription of the crRNA can be the same promoter that drives expression of the DNA encoding the spacer. In such a configuration, the crRNA should only be expressed when RNA encoded by the target DNA is also expressed.

In another aspect, methods of using the compositions of this disclosure are provided. In various embodiments, the disclosure includes methods for modification of a DNA sequence in a cell comprising introducing into the cell a recombinant vector comprising a CRISPR system as described above, wherein the Cas10 modifies the DNA sequence only during transcription of the DNA sequence, wherein the DNA sequence comprises a CRISPR target sequence, i.e., a spacer, and wherein the crRNA comprises a sequence targeted to the spacer. In certain embodiments, the modification of the DNA is conditional in that transcription of the DNA from the promoter is not constitutive transcription. In embodiments, the transcription of the targeted DNA is driven by an inducible promoter, or a promoter that is activated by another stimulus. In an embodiment, the method comprises inducing transcription from an inducible promoter to facilitate modification of the transcribed DNA by the CRISPR system. In embodiments, transcription of DNA comprising a CRISPR target sequence (i.e., a spacer) occurs, the transcribed DNA is modified by the CRISPR system, and the modification of the DNA sequence confers a change in phenotype of the cell, or change in expression of a detectable or selectable marker. In embodiments, cells which exhibit a change in phenotype, or which exhibit a change in expression of detectable or selectable marker subsequent to transcription of a DNA sequence that comprises a spacer are identified, and the transcribed DNA sequence is determined. In one embodiment, the detectable marker produces a visually detectable signal, such as a florescent signal, or a colorimetric signal. In embodiments, the CRISPR system is configured to distinguish transcription of a gene that encodes a protein of interest fused to a detectable marker. For example, in an illustrative and non-limiting embodiment, a gene encoding a protein of interest is modified such that it is encoded in-frame with green fluorescent protein (GFP). When the sequence is transcribed it is targeted by a CRISPR system and as a consequence the cell ceases production of GFP and can accordingly be identified and/or separated from cells that continue to express GFP. Such an approach could be used, for example, to investigate a stimulus or other factor that caused the distinction between the GFP(+) and GFP(−) cells.

In embodiments, the DNA sequence that is transcribed and modified by operation of the CRISPR system is present in a chromosome. In embodiments, the DNA sequence that is transcribed and modified by operation of the CRISPR system is on an extrachromosomal element, such as a plasmid. In embodiments, the plasmid does not comprise a temperature sensitive (Ts) origin of replication, or a Ts promoter. In embodiments, modification of the DNA sequence that is, for example, on a plasmid, comprises cleavage of the plasmid such that it is linearized and/or enzymatically degraded, or its nucleotide sequence is altered due to cleavage and enzymatic repair.

In one aspect of the disclosure, an engineered CRISPR vector is introduced into a plurality of cells, such as a population of bacteria, wherein the crRNA encoded by the vector is targeted to a spacer that is known or suspected to be present in at least some of the bacteria, such as in the bacterial chromosome, or is present in a prophage, a pathogenicity island, and/or a plasmid. For eukaryotic cells, the crRNA could be targeted to a transposon, an integrated virus, a virus that replicates with a DNA intermediate, or any virus that is encoded by a DNA polynucleotide at least once during its replication cycle. Thus, the CRISPR system facilitates cleavage of the DNA comprising the spacer only when transcription of the DNA comprising the spacer is initiated in at least some of the bacteria. In this manner, the disclosure includes the selective and conditional elimination or editing of DNA elements from a population of cells. In one embodiment, this aspect of the disclosure comprises the controlled removal of naturally occurring or engineered plasmids. In one embodiment, the CRISPR-system facilitated targeting of the DNA is lethal to the cell. In an embodiment, the disclosure accordingly provides for development of suicide-inducible bacterial strains.

In another aspect the disclosure includes use of the compositions in methods for detection/surveillance of transcriptional activity in vivo. For example, in embodiments, an engineered CRISPR system is introduced into a population of cells which are then analyzed, such as by flow cytometry, or optical density, or any other suitable approach, to determine whether or not transcription of a gene to which the crRNA is targeted occurred. In embodiments, transcription of genes that are essential for survival or for exhibiting a particular phenotype is detected due to CRISPR-facilitated editing of such genes, thereby resulting in cell death or a change in phenotype. By comparison to a suitable control (i.e., a cell in which there is no transcription and thus no editing of the gene in question), the genes that were transcribed and edited can be identified by sequencing the genes containing the spacer.

In another aspect, a plurality of distinct CRISPR systems as described herein, wherein members of the plurality are differentiated from one another by the crRNAs they encode, can be introduced into a plurality of cell samples which can be analyzed for a change in phenotype, detectable marker, selection, or for lethality, or any other trait that is correlated with transcription of a DNA segment that contains a spacer. In embodiments this approach can be adapted for high throughput screening. For example, a plurality of eukaryotic cells is divided into separate samples, such as into separate reaction chambers. A distinct CRISPR system is introduced into each of the samples wherein each system has a distinct crRNA, a period of time is allowed to pass, and the samples are analyzed for a change in phenotype, or for lethality, or for any other detectable trait. In an illustrative and non-limiting embodiment, one or more of the samples develop an immortalized phenotype. Thus, by comparison of the spacer in the crRNA to the cognate target in the immortalized cell samples, an edited DNA sequence that was (pre-editing) responsible for maintaining a non-immortalized phenotype is identified. It is plausible that this approach could be used to identify proto-oncogenes, tumor repressors and the like. Similar approaches could be used for investigating any other trait that is correlated with transcription of DNA that comprises a spacer, and can be used in any cell type. For example, the approach can be adapted to determine editing-based transition of samples of a bacterial strain from a pathogenic to non-pathogenic phenotype, which could be used to identify a plasmid that confers pathogenicity. Such a CRISPR system could then be used to maintain the non-pathogenic status of a population of bacteria by editing and concomitant removal of the plasmid that confers the pathogenicity whenever such a plasmid is subsequently acquired and the spacer is transcribed.

In another aspect, the disclosure comprises conditional counter-selection for the editing of prokaryotic genomes. In this manner, and as described above, the disclosure includes the selective and conditional elimination or editing of DNA elements from a population of cells.

In embodiments, one or more polynucleotides encoding a CRISPR system of this disclosure are introduced into any of a variety of cell types, including but not limited to prokaryotic and eukaryotic cells. In embodiments, the cells are modified ex vivo using a CRISPR system of this disclosure and introduced into an organism, or an ex vivo organ or tissue. In embodiments, the cells are in vitro. In embodiments, the cells are present in a multicellular organism. In embodiments, the cells that are modified using a CRISPR system of this disclosure comprise totipotent, pluripotent, or multipotent stem cells. In embodiments, the cells are hematopoietic stem cells, or are progenitor cells of any other lineage. In embodiments, the cells are embryonic stem cells (ES cells), or adult stem cells, such as tissue-specific stem cells, or epidermal stem cells or epithelial stem cells. In embodiments, the cells are immune cells, including but not necessarily limited to T Cells, B cells, antigen presenting cells, such as dendritic cells, or other cells of the adaptive or passive immune system. In embodiments, the cells are cancer cells, including but not limited to blood cancers, and solid tumor cells, and metastatic cells. In embodiments, the cells are mammalian cells. In embodiments, the cells are human cells, or are non-human mammalian cells. The disclosure includes cells that comprise the CRISPR system and are modified, and the progeny of such cells, whether or not the progeny comprise the CRISPR system, such as cells that are propagated in culture, and/or are stored, such as in a cooled or frozen environment with one or more cryoprotective agents, such as glycerol.

In embodiments, the disclosure comprises introducing into a test plurality of cells a CRISPR system of this disclosure, allowing CRISPR-mediated cleavage of a target DNA in the test plurality of cells, and comparing one or more changes in the plurality of test cells to a suitable reference, such as a control plurality of cells into which the CRISPR system has not been introduced, and/or cells of a known phenotype or other characteristic, or any other suitable reference. By comparing one or more changes in the modified cells to the reference, the location and/or identify of transcription units that are correlated with the changes in the modified cells can be identified.

In certain aspects of this disclosure, a composition of the invention is administered to an individual for a prophylactic or therapeutic purpose, and thus can be provided as a pharmaceutical preparation by mixing a polynucleotide described herein with a pharmaceutically acceptable carrier. The term "pharmaceutically acceptable carrier" refers to a substantially non-toxic carrier for administration of pharmaceuticals in which the composition will remain stable and bioavailable. Details of suitable pharmaceutically acceptable carriers and formulations can be found in Remington's Pharmaceutical Sciences (19th ed., 1995), which is incorporated herein by reference. The pharmaceutical composition can further comprise an additional active ingredient(s), such as an antibiotic.

Examples of prophylactic or therapeutic purpose purposes include but are not necessarily limited to inhibiting the growth of, reducing the amount of and/or killing undesirable and/or pathogenic microorganisms, or to reduce the pathogenicity and/or antibiotic resistance of such microorganisms. For administering to a subject in need thereof, the pharmaceutical composition may be administered using any suitable route and type of formulation, and the dosing of the formulation can be determined by those skilled in the art given the benefit of the present disclosure. In an embodiment, the compositions and methods of the invention relate to reducing pathogenic bacteria. In embodiments, the compositions and methods are adapted for veterinary purposes.

In another approach, the compositions and methods of this disclosure are adapted for use in eliminating pathogenic bacteria from a non-living surface, such as a the surface of a device, or the surface of an area used for any procedure wherein the reduction of pathogenic bacteria is important, including but not necessarily limited to surfaces used for food preparation or medical purposes. In an embodiment, the present disclosure includes kit comprising at least one sealed container. The sealed container comprises a recombinant expression vector encoding a CRISPR system as described herein. In an embodiment, an article of manufacture comprising at least one container as described for the kit, and packaging material is provided. The packaging comprises printed material providing an indication that it contains a vector encoding a CRISPR system as described herein, and its use as a transcription-dependent gene editing agent.

The following Example is presented to illustrate the present disclosure. It is not intended to be limiting in any manner. In some aspects, the Example includes routine techniques and methods used in the field of genetic engineering and molecular biology that are not otherwise described. The following resources include descriptions of general methodology useful in accordance with the invention: Sambrook et al., Molecular Cloning: A Laboratory Manual (4th Ed., 2012); Kreigler, Gene Transfer and Expression: A Laboratory Manual (1993) and Ausubel et al., Eds. Current Protocols in Molecular Biology (1995). These general references provide definitions and methods known to those in the art. However, it is not intended that the present disclosures be limited to any particular methods, protocols, and reagents described, as these may vary in ways that will be understood by the skilled artisan.

Example 1

It is well established that CRISPR-Cas systems can tolerate 'self' spacer elements within the CRISPR locus DNA via sequence discrimination at the flanking repeats. For type I and type II systems, this requires that short sequences which license targeting, known as protosopacer adjacent motifs (PAMs), are absent from the repeat sequences flanking each spacer[10,11]. For type III systems, targeting is prevented by excessive base pairing between the repeat-derived crRNA tag and its corresponding DNA sequence[12] Tolerance to 'non-self' DNA elements, on the other hand, has yet to be described. Previous reports indicate that active CRISPR-Cas systems and their targets cannot co-exist in the same cell[6,13,14]. Thus, CRISPR-Cas targeting that relies strictly on DNA sequence recognition does not offer the flexibility to accommodate genetic elements with ambiguous fitness costs, such as temperate phages. Upon infection, temperate phages can kill the host cell by initiating a lytic cycle, but they may also spare the cell from lysis and establish a lysogenic cycle, typically via repression of lytic genes and integration into the host chromosome as a so-called prophage[15]. In addition to preventing lysis, lysogenization can result in a variety of phenotypic outcomes which can improve host fitness, for example via expression of non-viral 'moron' genes carried on temperate phage genomes[4,5]. The lysis/lysogeny decision is generally governed by a central promoter region which responds to stochastic and environmental factors to control transcription in divergent directions, thereby promoting one or the other infection cycle[15]. Under certain conditions, the prophage can re-initiate a lytic cycle and excise from the chromosome—a process referred to as prophage induction. Commitment to either the lytic or lysogenic cycle does not involve changes in the viral genome sequence. Hence, it was generally accepted that CRISPR-Cas targeting of temperate phages should exclude both infection outcomes; in addition to preventing lysis, CRISPR attack of an integrated prophage target precludes stable lysogenization. Although this appears to be the case for type I-E (ref. 6) and II-A (ref. 16) CRISPR-Cas systems, the potential for tolerance during type III immunity had not been explored.

Figure 5:
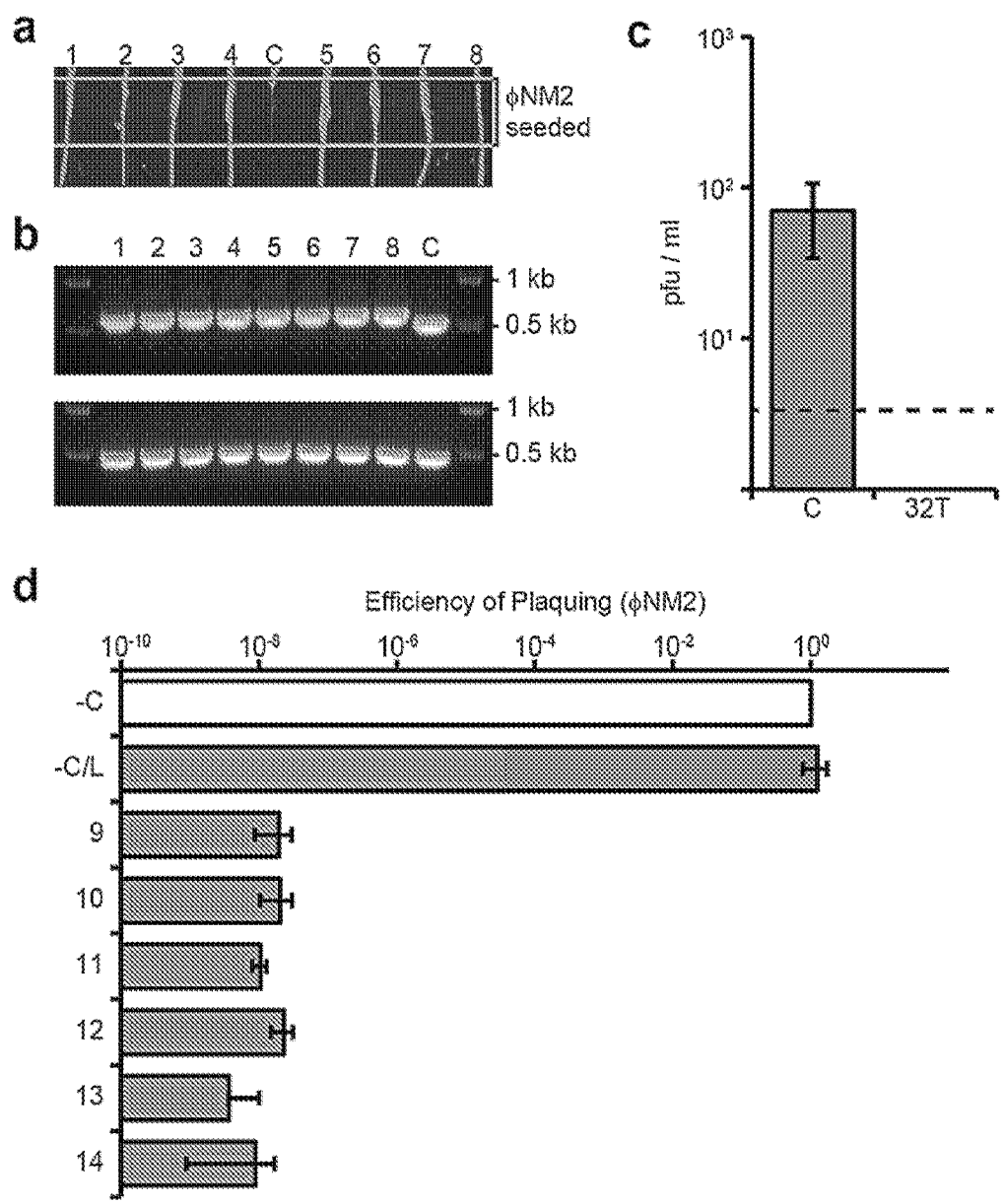
FIG. 5. Characterization of spacer 32T isolates lysogenized with ΦNM1-Erm^R. a, ΦNM2 sensitivity assay. Eight randomly selected ΦNM1-Erm^R lysogen clones were re-streaked through the indicated ΦNM2-seeded region from top to bottom (1-8); C, sensitive ΦNM1-Erm^R lysogen harboring the pGG3 control plasmid. b, PCR amplification of the CRISPR array (upper panel) and spacer 32T target region (lower panel) for the strains tested in a. The pGG3 control lysogen (C) lacks a phage-targeting spacer in its CRISPR array. 1 kb and 0.5 kb size markers are indicated. All 8 PCR products for the target region were sequenced by the Sanger method and no mutations were found (data not shown). c, Plaque-forming potential of filtered supernatants from spacer 32T lysogen overnight cultures inoculated in triplicate. Plaque-forming units (pfu) were enumerated on soft agar lawns of RN4220 harboring either the pGG3 control (C) or spacer 32T CRISPR plasmids. Dotted line represents the limit of detection for this assay. d, ΦNM2 plaquing efficiency on soft agar lawns of an additional six randomly selected ΦNM1-Erm^R lysogen clones isolated during infection of RN4220/spacer 32T (9-14); a ΦNM1-Erm^R lysogen harboring the pGG3 control plasmid was also tested (−C/L). Plaquing efficiency on the non-lysogenic indicator strain harboring pGG3 is shown for comparison (−C).
Figure 6:
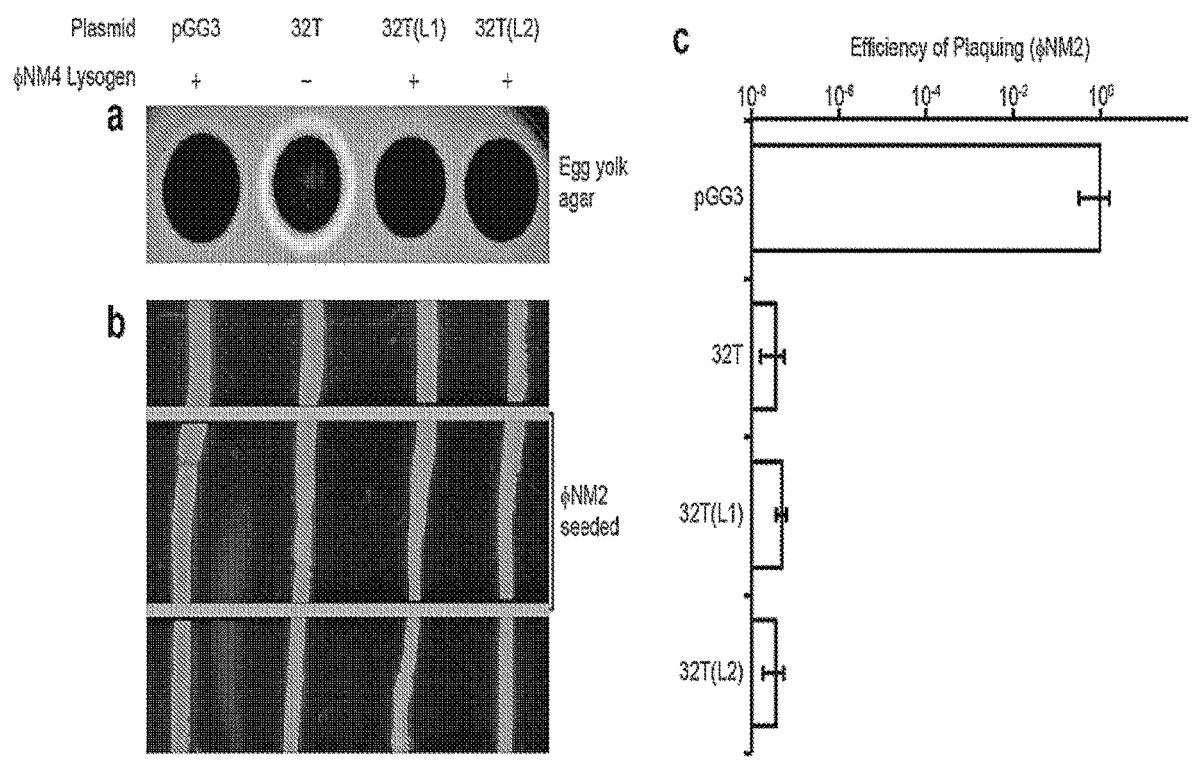
FIG. 6. Characterization of spacer 32T isolates lysogenized with ΦNM4. a, Visualization of TB4-derived strains grown on egg-yolk agar. Integration of ΦNM4 within the geh locus of TB4 results in strongly reduced lipase secretion, enabling a screen for ΦNM4 lysogenization with spacer 32T. Right-most lanes represent two lipase-negative isolates from the lysogenization screen. b, ΦNM2 sensitivity assay. Strains shown in panel a were re-streaked through the indicated ΦNM2-seeded region from top to bottom. The pGG3 lysogen and spacer 32T non-lysogen in the two left-most lanes serve as sensitive and insensitive controls, respectively. c, ΦNM2 plaquing efficiency on soft agar lawns of the strains analyzed in panels a and b. 32T(L1) and 32T(L2) refer to the two ΦNM4 lysogens isolated during the spacer 32T egg-yolk screen.

In order to investigate the behavior of type III CRISPR immunity during temperate phage infection, we introduced pGG3, a plasmid carrying the type III-A CRISPR-Cas system of *Staphylococcus epidermidis* RP62a (ref. 17), into *Staphylococcus aureus* RN4220 (ref. 18). This strain is sensitive to the lambda-like temperate phages of *S. aureus* Newman, a clinical isolate harboring four heteroimmune prophages (ΦNM1-4) which carry genes that enhance the pathogenicity of their host[19]. We also identified a spacer in one of the CRISPR loci of *S. aureus* MSHR1132 (ref. 20) with near-perfect identity to a conserved target sequence present in ΦNM1 (FIG. 1a), ΦNM2, and ΦNM4. This spacer, referred to as 32T (Table 1), was added to the CRISPR locus of pGG3. Using ΦNM1, we first established that this spacer prevents lytic infection by showing that plaquing efficiency is reduced approximately seven orders of magnitude when compared to a strain carrying the pGG3 plasmid without the ΦNM1-targeting spacer (FIG. 1b). We then introduced an erythromycin resistance gene (ermC) into ΦNM1 to facilitate quantification of lysogens which have stably integrated a chromosomal prophage (creating (ΦNM1-Erm$^R$). Using this system, we expected to find results consistent with a report describing CRISPR-mediated immunity to lysogenization by phage lambda in *E. coli*[6]. Surprisingly, we obtained the same efficiency of lysogenization compared to the control strain lacking spacer 32T (FIG. 1c). To test whether the presence of mismatches between the 32T crRNA and its target was influencing this phenomenon, we engineered spacer 32T* with a perfect match to its target, but obtained the same results (FIGS. 1b and c). We next sought to determine whether genetic CRISPR-Cas inactivation is responsible for the apparent tolerance of these lysogens by testing them for sensitivity to ΦNM2. All 14 clones maintained resistance to ΦNM2 mediated by spacer 32T (FIG. 5a, d). Finally, we demonstrated that spacer 32T tolerance does not result from genetic alteration of the target phage (FIG. 5b, c). Tolerance was also observed for ΦNM4 (FIG. 5), demonstrating that the tolerance phenomenon is not specific for the ΦNM1-Erm$^R$ phage or its integration locus. These results demonstrate that type III-A CRISPR immunity can block lytic infection but tolerate lysogenization without concomitant genetic CRISPR-Cas inactivation or alteration of the phage genome.

Figure 2:
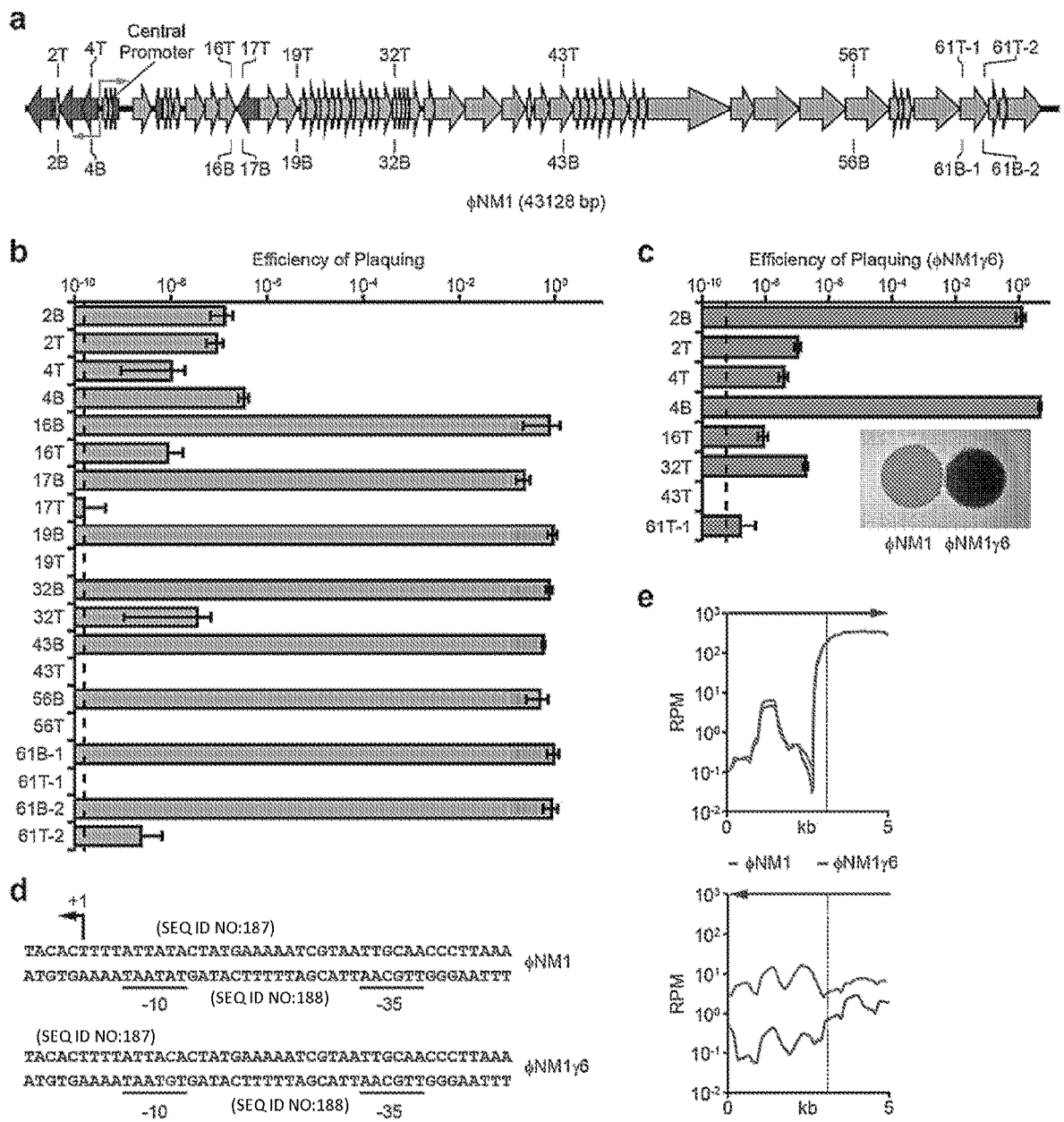
FIG. 2. Transcription of target sequences is required for type III-A CRISPR immunity. a, Schematic diagram of the ΦNM1 genome and the position of targets used in this study. T, crRNA anneals to the top strand; B, bottom strand. Gray arrows represent the ΦNM1 central promoter driving divergent transcription. b, Immunity against ΦNM1 infection provided by spacers targeting the phage regions shown in a. Dotted line indicates the limit of detection for the assay. c, Immunity against ΦNM1γ6 infection. Inset; comparison of plaque phenotypes for ΦNM1 (turbid) and ΦNM1γ6 (clear). d, Leftward promoter consensus sequences at the ΦNM1 and ΦNM1γ6 central promoter. The ΦNM1γ6 mutation in the −10 element is shown in red. The putative transcription start site is noted (+1). e, Comparison of phage transcription profiles from cells infected with ΦNM1 (gray line) or ΦNM1γ6 (red line), 15 minutes post-infection. Phage-derived transcripts are plotted in reads per million total-mapped reads (RPM) relative to their position on the genome; arrows indicate the direction of transcription plotted in each graph; the vertical dotted line marks the position of the central promoter. Error bars: mean±s.d.
Figure 7:
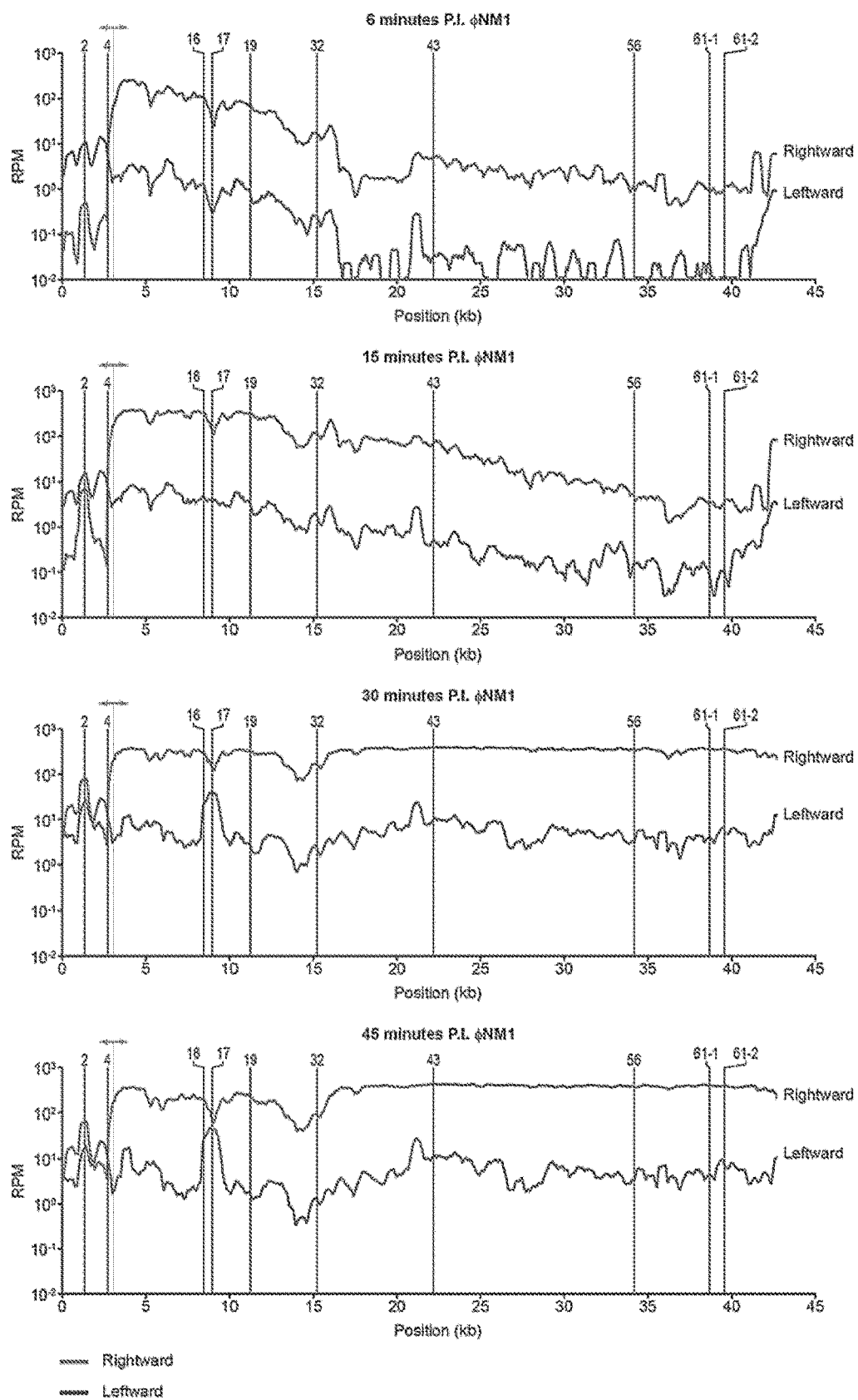
FIG. 7. Visualization of ΦNM1 transcription profiles 6, 15, 30, and 45 min post infection (MOI 20). Rightward and leftward expression values as indicated, and are provided, in reads per million (RPM). Position of relevant spacer targets are indicated with vertical solid lines. The dotted line with arrowheads marks the position of the central promoter. To improve readability, all curves were smoothened by plotting the average RPM values over a 500 bp sliding-window. To the left of the central promoter, rightward expression is comparable to leftward expression by 30 min post infection, consistent with the strand-independent targeting observed for this region.

To determine whether prophage tolerance is a spacer-specific phenomenon, we designed a variety of spacers with 100% target identity, targeting different regions of the ΦNM1 genome on both strands (FIG. 2a). We first tested the ability of each spacer to prevent lytic infection (FIG. 2b). Surprisingly, spacer functionality varied with the predicted transcriptional context of each target sequence. Spacers matching putative lytic genes to the right of the central promoter which are predicted to be unidirectionally transcribed were only effective when they targeted the predicted non-template strand (top strand according to our spacer nomenclature). Meanwhile, transcription is predicted to be bi-directional to the left of the central promoter[19]. Spacers targeting this region prevented plaque formation regardless of the strand targeted. This resembled the activity reported for the type III-B CRISPR-Cas system of the archaeon, *Sulfolobus islandicus* REY15A, where immunity to plasmid transformation depended on the presence of promoters flanking a target sequence[21]. We thus reasoned that transcription-dependent targeting could explain the discrepancies in spacer functionality. Indeed, ΦNM1 transcription profiles assessed by RNA-sequencing of RN4220 cultures 6, 15, 30, and 45 min post infection revealed predominantly unidirectional transcription to the right of the central promoter, while bi-directional transcription was detected to the left of the central promoter (FIG. 7).

Figure 8:
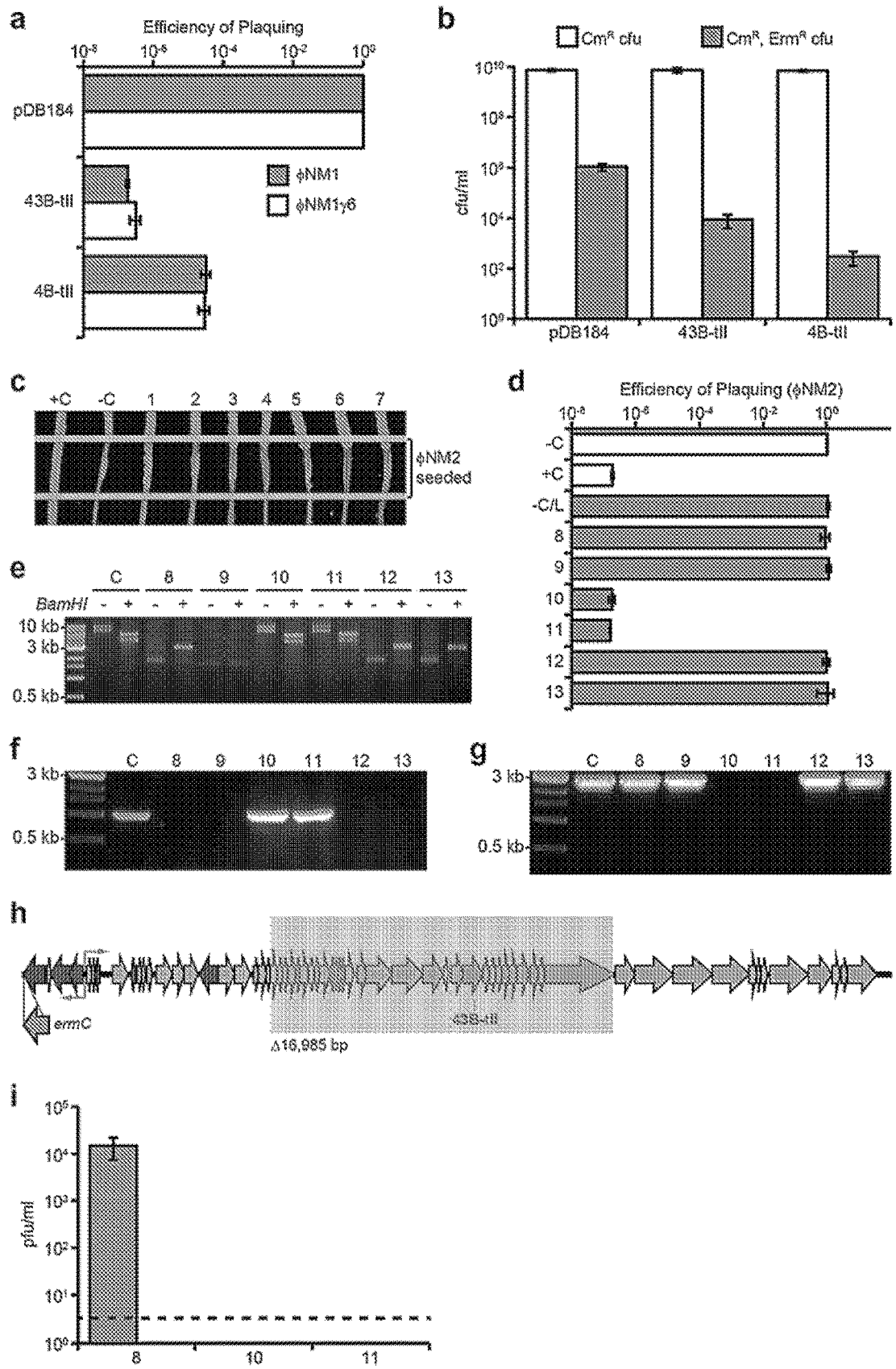
FIG. 8. Type II CRISPR-Cas targeting in S. aureus prevents both lytic and lysogenic infection. a, Plaquing efficiency of ΦNM1 and ΦNM1γ6 on lawns of RN4220 harboring type II-A CRISPR-Cas plasmids as indicated. The parental vector, pDB184, serves as a non-targeting control. b, ΦNM1-Erm^R lysogenization of RN4220 harboring either the spacer 43B-tII, 4B-tII, or non-targeting type II-A CRISPR plasmids. c, ΦNM2 sensitivity assay for seven randomly selected ΦNM1-Erm^R lysogen clones isolated during infection of RN4220/spacer 43B-tII (1-7). For comparison, a resistant non-lysogen harboring the spacer 43B-tII plasmid and a sensitive lysogen harboring the pDB184 plasmid were included as controls (respectively, C+ and C−). d, ΦNM2 plaquing efficiency on soft agar lawns for an additional six randomly selected ΦNM1-Erm^R lysogen clones isolated during infection of RN4220/spacer 43B-tII (8-13); a ΦNM1-Erm^R lysogen harboring the pDB184 plasmid is also tested (−C/L). For comparison, plaquing efficiency of ΦNM2 on the non-lysogenic indicator strain harboring pDB184 or the targeting spacer 43B-tII plasmid are also shown (−C and +C, respectively). e, Agarose gel electrophoresis of plasmid DNA purified from isolates 8-13 and the parental spacer 43B-tII strain (C). +/− indicate the presence or absence of treatment with the BamHI restriction enzyme which produces 2 bands for the wild type spacer 43B-tII plasmid: 5367 bp and 3972 bp. Size markers correspond to 10 kb, 3 kb, and 0.5 kb bands of the 1 kb DNA ladder from NEB. f, Colony PCR spanning the type II CRISPR array for isolates 8-13. Spacer 43B-tII plasmid DNA was used as a template for the control (C). 3 kb and 0.5 kb size markers are indicated. g, Colony PCR spanning the target region for isolates 8-13 and a ΦNM1-Erm$^R$ lysogen harboring the pDB184 control plasmid (C). Isolates #10 and 11 harbor identical deletions within the prophage that remove the target region (see below). 3 kb and 0.5 kb size markers are indicated. The presence of attL and attR prophage integration arms was also verified independently for each isolate using PCR (data not shown). h, Location of the 16,985 bp deletion identified within the prophage harbored by isolates #10 and 11 (shaded gray box). The location and orientation of the ermC insertion cassette is also shown (bottom arrow). Deletion was mapped by primer walking. An ~9.1 kb product spanning the deletion was ultimately amplified using primers oGG6 and oGG241, and the deletion junction was sequenced by the Sanger method using oGG245. A perfect 14 bp direct repeat micro-homology flanks the deletion. i, Plaque-forming potential of overnight culture supernatants from isolates #8, 10, and 11. Supernatants were plated by the soft agar method with RN4220 cells harboring the non-targeting pDB184 control plasmid as an indicator strain. Supernatants were also plated with spacer 43B-tII targeting lawns, yielding no detectable pfu. Isolate 8 appears to exhibit wild type levels of spontaneous prophage induction (compare to pGG3 control in FIG. 4a). No plaque-forming units were detected from the supernatants of isolates #10 and 11 whatsoever, presumably resulting from their deletion of genes essential for prophage induction, including the ORF 43 major capsid protein. Dotted line represents the limit of detection for this assay.

Further evidence for the transcription-dependence of type III-A CRISPR-Cas targeting was obtained via the characterization of a spacer 2B CRISPR-escape mutant phage, ΦNM1γ6, exhibiting a clear plaque phenotype characteristic of phages that cannot establish lysogeny (FIG. 2c, inset). Sanger sequencing of the spacer 2B target sequence did not reveal any mutations in the target or flanking sequences (data not shown), thus, we measured the ΦNM1γ6 plaquing efficiency with other spacers to determine whether it possessed a sequence-independent, general CRISPR-escape phenotype (FIG. 2c). Although most spacers provided immunity against ΦNM1γ6, we identified one additional spacer, 4B, which was escaped by the mutant phage. Both the 2B and 4B spacers target the same strand in the lysogenization operon to the left of the central promoter. Importantly, the two complementary spacers (2T and 4T) targeting the opposite strand of spacers 2B and 4B were not escaped by ΦNM1γ6, indicating that the 2B/4B escape phenotype did not result from changes to the target DNA per se. Consistent with this, we did not observe differences in the ΦNM1 and ΦNM1γ6 plaquing efficiency when targeting the 4B region via Cas9-mediated type II-A CRISPR immunity (FIG. 8a), which was shown to cleave dsDNA even in the absence of target transcription[22,23]. We thus reasoned that the ΦNM1γ6 type III-A CRISPR-escape and clear-plaque phenotypes could result from a localized, unidirectional reduction in transcription, e.g., leftward from the central promoters. Indeed, de novo sequencing of ΦNM1γ6 revealed a single nucleotide polymorphism in a crucial residue of the central promoters' leftward −10 element (FIG. 2d), immediately upstream of the SAPPVI_g4 cI-like repressor gene required for lysogenic establishment, and ~1700 bp away from the 2B target sequence. Encouraged by this result, we directly assessed ΦNM1γ6 transcription profiles using RNA-seq, 6 and 15 min post infection (FIG. 9a). Consistent with our approach, leftward transcription (FIG. 2e, lower panel) of the lysogenization operon 15 min post infection was strongly reduced, while rightward transcription (FIG. 2e, upper panel) in this region was relatively unchanged. Taken together, these findings suggest that transcription across target sequences is a requirement for type III-A CRISPR immunity. Strand-independent immunity against plasmids in *S. epidermidis* may also follow this rule, as bi-directional transcription was detected across targets (FIG. 10).

Given that temperate phages silence transcription of their lytic genes during lysogeny[15], we tested whether transcription-dependent targeting would allow a variety of otherwise effective spacers to tolerate prophage target sequences. The corollary to this prediction is that targets which are constitutively transcribed during lysogeny (e.g., leftward from the central promoter, FIG. 9b) should not be tolerated. Five additional spacers were tested for their ability to tolerate lysogenization by ΦNM1-Erm[R] (FIG. 3a). As expected, lysogenization was tolerated by spacers 17T, 43T and 61T-1 targeting lytic genes to the right of the central promoter, but not by spacers 2B and 17B targeting genes constitutively expressed leftward during lysogeny. Consistent with the notion that type III-A tolerance results from differences in transcription at the target, we did not observe tolerance with the transcription-independent type II-A CRISPR-Cas system, even when targeting a lytic gene (FIG. 8b-h). In order to rule out the possibility that type III-A tolerance is influenced by processes which occur during phage infection, we corroborated these results using a "reverse" CRISPR immunity assay by electroporating CRISPR plasmids into pre-existing lysogens. In this experiment, transformation with a targeting CRISPR-Cas system results in attack of chromosomal prophage sequences and an inability to form colonies[14]. Again, results varied with the transcriptional context of target sequences in a manner consistent with our previous findings (FIG. 3b). Collectively, these results demonstrate that prophages are not intrinsically tolerated during CRISPR immunity in staphylococci, and suggest rather that type III-A tolerance is only achieved during lysogeny under the condition that transcription is silenced at target sequences.

Figure 4:
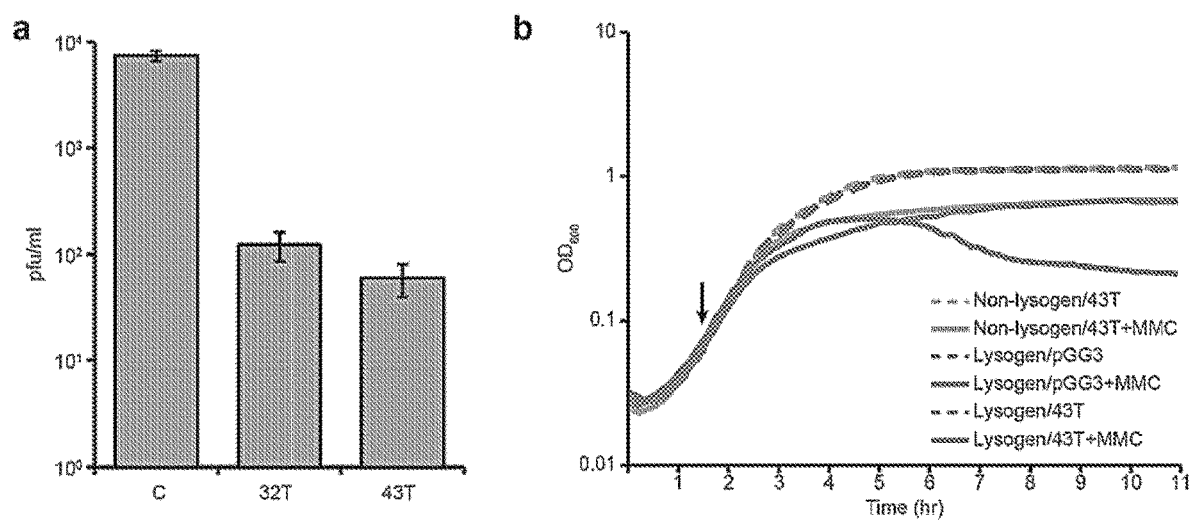
FIG. 4. Prophage induction is limited by type III-A CRISPR immunity in tolerant lysogens. a, Plaque-forming potential (measured in pfu/ml) of supernatants from overnight cultures of ΦNM1 lysogens carrying the tolerant spacer 32T or 43T CRISPR plasmids, or the pGG3 non-targeting control (C). b, Growth curve of ΦNM1-Erm^R lysogens or a non-lysogen control harboring the pGG3 or spacer 43T CRISPR plasmids as indicated, with or without the addition of the prophage-inducing agent mitomycin C (MMC) at the indicated timepoint (black arrow). Error bars: mean±s.d.

In order to definitively demonstrate that transcription-dependent targeting offers a biological mechanism for conditional tolerance, we integrated the ΦNM1 target sequence for spacers 43T and 43B into the chromosome of S. aureus RN4220 under the control of a tightly regulated tetracycline-inducible promoter, thus emulating target lysogenization. The target was placed in both orientations with respect to the inducible promoter (FIG. 3c) and with respect to the chromosomal origin of replication (FIG. 11a). The resulting strains were then transformed with the spacer 43T or 43B plasmids in a reverse CRISPR immunity assay, and plated in the absence or presence of the inducer. CRISPR immunity was only achieved when transcription across the target was induced with anhydrotetracycline in the presence of an antisense crRNA, regardless of the target's orientation (FIG. 3d and FIG. 11a). Once again, we confirmed this finding to be a type III-specific phenomenon by transforming the strains from FIG. 3c with the spacer 43B-tII type II-A CRISPR plasmid targeting the same region (FIG. 11b). We corroborated this result by following the growth of spacer 43T transformants in liquid media (FIG. 3e). Upon addition of the inducer, growth was only inhibited for cells with the target in the forward orientation for which spacer 43T produces an antisense crRNA. Importantly, tolerance achieved in the absence of the inducer did not appear to affect growth (FIG. 3e, dotted lines). Finally, having established that type III-A CRISPR-Cas systems can block lytic infection but tolerate lysogenization, we examined the effect of tolerant spacers on prophage induction of ΦNM1 lysogens in culture. Compared to a spacerless lysogen control, the phage titer resulting from spontaneous induction of overnight cultures was significantly lower for lysogens harboring a tolerant spacer (FIG. 4a). We next followed the growth of cultures induced directly with the DNA-damaging agent, mitomycin C (FIG. 4b, solid lines). While the spacerless lysogen control cultures succumbed to prophage induction, the presence of a tolerant spacer prevented lysis.

Based on the foregoing, it will be apparent that type III-A immunity can offer conditional tolerance to 'non-self' genetic elements, in this case, temperate phages. This has several important implications for the CRISPR-Cas system and its host population. Tolerance helps ensure the genetic stability of the CRISPR-Cas system, since selective pressure to integrate prophages in the presence of intolerant spacers can drive genetic CRISPR-Cas inactivation (FIG. 8c-e)—similar to what occurs during plasmid uptake[25]. In other words, tolerant spacers ensure that a population can sample potentially beneficial phenotypes that result from prophage integration without compromising their CRISPR-mediated immunity. Tolerance may also be particularly vital for type III systems, which were recently shown to provide immunity in spite of up to 15 mismatches with their spacer[26]. Thus, without the potential for phages to readily evade targeting via point mutation that is seen for type I and type II systems[10,11], the transcriptional dependence of type III-A targeting offers temperate phages an alternative route to lysogenization that need not provide selection for mutants. Furthermore, tolerant lysogens had the added potential of resisting lysis via prophage induction. Although a few spacers targeting the lysogenization functions did not provide tolerance, it is important to note that these genes only constitute a small portion of the phage genome. Hence, spacers targeting this region should be acquired less frequently even if spacer acquisition occurs randomly without an additional mechanism for distinguishing tolerant from intolerant spacers during acquisition.

The requirement for transcription across target sequences during type III-A immunity contrasts with the transcription-independent targeting reported for type I and type II CRISPR-Cas systems. Given the temporal pattern of target transcription observed during the phage lytic cycle, it might be expected that CRISPR targeting of late genes would not provide immunity if the cell's survival is already compromised at the onset of targeting. Indeed, we observed some differences in spacer effectiveness when infecting cells in liquid culture at very high MOI (~100): spacers targeting late genes were less protective (FIG. 12). However, this effect was not pronounced at a MOI of 10, suggesting that the system is generally robust to delays in target transcription, in accordance with what we observed in efficiency of plaquing assays. Consistent with our findings, our survey of sequenced staphylococcal type III spacers showed that naturally acquired spacers with known target sequences produced crRNAs complementary to the non-template strand of predicted ORFs in 9/10 cases (Table 2). This bias suggests negative selection of non-functional spacers targeting template strands. Alternatively, type III systems may utilize an unknown mechanism to discriminate template and non-template strands during spacer acquisition. Our experiments indicate that the presence of a transcript provided in trans is not sufficient to license DNA targeting (FIG. 13). Consistent with this, induction of transcription across a plasmid-borne target results specifically in loss of the targeted plasmid (FIG. 14). Hence, transcription in cis is probably required for DNA targeting. One possibility is that negative supercoiling generated in the wake of a passing transcription bubble could facilitate target DNA melting and improve crRNA recognition[27]. But this would not account for the template and non-template strand asymmetry observed in our system in this Example. Another possibility is that exposure of the target non-template strand within the transcription bubble is required for annealing of a crRNA[21]. In this scenario, the observed asymmetry might be explained by occlusion of base-pairing to the template strand by either the nascent transcript or the RNA polymerase[28]. Alternatively, transcription may be required to activate a targeting mechanism rather than facilitating target recognition or binding per se. In this case, effective targeting could require base pairing potential between the crRNA and the nascent transcript in cis, which would be absent for crRNAs with complementarity to the template strand. In summary, our work expands the repertoire of CRISPR-based immune functions to include a novel capacity for conditional tolerance of foreign elements, and establishes distinct genetic outcomes resulting from immunity to temperate phages via divergent CRISPR-Cas targeting mechanisms.

REFERENCES FOR THE FOREGOING DESCRIPTION

1 Belkaid, Y. & Hand, T. W. Role of the microbiota in immunity and inflammation. *Cell* 157, 121-141 (2014).
2 Barrangou, R. CRISPR-Cas systems and RNA-guided interference. *Wiley Interdiscip. Rev. RNA* 4, 267-278 (2013).
3 Sorek, R., Lawrence, C. M. & Wiedenheft, B. CRISPR-mediated adaptive immune systems in bacteria and archaea. *Annu. Rev. Biochem.* 82, 237-266 (2013).
4 Brüssow, H., Canchaya, C. & Hardt, W. D. Phages and the evolution of bacterial pathogens: from genomic rearrangements to lysogenic conversion. *Microbiol. Mol. Biol. Rev.* 68, 560-602 (2004).
5 Cumby, N., Davidson, A. R. & Maxwell, K. L. The moron comes of age. *Bacteriophage* 2, 225-228 (2012).
6 Edgar, R. & Qimron, U. The *Escherichia coli* CRISPR system protects from lambda lysogenization, lysogens, and prophage induction. *J. Bacteriol.* 192, 6291-6294 (2010).
7 Brouns, S. J. et al. Small CRISPR RNAs guide antiviral defense in prokaryotes. *Science* 321, 960-964 (2008).
8 Carte, J., Wang, R., Li, H., Terns, R. M. & Terns, M. P. Cas6 is an endoribonuclease that generates guide RNAs for invader defense in prokaryotes. *Genes Dev.* 22, 3489-3496 (2008).
9 Makarova, K. S. et al. Evolution and classification of the CRISPR-Cas systems. *Nat. Rev. Microbiol.* 9, 467-477 (2011).
10 Deveau, H. et al. Phage response to CRISPR-encoded resistance in *Streptococcus thermophilus*. *J. Bacteriol.* 190, 1390-1400 (2008).
11 Semenova, E. et al. Interference by clustered regularly interspaced short palindromic repeat (CRISPR) RNA is governed by a seed sequence. *Proc. Natl. Acad. Sci. U.S.A.* 108, 10098-10103 (2011).
12 Marraffini, L. A. & Sontheimer, E. J. Self versus non-self discrimination during CRISPR RNA-directed immunity. *Nature* 463, 568-571 (2010).
13 Bikard, D., Hatoum-Aslan, A., Mucida, D. & Marraffini, L. A. CRISPR interference can prevent natural transformation and virulence acquisition during in vivo bacterial infection. *Cell Host Microbe* 12, 177-186 (2012).
14 Jiang, W., Bikard, D., Cox, D., Zhang, F. & Marraffini, L. A. RNA-guided editing of bacterial genomes using CRISPR-Cas systems. *Nat. Biotechnol.* 31, 233-239 (2013).
15 Johnson, A. D. et al. lambda Repressor and cro—components of an efficient molecular switch. *Nature* 294, 217-223 (1981).
16 Nozawa, T. et al. CRISPR inhibition of prophage acquisition in *Streptococcus pyogenes*. *PLoS One* 6, e19543 (2011).
17 Hatoum-Aslan, A., Samai, P., Maniv, I., Jiang, W. & Marraffini, L. A. A ruler protein in a complex for antiviral defense determines the length of small interfering CRISPR RNAs. *J. Biol. Chem.* 288, 27888-27897 (2013).
18 Kreiswirth, B. N. et al. The toxic shock syndrome exotoxin structural gene is not detectably transmitted by a prophage. *Nature* 305, 709-712 (1983).
19 Bae, T., Baba, T., Hiramatsu, K. & Schneewind, O. Prophages of *Staphylococcus aureus* Newman and their contribution to virulence. *Mol. Microbiol.* 62, 1035-1047 (2006).
20 Holt, D. C. et al. A very early-branching *Staphylococcus aureus* lineage lacking the carotenoid pigment staphyloxanthin. *Genome Biol. Evol.* 3, 881-895 (2011).
21 Deng, L., Garrett, R. A., Shah, S. A., Peng, X. & She, Q. A novel interference mechanism by a type IIIB CRISPR-Cmr module in *Sulfolobus*. *Mol. Microbiol.* 87, 1088-1099 (2013).
22 Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci. U.S.A.* 109, E2579-2586 (2012).
23 Jinek, M. et al. A programmable dual-RNA-guided DNA endonuclease in adaptive bacterial immunity. *Science* 337, 816-821 (2012).
24 Marraffini, L. A. & Sontheimer, E. J. CRISPR interference limits horizontal gene transfer in staphylococci by targeting DNA. *Science* 322, 1843-1845 (2008).
25 Jiang, W. et al. Dealing with the evolutionary downside of CRISPR immunity: bacteria and beneficial plasmids. *PLoS Genet.* 9, e1003844 (2013).
26 Manica, A., Zebec, Z., Steinkellner, J. & Schleper, C. Unexpectedly broad target recognition of the CRISPR-mediated virus defence system in the archaeon *Sulfolobus solfataricus*. *Nucleic Acids Res.* 41, 10509-10517 (2013).
27 Westra, E. R. et al. CRISPR immunity relies on the consecutive binding and degradation of negatively supercoiled invader DNA by Cascade and Cas3. *Mol. Cell* 46, 595-605 (2012).
28 Nudler, E. RNA polymerase active center: the molecular engine of transcription. *Annu. Rev. Biochem.* 78, 335-361 (2009).
29 Hale, C. R. et al. RNA-guided RNA cleavage by a CRISPR RNA-Cas protein complex. *Cell* 139, 945-956 (2009).
30 Zhang, J. et al. Structure and Mechanism of the CMR Complex for CRISPR-Mediated Antiviral Immunity. *Mol. Cell* 45, 303-313 (2012).

The following materials and methods were used to obtain data described above.

Bacterial Strains and Growth Conditions.

Cultivation of *S. aureus* RN4220 (ref. 18), TB4 (ref. 19), and derivative strains was carried out in TSB media (BD) at 37° C., except when phage infections were performed, or when otherwise noted (see below). Whenever applicable, media were supplemented with chloramphenicol at 10 µg/ml to ensure CRISPR plasmid maintenance. RN4220 strains harboring pCL55-derived insertion vectors were grown similarly, but kanamycin was provided at 25 µg/ml except during reculture for competent cell preparation. *E. coli* DH5α was grown in LB media (BD) supplemented with kanamycin at 25-50 µg/ml to maintain pCL55-derived plasmids. Selection for (ΦNM1-Erm lysogens with resistance to erythromycin (10 µg/ml) was only applied during the lysogenization protocol as described below, and, where applicable, during the subsequent ΦNM2 sensitivity assays.

Estimation of Phage Lysate Titers.

Serial dilutions were prepared in triplicate and plated on soft agar lawns of RN4220 in HIB-agar (BD) supplemented with 5 mM $CaCl_2$. Plates were incubated at 37° C. for 16-24 hr after drying at room temperature.

DNA Preparation and Cloning.

Plasmid DNA was purified from 2-6 ml of *E. coli* DH5α or *S. aureus* RN4220 overnight cultures. For preparation from *S. aureus* cultures, cells were pelleted, resuspended in 100 µl TSM buffer (50 mM Tris-HCl pH 7.5, 10 mM $MgCl_2$, 0.5 M sucrose) and then treated with 5 µl Lysostaphin (2 mg/ml) at 37° C. for 1.5 hr before treatment with plasmid miniprep reagents from Qiagen. Purification was carried out using Qiagen or EconoSpin columns.

Cloning was performed using RN4220 electrocompetent cells unless otherwise stated. For most type III CRISPR plasmids, scarless addition of repeat-spacer units to the pGG3 parent vector was accomplished by 'round-the-horn PCR (ref. 31) followed by blunt ligation, using common primer oGG12 and spacer-specific oligos listed in Table 3. The pGG3 vector was itself constructed by 'round-the-horn PCR using primers L55 and A10 to remove extraneous repeat-spacer elements from the pWJ3013 (ref. 32) CRISPR array. For construction of the remaining type III CRISPR plasmids, a modified parent vector (pGG3-BsaI) was created by introducing a placeholder spacer harboring two BsaI restriction sites, to facilitate scarless cloning of spacers by replacement with annealed oligo pairs possessing BsaI-compatible overhangs. Type III-A CRISPR arrays were amplified with primers L50/L6 and sequenced by Sanger using either forward or reverse primers. The BsaI cloning method was also used to construct type I CRISPR plasmids from the pDB184 parent vector, a modified version of pWJ40 with only the single placeholder spacer. The pC194-derived pWJ40 vector contains the full *S. pyogenes* MIGAS type II CRISPR-Cas system and was constructed by amplifying *S. pyogenes* genomic DNA with oligos L362/W278 and pC194 with oligos W270/W282, followed by digestion of the PCR products with BglII and BssSI and a subsequent ligation. Type II CRISPR arrays were amplified with primers L448 and W176, and sequenced by Sanger using L448. After the cloning of each spacer, plasmid sizes were verified by restriction digest with BssSI for type III plasmids or BtgI for type II plasmids. pDB184 was created via Gibson assembly of two PCR fragments: a pWJ40 backbone amplified using primers B220/B334, and a CRISPR array amplified from pCas9 (ref. 14) using primers L448/B333.

For construction of pCL55-derived inducible target vectors, cloning was performed using chemically-competent DH5a cells. Briefly, the chloramphenicol resistance cassette was first replaced with a kanamycin resistance cassette amplified from strep LAM202-3 using primers L484/L485. This was accomplished by 'round-the-horn PCR on the pCL55-iTET parent vector using primers L482/L483, followed by blunt ligation with the PCR-amplified resistance cassette to create the new pKL55-iTET-B parent vector. Directionality of the insertion was verified afterwards by restriction digest with BtgI. Modification of the $P_{xyl/tet}$ promoter in accordance with pRAB 12 (ref. 33) architecture was achieved via two consecutive overlap PCR steps to introduce point mutations using oligo pairs oGG108/oGG109 and oGG110/oGG111, followed by a 'round-the-horn PCR step and blunt ligation to introduce the downstream operator sequence using oligos oGG112 and oGG113. The resulting pKL55-iTET-RC12 vector haboring the $P_{xyl/tet*}$ modifications was used for downstream manipulations, as well as integration into the RN4220 chromosome to create the "Targetless" control strain. For forward and reverse target insertions, annealed oligo pairs (oGG124/oGG125 and oGG126/oGG127, respectively) with appropriate overhangs were ligated into the multiple cloning site after digesting the vector with BglII and SacII restriction enzymes (NEB). Target insertions were verified by PCR amplification and Sanger sequencing using the primers oGG64 and oGG88. Inversion of the attP motif for both forward and reverse target vectors was achieved by Gibson assembly of two PCR fragments, using oligos oGG102/oGG103 for the attP motif and oGG104/oGG105 for the backbone. Directional integration into the RN4220 chromosome was verified by amplification of either the attL or attR junctions using primer pairs oGG50/oGG96 and oGG51/oGG96, respectively. The pWJ153 inducible target vector is a pKL55-iTET-RC12- and pE194 (ref. 34)-derived plasmid constructed via multiple steps of either 'round-the-horn PCR (ref. 31) followed by blunt ligation or Gibson assembly. The full sequence is provided as pWJ153 sequence (SEQ ID NO: 1).

Construction of the $\Phi NM1$-$Erm^R$ lysogen was achieved via pKOR allelic exchange (ref. 35). ~1 kb homology arms were amplified from the chromosome of *S. aureus* RN4220:: $\Phi NM1$ using primer pairs oGG181/oGG182 and oGG185/oGG186, while the ~1.25 kb ermC resistance cassette was amplified from a pE194 plasmid preparation using primers oGG183 and oGG184. A ~3.25 kb fragment was assembled by SOEing PCR (ref. 36) using external primers oGG181 and oGG186 with clonase (QuikChange) attB adapters that allow directional integration into the pKOR vector[35]. Sequence integrity of the ~3.25 kb insertion was verified by Sanger using primers L29, oGG191, oGG192, W277, and L325.

Preparation of Electrocompetent *S. aureus* Cells.

*S. aureus* RN4220, TB4, or derivative strains were grown overnight in TSB medium, diluted 1:100 in fresh medium without antibiotics, then allowed to grow to an $OD_{600}$ reading of 0.8-1.0 for RN4220 or 0.7-0.9 for TB4. Measurements were taken using a NanoDrop 2000c Spectrophotometer (Thermo Scientific) and disposable polystyrene cuvettes. Following reculture, cells were pelleted at 4° C., and 2-3 washes were carried out using chilled, sterile $dH_2O$ or 10% glycerol. Cells were ultimately resuspended in $\frac{1}{100}^{th}$ volume of chilled, sterile 10% glyercol and 50 µl aliquots were distributed for storage at −80° C.

Efficiency of Plaquing Assays.

High titer lysates (~$10^{12}$ pfu/ml) of either $\Phi NM1$, $\Phi NM1\gamma6$, or $\Phi NM2$ were serially diluted in triplicate and applied to soft agar lawns of RN4220 strains harboring CRISPR plasmids, including pGG3 or pDB184 spacerless control lawns infected in parallel. Plates were incubated at 37° C. for 18 hr. Following incubation, plates were monitored at bench top for up to 24 hr to facilitate quantification of plaque forming units.

Quantification of Erythromycin-Resistant Lysogens.

Overnight cultures of RN4220 with respective CRISPR plasmids were inoculated in triplicate from single colonies in HIB medium supplemented with chloramphenicol. After chilling at 4° C., 1:10 dilutions were prepared in 1 ml fresh HIB supplemented with chloramphenicol and 5 mM $CaCl_2$. Diluted cultures were infected with $\Phi NM1$-Erm at ~MOI 10 and incubated on ice for 30 min. Following incubation on ice, cultures were transferred to a 37° C. incubator for 30 min with shaking. Serial dilutions from each culture were then applied to HIB-agar plates supplemented with chloramphenicol, erythromycin, and 5 mM $CaCl_2$ for quantification of lysogenic colony forming units. In selected cases, type III-A CRISPR locus and target sequence integrity was verified by colony PCR after re-streaking single colonies using primer pairs L6/L50 (CRISPR array) and oGG25/oGG26 (ORF 2) or oGG38/oGG39 (ORF 32). Where applicable, Sanger sequencing of PCR products was also performed using these primers. When verifying type II lysogenization isolates, the spacer 43B-tII target region was amplified using primers oGG233 and oGG234, and the type II CRISPR array was amplified using L448 and W176. The presence of integrated ΦNM1 or ΦNM1-Erm$^R$ prophages was confirmed by colony PCR using primer pairs oGG191/W277 and oGG206/W276 to amplify the attL and attR junctions, respectively. In order to estimate the total number of recipient cells, serial dilutions of untreated overnight cultures were plated on TSB- or HIB-agar supplemented with chloramphenicol.

ΦNM2-Sensitivity Assay.

High-titer lysate of ΦNM2 ($10^{12}$ pfu/ml) was applied to the surface of a pre-dried HIB-agar plate supplemented with 5 mM $CaCl_2$ and appropriate antibiotics, then allowed to dry for an additional ~30 min at room temperature. Single colonies isolated from Erm lysogeny experiments or CRISPR plasmid transformations were streaked through the ΦNM2-seeded region using a sterile plastic loop and then incubated for ~12 hr at 37° C.

Enumeration of Pfu Liberated from Lysogen Cultures.

Overnight cultures of either RN4220::ΦNM1-Erm or RN4220::ΦNM1 lysogens harboring targeting CRISPR plasmids or non-targeting control plasmids were inoculated in triplicate from single colonies in HIB media supplemented with chloramphenicol. Following overnight growth, cells were transferred to 4° C. and then pelleted by centrifugation at 5000 RPM for 5 min. Supernatants were filtered, and 100 µl from each lysate was mixed with 100 µl of either an indicator strain or targeting strain overnight culture for plating by the soft agar method. After drying at room temperature, plates were incubated 18 hr at 37° C.

Screen for Lipase-Negative ΦNM4 Lysogens.

An overnight culture of S. aureus TB4 harboring the spacer 32T CRISPR plasmid was recultured to log phase growth in HIB medium supplemented with 5 mM $CaCl_2$. After measurement of $OD_{600}$, cells were treated with ΦNM4 at ~MOI 50. Following incubation for 1 hr, cells were plated on TSA supplemented with 5% egg yolk emulsion. After ~24 hr incubation at 37° C., approximately 1000 colonies were inspected for lipase secretion. Two lipase-negative candidates were re-streaked to single colonies, and the presence of an integrated ΦNM4 prophage was confirmed by colony PCR using primers oGG50 and oGG96 to amplify the attL junction.

Phage DNA Isolation and Deep Sequencing.

Samples of high titer phage lysates (~$10^{12}$ pfu/ml) were treated with DNase and RNase to a final volume of 150 µl for 1 hr at 37° C. Samples were treated with EDTA (pH 8.0) to a final concentration of 20 mM, followed by treatment with SDS to a final concentration of 0.5% and 2 µl proteinase K. Samples were incubated for 1 hr at 65° C., and then subjected to a PCR purification protocol (Qiagen). Paired-end library preparation was performed on purified phage DNA using a Nextera Tagmentation protocol (Illumina), and samples were pooled for multiplexed sequencing on a MiSeq (Illumina). De novo assembly of phage genomes was performed using ABySS (ref. 37).

RNA Preparation for RT-PCR and RNA-Seq.

For RT-PCR, overnight cultures were diluted 1:20 in 25 ml fresh media and grown for 2.5 hr at 37° C. with shaking. Following reculture, cells were pelleted and washed twice in 1 ml ice cold TSM buffer, and then treated with 3 µl Lysostaphin (2 mg/ml) for 20 min at 37° C. in 500 µl TSM buffer. Treated cells were pelleted and then resuspended in 750 µl cold TRIzol Reagent (Life Technologies) after discarding of the supernatant. The following chloroform extraction and precipitation was carried out according to the manufacturer's protocol. After resuspension in $dH_2O$, samples were treated with Qiagen DNase I for 45 min at 30° C., and then re-purified using RNeasy cleanup columns (Qiagen). In some cases, it was necessary to repeat this step a second time in order to ensure the complete removal of DNA. Following cleanup, all samples were again treated with DNase I (Sigma-Aldrich) for 30-45 min at 30° C., prior to use in the reverse transcription reaction.

For RNA-seq, overnight cultures were diluted 1:100 in fresh HIB supplemented with chloramphenicol and 500 M $CaCl_2$, and grown for 1.5 hr (approximately mid-log phase) at 37° C. with shaking. Cultures were removed, infected at MOI ~20, and then split into 10 ml portions for an additional 6, 15, 30, or 45 min of growth. Immediately following incubation, samples were mixed with 10 ml of a 1:1 acetone/ethanol solution and transferred to −80° C. The (ΦNM1 lysogen was grown similarly, except without antibiotics, and harvested immediately after the 1.5 hr reculture at 37° C. After at least one overnight at −80° C., samples were thawed on ice and pelleted by centrifugation at 5000 RPM for 10 min. After two washes of 1 ml TE buffer, cells were resuspended in 1 ml RLT buffer (Qiagen) supplemented with BME, and transferred to 2-ml tubes pre-loaded with ~0.5-1 cc of 0.1 mm glass beads (BioSpec). Samples were processed in a Mini-Beadbeater instrument (BioSpec) three times for 10 sec at 4200 oscillations/min, with 40 sec of chilling on ice between runs. After beadbeating, samples were spun down for 2 min at >13,000 RPM in a refrigerated microcentrifuge. 750 µl of supernatant was transferred to a clean tube for mixing with 500 µl of 100% ethanol, and the following RNeasy purification was carried out according to the manufacturer's protocol (Qiagen). After elution, samples were treated with either Qiagen or Sigma-Aldrich DNase I for 30-45 min at 30° C., and then re-purified using RNeasy cleanup columns. In some cases, it was necessary to repeat this step a second time to ensure the complete removal of DNA. rRNA-depleted samples were subsequently generated using the RiboZero™ Magnetic Kit for bacteria (Epicentre), according to the manufacturer's protocol.

RT-PCR.

Reverse transcription was performed using M-Mulv Reverse Transcriptase (NEB), with DNA-free total RNA isolated from RN4220 cultures harboring either the pNes (wt-d) or pNes(wt-i) plasmids as templates for cDNA synthesis. For pNes(wt-d), reverse transcription was performed with either the L8 or L86 primers in two separate 30 µl reactions, alongside mock reactions (−RT enzyme). For pNes(wt-i), the same was carried out using primers L8 or L87. Following incubation, 1 µl of each reaction was used as a template for PCR, with respective primer pairs for each sample.

Phage Transcriptome Analysis and Visualization.

Reads were aligned to reference genomes using Bowtie and sorted using Samtools. Using a custom script, sorted reads were accessed via Pysam, normalized as RPM values, and plotted in log scale as the average over consecutive windows of 500 base pairs using matplotlib tools for IPython.

Transformation Assays.

S. aureus RN4220 plasmid preps were dialyzed on 0.025 m nitrocellulose filters (Millipore) and then quantified using a NanoDrop 2000c Spectrophotometer (Thermo Scientific). 50 µl of electrocompetent cells were transformed with 80 ng dialyzed DNA using a GenePulser Xcell (BioRad) with the following parameters: 2900 V, 25 µF, 100Ω, 2 mm. After electroporation, cells were immediately resuspended in TSB to a final volume of 200 µl and recovered at 30° C. for 2 hr with shaking. Serial dilutions were then prepared before plating with appropriate antibiotics. For reverse CRISPR immunity assays targeting insertion vectors, additional plating in the presence of ATc at a final concentration of 0.5 µg/ml was performed in parallel using the same dilutions. Plates were incubated at 37° C. for 18-24 hr.

Plate Reader Growth Curves.

For ATc induction experiments, overnight cultures were launched from single colonies in triplicate and diluted 1:200 in TSB broth. Following 1 hr of growth, ATc was added at a final concentration of 0.5 µg/ml where applicable. Measurements were taken every 5 minutes. For mitomycin C induction experiments, overnight cultures were launched from single colonies in duplicate and diluted 1:100 in HIB broth. Following 1.5 h of growth, mitomycin C was added at a final concentration of 0.5 µg/ml where applicable. Measurements were taken every 10 minutes. For ΦNM1 infections, overnight cultures were launched from single colonies in triplicate and diluted 1:100 in HIB broth supplemented with $CaCl_2$ 5 mM. After 1 hr 25 min of growth, $OD_{600}$ was measured for 3 representative cultures in order to estimate MOI. Aliquots were then loaded into 96-well plates along with ΦNM1 at the appropriate MOI (10 or 100), where applicable. Measurements were taken every 5 minutes. For ΦNM1γ6 infections, overnight cultures were launched from single colonies in triplicate and diluted 1:200 in HIB supplemented with $CaCl_2$ 5 mM. An average $OD_{600}$ was measured after 1 hr of growth, and ΦNM1γ6 was added at a MOI of 10 based on this value, where applicable. Measurements were taken every 5 minutes.

Plasmid curing assay. RN4220 cells harboring both the pGG3 CRISPR-Cas plasmid and the pWJ153 target plasmid were cultured in TSB supplemented with chloramphenicol (10 ug/ml) to an OD600 of 0.45. After splitting the culture in two, transcription across the target was induced for one of the cultures via the addition of anhydrotetracycline (ATc) to a final concentration of 0.25 ug/ml. Aliquots of cells were harvested before (0) and after (1, 2, 3, 4, 5 and 6 hours) the time of induction. Following purification of DNA, plasmids were linearized with the common single cutter BamHI and subjected to agarose gel electrophoresis. In parallel, serial dilutions of both cultures were prepared in triplicate for each time point and plated on TSA plates supplemented with chloramphenicol and erythromycin or chloramphenicol alone, for quantification of antibiotic-resistant cfu.

METHODS REFERENCES

31 Moore, S. D. & Prevelige, P. E., Jr. A P22 scaffold protein mutation increases the robustness of head assembly in the presence of excess portal protein. *J. Virol.* 76, 10245-10255 (2002).
32 Hatoum-Aslan, A., Maniv, I., Samai, P. & Marraffini, L. A. Genetic Characterization of Antiplasmid Immunity through a Type III-A CRISPR-Cas System. *J. Bacteriol.* 196, 310-317 (2014).
33 Helle, L. et al. Vectors for improved Tet repressor-dependent gradual gene induction or silencing in *Staphylococcus aureus*. *Microbiology* 157, 3314-3323 (2011).
34 Horinouchi, S. & Weisblum, B. Nucleotide sequence and functional map of pE194, a plasmid that specifies inducible resistance to macrolide, lincosamide, and streptogramin type B antibodies. *J. Bacteriol.* 150, 804-814 (1982).
35 Bae, T. & Schneewind, O. Allelic replacement in *Staphylococcus aureus* with inducible counter-selection. *Plasmid* 55, 58-63 (2006).
36 Horton, R. M. In vitro recombination and mutagenesis of DNA: SOEing together tailor-made genes. *Methods Mol. Biol.* 15, 251-261 (1993).
37 Simpson, J. T. et al. ABySS: a parallel assembler for short read sequence data. *Genome Res.* 19, 1117-1123 (2009).

TABLE 1

Spacers constructed in this disclsoure.

| Spacer[a] | Sequence (5'-3')[b] | Coordinates[c] | Gene function[d] | Plasmid Name | |
|---|---|---|---|---|---|
| 2T | AATTTTTAATTTAAGTTCTTGTTCATCGTCATAAA | 1319-1353 | Excisionase | pGG52 | (SEQ ID NO: 10) |
| 2B | TATTTATGACGATGAACAAGAACTTAAATTAAAAA | 1317-1351 | Excisionase | pGG9 | (SEQ ID NO: 11) |
| 4T | AATTTCGAGGAAGTTGCAATTGATAATGAAAAATT | 2706-2740 | Repressor | pGG31 | (SEQ ID NO: 12) |
| 4B | AATTTTTCATTATCAATTGCAACTTCCTCGAAATT | 2706-2740 | Repressor | pGG30 | (SEQ ID NO: 13) |
| 4B-tII | GAAATTTCCAGCAGAAACTTTACCGAAATA | 2735-2764 | Repressor | pGG51 | (SEQ ID NO: 14) |
| 16T | CATTTTGTTTCTGTTCATGCCTCTGCCGACTGCT | 8527-8560 | Hyp. protein | pGG19 | (SEQ ID NO: 15) |
| 16B | AGCAGTCGGCAGAGGCATGAACAGAAACAAAATG | 8527-8560 | Hyp. protein | pGG4 | (SEQ ID NO: 16) |
| 17T | TAATAAGTTTTATGCTCCTCAGTTTTTAAATCACTT | 9045-9080 | Hyp. protein | pGG60 | (SEQ ID NO: 17) |
| 17B | AAGTGATTTAAAAACTGAGGAGCATAAAACTTATTA | 9045-9080 | Hyp. protein | pGG59 | (SEQ ID NO: 18) |
| 19T | TTTTTAAAAATTCTTTGGTTACCATGCATCTCGCT | 11293-11327 | Replication | pGG53 | (SEQ ID NO: 19) |
| 19B | AGCGAGATGCATGGTAACCAAAGAATTTTTAAAAA | 11293-11327 | Replication | pGG10 | (SEQ ID NO: 20) |
| 32T | TTAAATCTTTGATTGCTCTTAGCTCTAGTTATGTAT | 15352-15387 | Hyp. protein | pGG12 | (SEQ ID NO: 21) |
| 32T* | GTAAACCTTTGATTGCTCTTAGCTCGAGTTATGTGC | 15352-15387 | Hyp. protein | pGG13 | (SEQ ID NO: 22) |
| 32B | ATACATAACTAGAGCTAAGAGCAATCAAAGATTTAA | 15352-15387 | Hyp. protein | pGG36 | (SEQ ID NO: 23) |
| 43T | ATTCGTCATCTTCAAGTAATGCCTCTAAATCAATAA | 22411-22446 | Head protein | pGG41 | (SEQ ID NO: 24) |

TABLE 1-continued

Spacers constructed in this disclsoure.

| Spacer[a] | Sequence (5'-3')[b] | Coordinates[c] | Gene function[d] | Plasmid Name | |
|---|---|---|---|---|---|
| 43B | TTATTGATTTAGAGGCATTACTTGAAGATGACGAAT | 22411-22446 | Head protein | pGG40 | (SEQ ID NO: 25) |
| 43B-tII | ACTTCACACAAGATAACATTATTGATTTAG | 22393-22422 | Head protein | pGG37-full | (SEQ ID NO: 26) |
| 56T | GCATGCACCTTGCCTGAATGTTTTAAAAATTCATT | 34512-34546 | Hyp. protein | pGG54 | (SEQ ID NO: 27) |
| 56B | AATGAATTTTTAAAACATTCAGGCAAGGTGCATGC | 34512-34546 | Hyp. protein | pGG11 | (SEQ ID NO: 28) |
| 61T-1 | ATGTCACCTAAGTCAACACCATCATTTTTTATTCT | 39013-39047 | Tail fiber | pGG17 | (SEQ ID NO: 29) |
| 61B-1 | CTTAGGTGACATTGGCTGTCGATTTTACACTGAAG | 39036-39070 | Tail fiber | pGG15 | (SEQ ID NO: 30) |
| 61T-2 | TTATGATTTTTTGGAGCATATAAATCATTTAGTGT | 39949-39983 | Tail fiber | pGG18 | (SEQ ID NO: 31) |
| 61B-2 | CAGAAAGTGTATTGCAACAGATTGGCTCAAAAGTT | 39884-39918 | Tail fiber | pGG16 | (SEQ ID NO: 32) |

[a]Numbers refer to the nearest ORF designation for ΦNM1 target sequences; crRNA complementarity to the 'Top' or 'Bottom' strand is denoted with a 'T' or 'B' spacers are specified with a '-tII' suffix.
[b]Type III spacers were chosen to avoid homology between the 5' crRNA tag and the target flanking sequences, which was shown to prevent immunity in *S. epidermidis* (ref 12). Type II spacers match the nearest sequence with a 'NGG' PAM motif flanking the target's 3' end, required for Cas9-mediated immunity[10,14].
[c]Numbers reflect the coordinates of target regions for each spacer in the ΦNM1 genome (Accession: NC_008583.1).
[d]Functional assignments of the nearest ORF for each target, according to the ΦNM1 annotation (Accession: NC_008583.1).

TABLE 2

Survey of unique spacers associated with staphylococcal type III-A systems possessing known targets with five or fewer mismatches. The five or fewer mismatches is an arbitrary cutoff to provide non-limiting examples of specific spacers, but as described herein, more than five mismatches between a particular crRNA and spacer are encompassed within this disclosure.

| Organism<br>Target element | Spacer sequence<br>Target sequence | Target strand | |
|---|---|---|---|
| Staphylococcus aureus MSHR1132 | GTTTTTCATAGTTAATCAATCCCTTTTCTTTTTT | Non-template | SEQ ID NO: 183 |
| Staphylococcus phage yB_SauM_Remus | ATTAAAGTATCAAATAGTTAGGGAAAAGAAAATA | | SEQ ID NO: 33 |
| Staphylococcus aureus MSHR1132 | TATGTATTGATCTCGATTCTCGTTAGTTTCTAAATT | Non-template | SEQ ID NO: 34 |
| Staphylococcus aureus phage PHNM1 | GCACATAACTCGAGCTAAGAGCAATCAAAGGTTTAC | | SEQ ID NO: 35 |
| Staphylococcus aureus MSHR1132 | CACGCTGTAGTGAAGTATAGAAACGGCATGAGTACAAT | Non-template | SEQ ID NO: 36 |
| Staphylococcus phage SP6 | GTGCGACATCACTTCATATCTTTGCCGTACTCATGTTA | | SEQ ID NO: 37 |
| Staphylococcus epidermidis RP62a | ACGTATGCCGAAGTATATAAATCATCAGTACAAAG | Template | SEQ ID NO: 38 |
| Staphylococcus aureus pGO1 plasmid | TGCATACGGCTTCATATATTTAGTAGTCATGTTTC | | SEQ ID NO: 39 |
| Staphylococcus epidermidis RP62a | TAGTAATAATTGTCATTTGCATACGTTACATCGAT | Non-template | SEQ ID NO: 40 |
| Stahpylococcus phage CNPHB2 | ATCATTATTAACAGTAAACGTATACAATGTAGCTA | | SEQ ID NO: 41 |
| Staphylococcus aureus GBBA02176 | TAGAATGTTATTATCTAAGTGGTCGATGTATTCC | Non-template | SEQ ID NO: 42 |
| Staphylococcus phage S25-3 DNA | ATCCTACAATAATAGATACACCAGCTACATAAGG | | SEQ ID NO: 43 |
| Staphylococcus aureus GBBA02176 | AAGTTAACGGCATTACCTAATAAAAATATTTTAGG | Non-template | SEQ ID NO: 44 |
| Staphylococcus phage S13 DNA | TTCAACTGGCGTAATGGATTATTTTTGTAAAATCC | | SEQ ID NO: 45 |
| Staphylococcus aureus GBBA02176 | TCATCTTTCATGTCACTGATTAATTCATTTGTA | Non-template | SEQ ID NO: 46 |
| Staphylococcus sp. CDC3 plasmid SAP020A | AGTAGAAAGTATAGTAACTAATTAAGTAAACAT | | SEQ ID NO: 47 |
| Staphylococcus intermedius NCTC 11048 | CCAAACCATTTAGCACGATATTTATTAAAACCATA | Non-template | SEQ ID NO: 48 |
| Staphylococcus phage K | GGTTTGGTAAACCGTGCTATAAATAATTTAGGCAT | | SEQ ID NO: 49 |

TABLE 2-continued

Survey of unique spacers associated with staphylococcal type III-A systems possessing known targets with five or fewer mismatches. The five or fewer mismatches is an arbitrary cutoff to provide non-limiting examples of specific spacers, but as described herein, more than five mismatches between a particular crRNA and spacer are encompassed within this disclosure.

| Organism<br>Target element | Spacer sequence<br>Target sequence | Target<br>strand | |
|---|---|---|---|
| Staphylococcus intermedius NCTC 11048 | TATTTTTCTCCTTTAGCAATCATTCTGTCTAGTAC<br>\|\|\|\|  \|\|\|\|\|\|  \|\|\|\|\|\|\|\|\|\|\|\|\|\|\|\|\|\|\|  \|\|\| | Non-<br>template | SEQ ID NO: 50 |
| Staphylococccus phage S25-3 DNA | ATAACAAGAGGAAGATCGTTAGTAAGACAGATTATG | | SEQ ID NO: 51 |

Spacer-containing organisms and target elements are listed in the left column; the sequence of each spacer and its complementary target are provided in the middle column. Right column indicates whether the target strand is a template or non-template strand, inferred from annotated open reading frames. In cases where additional target elements were identifiable for a given spacer, a target element with the most available matches was chosen arbitrarily.

TABLE 3

Oligos used in this disclosure.

| Name | Sequence | Primary Purpose |
|---|---|---|
| A10 | CTTTGTACTGATGATTTATATACTTCGGCATACG (SEQ ID NO: 52) | Construction of pGG3 control/parent vector |
| L55 | TAAATCTAACAACACTCTAA (SEQ ID NO: 53) | Construction of pGG3 control/parent vector |
| L6 | AAAGGTACCAAATTTAATGGTATTTTCCTTCGC (SEQ ID NO: 54) | Type III CRISPR array verification |
| L50 | AAAAGATCTAATAATGTATTTACGCTGGGGC (SEQ ID NO: 55) | Type III CRISPR array verification |
| oGG12 | GTTCTCGTCCCCTTTTCTTCGGGGTGGGTATCGATCCTTTGTACTGATGATTTATATACTTC (SEQ ID NO: 56) | Common primer for spacer cloning via PCR |
| oGG13 | AGCAGTCGGCAGAGGCATGAACAGAAACAAAATGTAAATCTAACAACACTCTAAAAAATTG (SEQ ID NO: 57) | Construction of pGG4 |
| oGG19 | TATTTATGACGATGAACAAGAACTTAAATTAAAAATAAATCTAACAACACTCTAAAAAATTG (SEQ ID NO: 58) | Constuction of pGG9 |
| oGG20 | AGCGAGATGCATGGTAACCAAAGAATTTTTAAAAATAAATCTAACAACACTCTAAAAAATTG (SEQ ID NO: 59) | Construction of pGG10 |
| oGG21 | AATGAATTTTTAAAACATTCAGGCAAGGTGCATGCTAAATCTAACAACACTCTAAAAAATTG (SEQ ID NO: 60) | Construction of pGG11 |
| oGG22 | TTAAATCTTTGATTGCTCTTAGCTCTAGTTATGTATTAAATCTAACAACACTCTAAAAAATTG (SEQ ID NO: 61) | Construction of pGG12 |
| oGG23 | GTAAACCTTTGATTGCTCTTAGCTCGAGTTATGTGCTAAATCTAACAACACTCAAAAAATTG (SEQ ID NO: 62) | Consturction of pGG13 |
| oGG46 | CTTAGGTGACATTGGCTGTCGATTTTACACTGAAGTAAATCTAACAACACTCTAAAAAATTG(SEQ ID NO: 63) | Construction of pGG15 |
| oGG47 | CAGAAAGTGTATTGCAACAGATTGGCTCAAAAGTTTAAATCTAACAACACTCTAAAAAATTG (SEQ ID NO: 64) | Construction of pGG16 |
| oGG48 | ATGTCACCTAAGTCAACACCATCATTTTTTATTCTTAAATCTAACAACACTCTAAAAAATTG (SEQ ID NO: 65) | Construction of pGG17 |
| oGG49 | TTATGATTTTTTGGAGCATATAAATCATTTATGTTAAATCTAACAACACTCTAAAAAATTG (SEQ ID NO: 66) | Construction of pGG18 |
| oGG56 | CATTTTGTTTCTGTTCATGCCTCTGCCGACTGCTTAAATCTAACAACACTCTAAAAAATTG (SEQ ID NO: 67) | Construction of pGG19 |
| oGG84 | AATTTTTCATTATCAATTGCAACTTCCTCGAAATTTAAATCTAACAACACTCTAAAAAATTG (SEQ ID NO: 68) | Construction of pGG30 |

TABLE 3-continued

Oligos used in this disclosure.

| Name | Sequence | Primary Purpose |
|---|---|---|
| oGG85 | AATTTCGAGGAAGTTGCAATTGATAATGAAAAATTTAAATCTAACAACACTCTAAA AAATTG (SEQ ID NO: 69) | Construction of pGG31 |
| oGG101 | ATACATAACTAGAGCTAAAGCAATCAAAGATTTAATAAATCTAACAAACTCTAA AAAATTG (SEQ ID NO: 70) | Construction of pGG36 |
| oGG115 | ATTCGTCATCTTCAAGTAATGCCTCTAAATCAATAATAAATCTAACAACACTCTAA AAAATTG (SEQ ID NO: 71) | Construction of pGG41 |
| oGG121 | TAGACCAGTCTCGGAAGCTCAAAGGTCTCTTAAATCTAACAACACTCAAAAAAT TG (SEQ ID NO: 72) | Construction of pGG3-BsaI |
| oGG122 | GAACTTATTGATTTAGAGGCATTACTTGAAGATGACGAAT (SEQ ID NO: 73) | Constuction of pGG40 |
| oGG123 | TTTAATTCGTCATCTTCAAGTAATGCCTGTAAATCAATAA (SEQ ID NO: 74) | Construction of pGG40 |
| oGG175 | GAACAATTTTTAATTTAAGTTCTTGTTCATCGTCATAAA (SEQ ID NO: 75) | Construction of pGG52 |
| oGG176 | TTTATTTATGACGATGAACAAGAACTTAAATTAAAAATT (SEQ ID NO: 76) | Construction of pGG52 |
| oGG177 | GAACTTTTTAAAAATTCTTTGGTTACCATGCATCTCGCT (SEQ ID NO: 77) | Construction of pGG53 |
| oGG178 | TTTAGCGAGATGCATGGTAACCAAAGAATTTTTAAAAA (SEQ ID NO: 78) | Construction of pGG53 |
| oGG179 | GAACGCATGCACCTTGCCTGAATGTTTTAAAAATTCATT (SEQ ID NO: 79) | Construction of pGG54 |
| oGG180 | TTTAAATGAATTTTTAAAACATTCAGGCAAGGTGCATGC (SEQ ID NO: 80) | Construction of pGG54 |
| oGG225 | GAACAAGTGATTTAAAAACTGAGGAGCATAAAACTTATTA (SEQ ID NO: 81) | Construction of pGG59 |
| oGG226 | TTTATAATAAGTTTTATGCTCCTCAGTTTTTAAATCACTT (SEQ ID NO: 82) | Construction of pGG59 |
| oGG227 | GAACTAATAAGTTTTATGCTCCTCAGTTTTTAAATCACTT (SEQ ID NO: 83) | Construction of pGG60 |
| oGG228 | TTTAAAGTGATTTAAAAACTGAGGAGCATAAAACTTATTA (SEQ ID NO: 84) | Construction of pGG60 |
| L362 | AAACTCGTGGATTCTGTGATTTGGATCCTTCC (SEQ ID NO: 85) | Construction of pWJ40 |
| W278 | AAAAAGATCTTATGACTGTTATGTGGTTATCG (SEQ ID NO: 86) | Construction of pWJ40 |
| W270 | AAAAAGATCTTGCATAATTCACGCTGACCTC (SEQ ID NO: 87) | Construction of pWJ40 |
| W282 | AAAACACGAGCGTTTGTTGAACTAATGGGTGC (SEQ ID NO: 88) | Construction of pWJ40 |
| B220 | AAAAAGCGCAAGAAGAAATCAACCAGCGCACTCGTAGACTATTTTTGTCTAAA (SEQ ID NO: 89) | Construction of pDB184 |
| B334 | ACACTGAGACTTGTTGAGTTCAAACGAAAATTGGATAAAGTGGG (SEQ ID NO: 90) | Construction of pDB184 |
| L448 | ATTATTTCTTAATAACTAAAAATATGG (SEQ ID NO: 91) | Construction of pDB184 |
| B333 | CTTTATCCAATTTTCGTTTGAACTCAACAAGTCTCAGTGTGCTG (SEQ ID (NO: 92) | Construction of pDB184 |
| oGG148 | AAACACTTCACACAAGATAACATTATTGATTTAGG (SEQ ID NO: 93) | Construction of pGG37-full |
| oGG149 | AAAACCTAAATCAATAATGTTATCTTGTGTGAAGT (SEQ ID NO: 94) | Construction of pGG37-full |
| oGG166 | AAACGAAATTTCCAGCAGAAACTTTACCGAAATAG (SEQ ID NO: 95) | Constuction of pGG51 |
| oGG167 | AAAACTATTTCGGTAAAGTTTCTGCTGGAAATTTC (SEQ ID NO: 96) | Construction of pGG51 |
| oGG191 | GAAGCTTTAGCTTTGCAGTGG (SEQ ID NO: 97) | ΦNM1(-Erm) attL junction verification |
| W277 | CTGTAATAGACATCGTTCGCAG (SEQ ID NO: 98) | ΦNM1(-Erm) attL junction verification |
| oGG206 | GCTACATTAATTATAGGGAATCTTAC (SEQ ID NO: 99) | ΦNM1(-Erm) attR junction verification |
| W276 | TCCTAACAGAAATTGCGTTAAAG (SEQ ID NO: 100) | ΦNM1(-Erm) attR junction verification |

TABLE 3-continued

Oligos used in this disclosure.

| Name | Sequence | Primary Purpose |
|---|---|---|
| L8 | TTTTATACAATACTATTTATAAGTGC (SEQ ID NO: 101) | RT-PCR |
| L86 | CATATAGTTTTATGCCTAAAAACC (SEQ ID NO: 102) | RT-PCR |
| L87 | ATATATTTATTTGGCTCATATTTGC (SEQ ID NO: 103) | RT-PCR |
| L484 | AAACTCGAGCGCGCAAGCTGGGGATCCG (SEQ ID NO: 104) | Construction of pKL55-iTET-B |
| L485 | AAACTCGAGTAGGTACTAAAACAATTCATCCAG (SEQ ID NO: 105) | Construction of pKL55-iTET-B |
| L482 | AAACTCGAGCTGAGAGTGCACCATATGCGG (SEQ ID NO: 106) | Construction of pKL55-iTET-B |
| L483 | AAACTCGAGCTTAATAGCTCACGCTATGCCG (SEQ ID NO: 107) | Construction of pKL55-iTET-B |
| oGG108 | TAATTCCTCCTTTTTGTTGACATTATATCATTGATAGAGTTATTTG (SEQ ID NO: 108) | Construction of pKL55-iTET-RC12 |
| oGG109 | ACTCTATCAATGATATAATGTCAACAAAAAGGAGGAATTAATGATG (SEQ ID NO: 109) | Construction of pKL55-iTET-RC12 |
| oGG110 | TGACACTCTATCATTGATAGAGCATAATTAAAATAAGCTTGATATC (SEQ ID NO: 110) | Construction of pKL55-iTET-RC12 |
| oGG111 | AAGCTTATTTTAATTATGCTCTATCAATGATAGAGTGTCAATATTT (SEQ ID NO: 111) | Construction of pKL55-iTET-RC12 |
| oGG112 | TTGATAGAGTGATATCGAATTGGGAGGCATATC (SEQ ID NO: 112) | Construction of pKL55-iTET-RC12 |
| oGG113 | TGATAGAGAGCTTATTTTAATTATGCTCTATC (SEQ ID NO: 113) | Construction of pKL55-iTET-RC12 |
| oGG124 | GATCTCAAGATAACATTATTGATTTAGAGGCATTACTTGAAGATGACGAATTAGAAGCAAACCGC (SEQ ID NO: 114) | 'Forward' target insertion |
| oGG125 | GGTTTGCTTCTAATTCGTCATCTTCAAGTAATGCCTCTAAATCAATAATGTTATCTTGA (SEQ ID NO: 115) | 'Forward' target insertion |
| oGG126 | GATCTTTTGCTTCTAATTCGTCATCTTCAAGTAATGCCTCTAAATCAATAATGTTATCTTGCCGC (SEQ ID NO: 116) | 'Reverse' target insertion |
| oGG127 | GGCAAGATAACATTATTGATTTAGAGGCATTACTTGAAGATGACGAATTAGAAGCAAAA (SEQ ID NO: 117) | 'Reverse' target insertion |
| oGG64 | TCTTATTCAAGACAACACTTACAC (SEQ ID NO: 118) | Verification of inducible target insertions |
| oGG88 | ATCTAACATCTCAATGGCTAAGG (SEQ ID NO: 119) | Verification of inducible target insertions |
| oGG102 | CCACATACCTATATCTGCCCTTTTTCTGCCCTTTTTTATTTTTAAAG (SEQ ID NO: 120) | attP inversion |
| oGG103 | GTGTACTAAAAGGTAATCGATACGGTTATATTTATTCCC (SEQ ID NO: 121) | attP inversion |
| oGG104 | GGCAGAAAAAGGGCAGATATAGGTATGTGGTTTTGTATTGG (SEQ ID NO: 122) | attP inversion |
| oGG105 | TATAACCGTATCGATTACCTTTTAGTACACAAGTTTTC (SEQ ID NO: 123) | attP inversion |
| oGG50 | GTTAATGTTACGAATGATGAACC (SEQ ID NO: 124) | ΦNM4 and pKL55-iTET attL junction |
| oGG51 | TTGGCAAGTTCTGCACCTTTAC (SEQ ID NO: 125) | ΦNM4 and pKL55-iTET attR junction |
| oGG96 | AAGATGCAACAATGGGAACCAAG (SEQ ID NO: 126) | ΦNM4 and pKL55-iTET attL/R junctions |
| oGG25 | CTAAATGTGATATAATAAAATAAAAAG (SEQ ID NO: 127) | ORF 2 target verification |
| oGG26 | ATAAAGAACGATTCAACTATG (SEQ ID NO: 128) | ORF 2 target verification |

TABLE 3-continued

Oligos used in this disclosure.

| Name | Sequence | Primary Purpose |
|---|---|---|
| oGG38 | AAGATAAAGAATTTGCTCAAGACG (SEQ ID NO: 129) | ORF 32 target verification |
| oGG39 | TTCATCAGCTGACATTACTCAC (SEQ ID NO: 130) | ORF 32 target verification |
| oGG233 | GCAAGAGAGTTAAAAGGTATACG (SEQ ID NO: 131) | Spacer 43B-tII target amplification |
| oGG234 | CTGTATATCCTTGTATCAACTATC (SEQ ID NO: 132) | Spacer 43B-tII target amplification |
| W176 | CCTATCTGACAATTCCTGAATAG (SEQ ID NO: 133) | Type II CRISPR array amplification |
| oGG6 | TACCCTAGTTAACGTCTCTTG (SEQ ID NO: 134) | Deletion mapping |
| oGG241 | CGTTTCGGTACTTATTTCAACAC (SEQ ID NO: 135) | Deletion mapping |
| oGG245 | GTTAATTCTATGTCCATTTGTAACC (SEQ ID NO: 136) | Deletion junction sequencing |
| oGG181 | GGGGACAAGTTTGTACAAAAAAGCAGGCTATTCGAAATTGTACCTGTTTCATCTC (SEQ ID NO: 137) | ΦNM1-Erm construction |
| oGG182 | CGAAAAAGAGTGTCTTGTGATGGTATCATATCGGTATCAAATAAC (SEQ ID NO: 138) | ΦNM1-Erm construction |
| oGG183 | TGATACCGATATGATACCATCACAAGACACTCTTTTTTCGCACC (SEQ ID NO: 139) | ΦNM1-Erm construction |
| oGG184 | CTATGAACATATTTGATTAACGTATATAGATTTCATAAAGTCTAAC (SEQ ID NO: 140) | ΦNM1-Erm construction |
| oGG185 | CTTTATGAAATCTATATACGTTAATCAAATATGTTCATAGCTTGATG (SEQ ID NO: 141) | ΦNM1-Erm construction |
| oGG186 | GGGGACCACTTTGTACAAGAAAGCTGGGTCATTAGATATAAAGATGTATACGG (SEQ ID NO: 142) | ΦNM1-Erm construction |
| L29 | TACGACTCACTATAGGGG (SEQ ID NO: 143) | ΦNM1-Erm sequencing |
| oGG192 | TCTACTTAATCTGATAAGTGAGC (SEQ ID NO: 144) | ΦNM1-Erm sequencing |
| L325 | AAACCCGGGACGCAAACCGCCICTCCCC (SEQ ID NO: 145) | ΦNM1-Erm sequencing |

Example 2

This Example provides in vivo and in vitro experiments with the type III-A CRISPR-Cas system of *S. epidermidis* and demonstrates dual crRNA-guided cleavage of the target DNA and its transcripts. We show that purified Cas10-Csm complexes cleave double-stranded DNA targets. Without intending to be constrained by theory it is believed the reaction requires transcription across the target and it is inhibited by the presence of homology between the crRNA tag and the 5' target flanking sequence. The same complex is also capable of crRNA-guided RNA cleavage in vitro, and this reaction is not prevented by crRNA tag homology. In vivo, type III-A targeting of a plasmid shows degradation of the DNA upon induction of transcription across the target, as well as a precise cut of the target transcript. We also show that DNA and RNA targeting are independent events. Whereas DNA targeting requires an intact Cas10 palm polymerase domain, RNA targeting requires a nucleolytic active site in Csm3, both in vitro and in vivo. Mutations that affect DNA cleavage do not affect RNA cleavage and vice versa. Finally, in vivo experiments show that DNA, but not RNA, cleavage is required for immunity against plasmids and DNA viruses. These results consolidate all the different mechanistic observations of type III-A targeting into a single model and uncover a highly elaborated targeting strategy distinct from the type I and type II CRISPR-Cas systems described in Example 1.

CrRNA-Guided DNA Cleavage by the Cas10-Csm Complex Requires Target Transcription.

*S. epidermidis* CRISPR-Cas locus (FIG. 15A) encodes for a ribonucleoprotein complex composed of Cas10, Csm2, Csm3, Csm4, Csm5 and the crRNA guide, known as the Cas10-Csm complex. One of the crRNAs (encoded by the first spacer, spc1) matches a region of the nickase gene present in most staphylococcal conjugative plasmids (Marraffini and Sontheimer, 2008); this region was selected as the target for our in vivo and in vitro studies (FIG. 15B). We expressed these proteins in *Escherichia coli* to purify the complex to homogeneity (FIG. 15C). The complex was co-expressed with the repeat-spacer array and therefore it is loaded with the mature crRNA species that differ by increments of 6 nucleotides (FIG. 22A). The Cas10-Csm complex was incapable of cleaving a complementary ssDNA or dsDNA oligonucleotide substrates in different assay conditions (FIGS. 22B and C). In Example 1 it is demonstrated that the target sequence is required for type III-A CRISPR immunity. In order to test if target transcription facilitates DNA cleavage, we used an oligonucleotide based RNAP transcription system, where stepwise assembly of purified RNA and DNA oligonucleotides and *E. coli* RNA core polymerase can reconstitute fully functional RNAP elongation complexes (Sidorenkov et al., 1998). In this assay each oligonucleotide (the RNA primer, the template strand or the non-template strand) can be radioactively labeled prior to assembly to follow their fate in the reaction. The DNA oligonucleotides were complementary to each other and contained the nes target (36 nt complementary to the spc1 crRNA) and its flanking sequences (27 nt on each side). The elongation complex is assembled in the presence of transcription buffer containing $Mg^{2+}$ by the annealing of an RNA primer to the template strand, followed by the addition of RNAP and the annealing of the non-template strand (FIG. 15D). Assembled elongation complexes were incubated with purified Cas10-Csm and transcription was started by supplementing rNTPs. Extension of 5' radiolabeled RNA primers confirmed transcription elongation (FIG. 22D). We labeled each strand of the substrate in different experiments and analyzed the products of the reaction by denaturing PAGE and autoradiography. We detected cleavage of the non-template strand at two defined sites, only after the start of transcription by the addition of rNTPs (compare lane 3 and 4-7, FIG. 15E). Interestingly, an estimation of the cleavage sites based on the size of the product indicates that it occurred on the 3' flanking side of the target, not within the region with complementary to the crRNA (FIG. 15D). Further DNA degradation to the nucleotide level was observed with longer incubation times (FIG. 15E). The template strand, in contrast, was neither cleaved nor degraded (FIG. 15F). To unequivocally demonstrate a transcription requirement for DNA cleavage we used an RNAP elongation inhibitor, CBR703 (Artsimovitch et al., 2003). This small molecule inhibitor prevents nucleotide addition during transcription and therefore it should impair DNA cleavage by the Cas10-Csm complex (FIG. 16A). First we corroborated that the addition of CBR703 prevents efficient transcription elongation in our assay, by radiolabeling the RNA primer (FIG. 16B). When the same assay was performed using a radiolabeled non-template strand, the inhibition of transcription elongation with CBR703 prevented DNA cleavage (FIG. 16C). Altogether these results reveal the molecular mechanism of type III-A DNA targeting: transcription-dependent DNA cleavage of the non-template strand.

Genetic observations reveal an unexpected targeting mechanism for type III-A systems. First, only crRNAs complementary to the non-template strand provide efficient immunity as shown in FIGS. 23A and B and in Example 1. Second, the prevention of autoimmunity in type III-A systems, i.e. the spc1 crRNA-guided targeting of spc1 DNA in the CRISPR array, requires homology between the crRNA tag and the repeat sequences that flank the 3' end of the spacer DNA (of the targeted strand, complementary to the crRNA spacer sequence) (FIG. 23C). Presumably this is achieved by the pairing between these sequences. The development of an in vitro DNA cleavage assay allowed us test whether the lack of immunity observed in these two genetic experiments reflects an abrogation of target DNA cleavage by the Cas10-Csm complex. To test for DNA cleavage mediated by a crRNA complementary to the template strand we used an RNA primer that anneals to the top strand of our dsDNA substrate to assemble the elongation complex (FIG. 17A). Incubation with the Cas10-Csm complex in identical conditions to those that led to cleavage of the non-template strand produced no cleavage of either strand (FIG. 17B), even in the presence of target transcription (FIG. 22D). To test for DNA cleavage in the anti-autoimmunity scenario, we modified the target to introduce the corresponding repeat sequences at the 3' flank of the spc1 crRNA complementarity region (FIG. 17C). We then assembled the elongation complex and tested for cleavage of each DNA strand. We did not detect any cleavage or degradation, regardless of target transcription (FIG. 17D). This result indicates that in addition to target transcription, DNA cleavage requires mismatches between the crRNA tag and the 3' flanking region of the target, thus providing the molecular basis for the prevention of autoimmunity, a central feature of all immune systems. Mismatches between the crRNA tag, as well as between the crRNA and the spacer, are described above.

CrRNA-Guided RNA Cleavage by the Cas10-Csm Complex.

Recently it has been reported that type IIIA in *Streptococcus thermophilus* and *Thermus thermophilus* can cleave ssRNA targets (Staals et al., 2014; Tamulaitis et al., 2014), a function that allows protection against RNA viruses (Tamulaitis et al., 2014). In both of these systems, the Cas10-Csm complex cleaves RNA at multiple sites at 6 nt intervals. We also investigated the ribonuclease activity of the *S. epidermidis* complex. A 55 nt, 5' radiolabeled ssRNA substrate complementary to spc1 crRNA (FIG. 18A) was incubated with the Cas10-Csm complex in a buffer containing $Mg^{2+}$, and the reaction subjected to denaturing gel separation and autoradiography. We observed sequence specific endoribonuclease activity against the ssRNA substrate complementary to spc1 crRNA, with multiple cleavage products showing the reported 6 nt periodicity (FIGS. 18C, 24A and B). No activity was observed with a 55 nt scrambled, control RNA substrate (FIGS. 24C and D). A conserved aspartate residue in Csm3 (D32 in the *S. epidermidis* homolog) was identified to be the active site residue responsible for the endoribonuclease activity in the *S. thermophilus* and *T. thermophilus* complexes (Staals et al., 2014; Tamulaitis et al., 2014). We made the corresponding alanine substitution, D32A, purified the Cas10-Csm(Csm3$^{D32A}$) complex, and tested its activity against ssRNA substrates. The Csm3 D32A mutant impaired RNA cleavage without affecting complex assembly nor crRNA maturation (FIGS. 18D and 22A), consistent with a requirement for this conserved aspartate in the catalysis of RNA cleavage. Finally, to interrogate the importance of base pairing between the crRNA tag and the 3'-flanking sequence of the target, we used an ssRNA substrate (anti-tag nes ssRNA substrate, FIG. 18B) with a sequence complementary to the tag. PAGE analysis of the reaction products revealed that base-pairing between the 8 nt crRNA tag and the 3'-flanking sequence of the target had no effect on the ssRNA cleavage pattern (FIG. 18E). Collectively, the data in FIGS. 18 and 24 corroborate previous reports of crRNA-guided RNA cleavage by type III-A CRISPR-Cas systems. More important, together with our demonstration of DNA cleavage these findings reveal that type III-A immunity is capable of both RNA and DNA targeting.

CrRNA-Guided RNA and DNA Cleavage are Independent Activities within the Cas10-Csm Complex.

Combined with the crRNA-guided RNA cleavage, the transcription requirement for type III-A CRISPR-Cas immunity and crRNA-guided DNA cleavage opens the possibility of a mechanistic link between these two activities. For example, the RNA cleavage of the target's transcript could be required for DNA cleavage. However, because experiments with substrates containing a 3' flanking sequence capable of pairing with the crRNA tag had opposite outcomes, i.e. DNA but not RNA cleavage was affected (see above), our results suggest that these are independent cleavage activities. To test this we evaluated the DNA cleavage activity of the Cas10-Csm(Csm3$^{D32A}$) complex, incapable of RNA cleavage. The mutant generated a similar DNA cleavage pattern of the non-template strand to the wild-type complex (FIG. 19A, compare to FIG. 15E). This demonstrates that the Csm3 active site is not responsible for DNA cleavage and that DNA targeting occurs independently of RNA cleavage.

Cas10 is the largest subunit of the type III-A effector complex and contains a degenerate GGDEF motif (GGDD), resembling the palm polymerase domain of DNA/RNA polymerases and nucleotidyl cyclases (Anantharaman et al., 2010; Makarova et al., 2011a). Mutations in the palm domain of cas10 (cas10$^{G584A,G585A,D586A,D587A}$, here abbreviated cas10$^{palm}$) are required for type III-A immunity against staphylococcal plasmids. The mutant did not show defects in either crRNA maturation or Cas10-Csm complex formation, suggesting that the palm polymerase domain could play a catalytic role in plasmid targeting. To investigate this, we purified a Cas10-Csm complex with alanine substitutions of the conserved aspartate residues (Cas10$^{D586A,D587A}$-Csm) and tested it for RNA or DNA nuclease activity. Whereas the mutant complex cleaved the ssRNA substrate with a similar pattern as the wild-type complex (FIG. 19B, compare to 4C), it was defective in co-transcriptional DNA cleavage (FIG. 19C). These results demonstrate that the palm polymerase of Cas10 plays an essential role in DNA cleavage, with its two conserved aspartate residues most likely involved in catalysis. Taken together these data indicate that crRNA-guided DNA cleavage activity of type III-A CRISPR-Cas systems is independent from the crRNA-guided RNA cleavage, catalyzed by two different active sites within the Cas10-Csm complex.

Dual crRNA-Guided Cleavage of a DNA Target and its Transcripts During Type III-A CRISPR Immunity.

Although the DNA and RNA cleavage activities of the Cas10-Csm complex are independent, our data clearly indicates that type III-A CRISPR-Cas systems can cleave both DNA and RNA molecules. Moreover, the crRNAs that confer immunity and mediate DNA cleavage (which match the non-template, not the template, DNA strand) are also complementary to, and can guide cleavage of, the target transcript (FIG. 20A). It is therefore possible that type III-A CRISPR immunity results in the cleavage of both the target DNA and its transcripts. To test this we utilized an inducible immunity assay in vivo. In this assay, cells harbor a plasmid with the nes target under the control of a tetracycline-inducible promoter, the pTarget plasmid. To study the effect of a match between the 3' flanking target sequence and the crRNA tag, we generated a mutant version of pTarget with mutations upstream of the nes target that introduce this match (the pTarget$^{anti-tag}$ plasmid, FIG. 23C). Finally, the third strain tested contained pE194, an empty vector control. These cells are then transformed with a second plasmid encoding the type III-A CRISPR-Cas system (wild-type or the mutant variants Δspc1, cas10$^{palm}$ or csm3$^{D32A}$), the pCRISPR plasmid. Previous studies confirmed the heterologous expression of the Cas10-Csm complex from this plasmid (Hatoum-Aslan et al., 2013). In the absence of the inducer, anhydrotetracycline (aTc), there is no target transcription and therefore there should be no immunity against pTarget and its derivatives. Isolated transformants can be treated with aTc to induce CRISPR immunity and follow the fate of the target DNA and its transcripts (FIG. 20B). First we performed transformations and seeded plates with or without aTc to measure CRISPR immunity. In the presence of aTc (FIG. 20C), we observed high efficiency of transformation (as high as the transformation of pE194 control cells) for the introduction of pCRISPR(Δspc1), which does not express the spc1 crRNA guide, as well as for the DNA cleavage-deficient pCRISPR(cas10$^{palm}$) into cells harboring pTarget. The efficiency of transformation of cells containing the pTarget$^{anti-tag}$ with the wild-type pCRISPR was also high. In contrast, transformation of the wild-type and csm3$^{D32A}$ pCRISPR plasmids was greatly diminished in recipients harboring pTarget but not pE194 or pTarget$^{anti-tag}$. Collectively, these results demonstrate that cleavage of the DNA target, but not its transcript, is required for CRISPR immunity against plasmids. As expected, when we plated in the absence of the inducer (FIG. 20D) we measured a high efficiency of transformation for all plasmids. An exception was the transformation of the pCRISPR(csm3$^{D32A}$) plasmid into cells harboring pTarget. In this case we obtained a decrease in the number of transformants of approximately three orders of magnitude, with all of the colonies tested resulting in "escaper" mutants that either lacked the target or harbored rearranged pCRISPR(csm3$^{D32A}$) plasmids (not shown). We do not understand this gain-of-function phenotype, but we speculate that there is an increase of DNA targeting in the absence of RNA targeting, which is highly susceptible to leaky expression of the nes target in the absence of aTc. This could be due to the presence of more Cas10-Csm complexes available for DNA targeting in the absence of RNA targeting in this mutant. The reduction in transformation efficiency was not observed when pCRISPR (csm3$^{D32A}$) was transformed into pE194-containing cells or when a second, wild-type copy of csm3 was added into the assay (data not shown).

Staphylococci containing both the target and CRISPR plasmids (pCRISPR/pTarget, pCRISPR/pTarget$^{anti-tag}$, pCRISPR(Δspc1)/pTarget and pCRISPR(cas10$^{palm}$)/pTarget) obtained after transformation in the absence of aTc were further analyzed to detect DNA and/or RNA cleavage upon induction of target transcription. Transformants were grown in liquid to an $OD_{600}$~0.5 before the addition of aTc. Plasmid DNA and total RNA was extracted from cells collected at different times after transcription induction. The integrity of the plasmid DNA was observed by agarose gel electrophoresis followed by ethidium bromide staining before and after addition of aTc (FIG. 20E). The different versions of pCRISPR are not targeted and therefore serve as a loading control for each lane. While the pTarget was completely degraded in the presence of a wild-type pCRISPR, it was detected in cells containing the cas10$^{palm}$ mutation, albeit at lower levels than in cells lacking the spc1 crRNA. pTarget$^{anti-tag}$ was also intact in the presence of the wild-type pCRISPR. Analysis of pTarget degradation over time revealed the disappearance of the supercoiled plasmid (FIG. 20F). RNA cleavage was followed by primer extension of total RNA with an oligonucleotide priming downstream of the nes target transcript (FIG. 20G). Extension of the full nes transcript (171 nt) was detected in cells lacking the spc1 crRNA guide, but cleavage products were observed for wild-type and cas10$^{palm}$ CRISPR-Cas systems, with cleavage site within the nes target (FIG. 20H). Although in vitro we detected multiple cleavage sites, only the nearest downstream cleavage site is detected in vivo, most likely due to the impossibility of extending beyond the cut RNA. Cleavage of the anti-tag nes transcript was detected, although at a position that maps downstream of the target (see discussion). Altogether, these results demonstrate that cleavage of the target DNA, but not its transcripts, is required for type III-A CRISPR-Cas immunity against plasmids. More importantly, the data shows that these systems are capable of co-transcriptional DNA targeting resulting in the cleavage of both the target DNA and its transcripts.

As opposed to our plasmid experiments, in which the target transcript is not essential for plasmid replication, most viral transcripts are essential for viral propagation. Therefore we investigated if the dual DNA and RNA cleavage of the viral target DNA and its transcripts is important for anti-phage immunity. We tested the protection of staphylococci harboring different mutations in the type III-A CRISPR-Cas locus against infection by the dsDNA bacteriophage ΦNM1γ6 described in Example 1. We targeted the head protein gene gp43 (FIG. 21A) and measured cell survival (FIG. 21B). As shown in Example 1, the wild-type CRISPR-Cas system provided strong immunity. In contrast, cells containing the $cas10^{palm}$ gene succumbed to phage infection. The CRISPR-Cas systems containing the $csm3^{D32A}$ mutation, which cannot cleave the target's transcript, provided similar immunity to the wild-type system, almost indistinguishable from the protection conferred by the type II-A CRISPR-Cas system of *Streptococcus pyogenes* (incapable of RNA cleavage) targeting the same viral region (FIG. 21). These results indicate that DNA and RNA cleavage activities are independent and that the crRNA-guided RNA cleavage of the Cas10-Csm complex is not required for defense against dsDNA viruses, at least in the conditions tested.

It will be apparent from the foregoing that the immunity provided by type III-A CRISPR-Cas systems demands target transcription and that only crRNAs complementary to the non-template (coding) strand provide effective immunity (Exampel 1). In Example 2 we reconstituted DNA cleavage by the type III-A Cas10-Csm ribonucleoprotein complex in vitro, demonstrating that (i) cleavage requires the transcription of the target DNA, (ii) only crRNA guides complementary to the non-template strand can direct cleavage, (iii) pairing between the crRNA tag and the 3' flanking sequence of the target prevents cleavage, and (iv) the Cas10 palm polymerase domain is involved. Thus our biochemical results provide the molecular mechanism for basic aspects of type III-A CRISPR-Cas immunity against DNA mobile genetic elements. Intriguingly, the DNA cleavage site lies outside the target sequence complementary to the crRNA, mapping to the 3' flanking side of the target. It is possible the Cas10-Csm complex probes the base-pairing nature between the 8-nt crRNA-tag and the 3'-flanking sequence of the target, to distinguish the CRISPR array from bona fide targets and avoid cleavage of the former. Example 1 of this disclosure shows that DNA targeting requires transcription in cis. It is possible that co-transcriptional DNA cleavage may result from either the separation of both DNA strands or negative DNA supercoiling, both facilitated by translocation of the transcriptional machinery along DNA. Accumulation of negative supercoiling has been determined a requisite for DNA cleavage by the type I-E CRISPR-Cas system (Westra et al., 2012). Purification followed by mass spectrometry of the Cas10-Csm complex from staphylococci showed the absence of co-purifying RNAP subunits, suggesting the absence of a detectable interaction between both complexes. Cleavage experiments of this disclosure indicate that only the non-template strand is cleaved, raising the question of how a single-strand break in the phage DNA can result in strong immunity. Experiments using a nickase version of the dsDNA nuclease EcoRI have shown that the introduction of chromosomal DNA nicks is toxic to the cell, and even lethal in the absence of the homologous recombination repair pathway (Heitman et al., 1999). Without intending to be bound by theory, presumably the passage of a replication fork through the ssDNA break creates more severe DNA lesions that cannot be repaired by simple ligation and that induce the SOS repair system, and it is considered that a similar scenario can apply to the Cas10-Csm nickase activity on phage DNA targets: it could lead to severe DNA damage that is not repaired efficiently, preventing viral replication. In vivo, following the target plasmid after induction of CRISPR targeting, nicked nor linearized DNA was detected. Instead, we observed the disappearance of the supercoiled form of the plasmid. This may indicate that in vivo the nicked plasmid species is rapidly degraded after cleavage. In *E. coli*, and in staphylococci as well, the processivity of the major exonucleases RecBCD and RecJ can be as high as 1 kb per second (Lovett and Kolodner, 1989; Roman et al., 1992). At this rate of degradation, the nicked and/or linear forms of a small plasmid such as pTarget (4.6 kb) will be completely degraded in a few seconds and will not be detected by ethidium bromide staining of plasmids subjected to agarose gel electrophoresis. Alternatively, the Cas10-Csm complex itself could degrade the target DNA. Supporting this are our results which show that at longer incubation times the substrate's signal disappears (FIG. 15E). It is possible that ssDNA exonucleolytic activity purified *S. epidermidis* Cas10 is faster in vivo than in vitro, and could be potentially responsible for the rapid degradation of the target plasmid in vivo.

In the present disclosure it is shown that RNase activity (i) is responsible for the cleavage of target transcripts during in vivo type III-A CRISPR immunity and (ii) is not required for DNA cleavage. In vitro, cleavage is performed by Csm3 within the Cas10-Csm complex and occurs at 6-nucleotide intervals, each cut most likely executed by each of the multiple Csm3 subunits present in the complex. In vivo, primer extension detects only one cleavage, within the crRNA:transcript pairing region. This may be due to either the impossibility to extend beyond the cut site or to a lower sensitivity of the primer extension assay, which may be allowing visualization of only the most abundant cleavage products. Alternatively, cellular RNases could degrade the longer cleavage products in vivo, but not in vitro. Also, we detected different cleavage sites in the anti-tag RNA target in vitro and in vivo. In vitro the cleavage pattern is similar to that the nes RNA target, whereas in vivo the extension product is approximately 10 nucleotides shorter, corresponding to a region downstream of the target transcript, within the tag:anti-tag pairing region. It is possible that, in vivo, the RNA cleavage site is measured from the first nucleotides that form the crRNA:transcript pair (i.e., within the anti-tag region). If so, the cleavage site of the anti-tag target will be further downstream to the wild-type target, although it is not clear why this is not the case in vitro. However, the crRNA-guided RNA cleavage activity of the Cas10-Csm complex is not required for DNA cleavage in vitro and in vivo. It is considered generally that DNA cleavage protects the host from plasmids and dsDNA viruses, whereas RNA cleavage defends from ssRNA viruses. In this view, transcript cleavage could be an unintended consequence of the type III-A system's versatile nucleic acid targeting capability. Of note, $cas10^{palm}$ mutant cells, which are capable of RNA-guided RNA cleavage activity only, display a low level of immunity against phage infection (FIG. 20, compare with Δspc1 control cells). Without intending to be bound by any particular theory, it may be that CRISPR-mediated phage mRNA degradation could contribute to anti-phage immunity in certain conditions.

Again, without intending to be constrained by any particular perspective, we propose a unified molecular mechanism for all type III CRISPR-Cas systems: co-transcriptional crRNA-guided DNA and RNA targeting performed by Cas10-Csm/Cmr complexes. This is in sharp opposition to the type I and II CRISPR-Cas systems that have been studied so far, which rely strictly on DNA sequence recognition (Edgar and Qimron, 2010; Garneau et al., 2010; Jinek et al., 2012; Semenova et al., 2011). The broad target recognition capabilities of type III CRISPR-Cas systems provides a versatile immune response against many different viruses, plasmids and other mobile genetic elements that coexist with bacteria and archaea.

Experimental Procedures

Purification of Recombinant Cas10-Csm Complex from *E. coli*.

Plasmid pPS22 (Hatoum-Aslan et al., 2013) was used to express the Cas10-Csm complex in *E. coli*. To generate the csm3$^{D32A}$ mutation (in plasmid pPS086) pPS22 was used as template for PCR with two set of primers PS153/PS465 and PS154/PS466 (the sequences of all oligonucleotides used in this study are in Table 4), and the products were joined by Gibson assembly (Gibson et al., 2009). Full sequencing of the cloned DNA fragments was performed to corroborate the presence of the mutation. The cas10$^{D586A-D587A}$ mutation (in plasmid pPS096) was generated in a similar way using the sets of primers PS556/PS559 and PS557/PS558. The wild type and mutant Cas10-Csm protein complexes were purified as previously described (Hatoum-Aslan et al., 2013) with minor modifications (see Extended experimental procedures).

Oligonucleotide Substrates.

DNA and RNA oligonucleotides were purchased from IDT. They were radiolabeled at the 5' end with T4 polynucleotide kinase (NEB) and γ-$^{32}$P ATP (Perkin Elmer) in a 1×T4 polynucleotide kinase buffer at 37° C. for 1 hr in a 50 μl reaction. The ssDNA and ssRNA substrates were subjected to denaturing gel purification. The oligonucleotide bands were visualized by autoradiography and excised, eluted into 1 M Ammonium acetate pH 8, 0.2% SDS, and 20 mM EDTA at 4° C. overnight, ethanol precipitated, and resuspended in 10 mM Tris-HCl pH 8 (for DNA)/pH6.8 (for RNA), 1 mM EDTA. To generate dsDNA substrates T4 PNK was first heat inactivated (at 65° C. for 20 min), then the reactions were purified using an Illustra Microspin G50 column (GE Healthcare) to remove excess γ-$^{32}$P ATP. Duplex substrates were generated by heating annealing labeled oligonucleotides with twice-molar excess of unlabeled complementary oligonucleotides in the annealing buffer (20 mM Tris-Cl pH 7.5, 100 mM KCl, 5 mM MgCl$_2$, and 5% glycerol) at 90° C. for 10 minutes, followed by slow cooling to room temperature. Duplexes were separated from single-stranded DNA by 6% native PAGE conducted at 4° C. The duplex bands were visualized by autoradiography and excised, eluted into 10 mM Tris-HCl pH 8, 1 mM EDTA at 4° C. overnight, ethanol precipitated, and resuspended in 10 mM Tris-HCl pH 8, 1 mM EDTA. The sequences of DNA and RNA oligonucleotides used in this study are listed in Tables 4 and 5, respectively.

Transcription Coupled DNA Cleavage.

Elongation complexes (ECs) were reconstituted essentially as described in (Sidorenkov et al., 1998). Typically, 2 μl 1 pmol/μl of template strand (TS) and 1 μl of 4 pmol/l RNA oligos were mixed in 1× transcription buffer and incubated at 65° C. for 5 min, followed by gradual cooling to room temperature. After addition of 1.5 μl *E. coli* RNAP core enzyme (NEB), the reaction was incubated at 25° C. for 25-30 min and at 37° C. for 1 min. Then, 4 μl 1.25 pmol/μl non template strand (NTS) (pretreated by heating to 65° C. for 5 min, then on ice for 2 min, and finally at 37° C. for 2 min) was added and incubated for 10-15 min at 37° C. The final concentration of TS was 0.10 pmol/μl after adding supplement buffer to obtain transcription conditions. Assembled ECs were kept on ice until use. In a transcription coupled DNA cleavage assay, Cas10-Csm complex was added to a final concentration of 15 ng/μl. Transcription was initiated with the addition of 2.5 mM of RNTPs. All the reactions were performed at 37° C. For the elongation complex with labeled RNA primer, Cas10-Csm and RNTPs were added to the elongation complex in two different orders. In lanes indicated by (a); the Cas10-Csm complex was added to the elongation complex (EC) and incubated for 10 mins; prior to the addition of RNTPs. In lanes indicated by (b); RNTPs were added to the elongation complex and the reaction was incubated for 10 min; followed by the addition of the Cas10-Csm complex. For all the DNA cleavage time course experiments, RNTPs were added to the elongation complex (EC); prior to the addition of Cas10-Csm complex. After addition of Cas10-Csm, the samples were collected at timed intervals of 30 min, 1 hr, 1 hr 30 min and 2 hrs, and quenched by mixing with Proteinase K (NEB) and 20 mM EDTA. The DNA/RNA samples were then extracted using phenol-chloroform-isoamyl alcohol (25:24:1), ethanol precipitated and resuspended into loading buffer (90% formamide). The DNA products were heater at 95° C. for 5 min before loading onto the gel. Cleavage products were resolved on a 12% denaturing polyacrylamide gels containing 7 M urea and visualized by phosphorimaging (Typhoon, GE Life Sciences).

RNA Cleavage.

RNA cleavage reactions were performed at 37° C. with 0.1 pmol of 5'-radiolabeled RNA and 100 ng of Cas10-Csm complex in the reaction buffer (25 mM Tris-HCl pH 7.5, 10 mM MgCl$_2$, 2 mM TCEP). Reactions were initiated by addition of the Cas10/Csm complex. The samples were collected at timed intervals and quenched by mixing 10 μl of reaction mixture with 2× loading buffer (90% formamide, 50 mM EDTA). The reaction products were separated on a 14% denaturing PAGE and visualized by phosphorimaging (Typhoon, GE Life Sciences). $^{32}$P-5'-labeled RNA Decade marker (Ambion) was used as a size marker. To map the cleavage products, oligoribonucleotide markers were generated by RNase A (Life Technologies), RNase T1 (Life Technologies) treatment of RNA substrates for 10 min at 22° C. or by alkaline hydrolysis in 50 mM NaHCO$_3$ (pH 9.5) at 95° C. for 10 min.

Transformation. Cultivation of *S. aureus* RN4220 (ref. [20]), was carried out in tryptic soy (TS) broth at 37° C. Whenever applicable, media were supplemented with chloramphenicol at 10 μg/ml or erythromycin at 5 μg/ml to ensure pC194-[18] (pCRISPR) and pE194-derived[30] (pTarget) plasmid maintenance, respectively. Transformations were performed as described in Example 1 using 100 μl of competent cells and 500 μg of plasmid DNA. After electroporation transformants were plated on TS agar plates containing chloramphenicol and erythromycin for the selection of pCRISPR and pTarget derivatives, respectively, with or without anhydrotetracycline (aTc). Plates without aTc were incubated at 37° C. for 12 hours and plates with aTc at 37° C. for 36 hours before counting colony forming units. Construction of plasmid pCRISPR and its cas10$^{palm}$ derivative was described previously (Hatoum-Aslan et al., 2013).

The csm3$^{D32A}$ mutation was introduced into pCRISPR using pPS22 as template for two PCR reactions with two set of primers PS153/PS465 and PS154/PS466; the products were joined by Gibson assembly to generate pPS87. pTarget construction was as described in Example 1, as was pWJ153. Its pTarget$^{anti-tag}$ derivative was generated by Gibson assembly of a PCR product obtained using pWJ153 as template and primers NP36 and NP37.

Inducible CRISPR Immunity.

The experiment was performed as described in Example 1, with the following modifications. Overnight cultures were started from a single transformant colony obtained in the absence of aTc, grown in 3 ml of TS broth supplemented with chloramphenicol and erythromycin. Cultures are diluted to an OD$_{600}$~0.1 OD in 5 ml TSB with only chloramphenicol and grown for 1 hour. At this point (time zero in the assay) CRISPR targeting is induced by adding aTc to a final concentration of 0.25 µg/ml. Cells were collected at different times after induction and either plasmid DNA or total RNA was purified using a minprep kit (Qiagen) or TRIzol (Life Technologies), respectively. Primer extension assays were performed as reported elsewhere using primers A248 and A67 for the detection of target cleavage and 5S rRNA, respectively.

Phage Infections.

Infection of *S. aureus* RN4220 cells with bacteriophage (ΦNM1γ6) was performed using known techniques. The spacer targeting the gp43 gene of the phage was introduced by phosphorylating and annealing the oligonucleotides oGG250 and oGG251 and ligating them into the pGG-BsaI-R vector digested with BsaI, generating pWJ191 (wild-type type III-A pCRISPR plasmid in FIG. 20B). pGG-BsaI-R was used as the no-spacer control (Δspc1). This vector was derived from pGG3-BsaI described in Example 1 via two consecutive steps of 'round-the-horn PCR (Moore et al., 2008) followed by blunt ligation. First, spacer 1 was removed from pGG3-BsaI to create pGG-BsaI, using primers oGG164 and oGG165. Second, a downstream repeat was added using primers W845 and W846 to create pGG-BsaI-R. The cas10$^{palm}$ derivative was constructed by Gibson assembly of two PCR products: one using primers W494 and W1020 and pLM547 as template, and another using primers W1021 and W1022 and pWJ191 as template. The csm3$^{D32A}$ mutation was introduced into pCRISPR using pWJ191 as template for two PCR reactions with two set of primers PS153/PS465 and PS154/PS466; the products were joined by Gibson assembly to generate pPS87. Construction of the plasmid harboring the type II-A CRISPR-Cas system of *S. pyogenes* targeting the gp43 gene (pGG37) is described in Example 1.

Extended Experimental Procedures

Purification of Recombinant Cas10-Csm Complex from *E. coli*.

The pPS22 and pPS plasmids were transformed into *E. coli* BL21 (DE3) Rosetta 2 cells (Merck Millipore). Cultures (10 liters) were grown at 37° C. in Terrific Broth medium (Fisher Scientific) containing 100 µg/ml ampicilin and 34 µg/ml chloramphenicol until the A$_{600}$ reached 0.6. The cultures were adjusted to 0.3 mM isopropyl-1-thio-β-d-galactopyranoside and incubation was continued for 16 h at 17° C. with constant shaking. The cells were harvested by centrifugation and the pellets stored at −80° C. All subsequent steps were performed at 4° C. Thawed bacteria were resuspended in 75 ml of buffer A (50 mM Tris-HCl, pH 7.5, 350 mM NaCl, 200 mM Li$_2$SO$_4$, 20% sucrose, 10 mM Imidazole) containing two complete EDTA free protease inhibitor tablet (Roche). Triton X-100 and lysozyme were added to final concentrations of 0.1% and 0.1 mg/ml, respectively. After 1 hr, the lysate was sonicated to reduce viscosity. Insoluble material was removed by centrifugation for 30 min at 15,000 rpm in a Beckman JA-3050 rotor. The soluble extract was mixed for 1 hr with 5 ml of Ni$^{2+}$-Nitrilotriacetic acid-agarose resin (Qiagen) that had been pre-equilibrated with buffer A. The resin was recovered by centrifugation, then first washed with 50 ml of buffer A, followed by washing with 50 ml of IMAC buffer (50 mM Tris-HCl pH 7.5, 250 mM NaCl, 10% glycerol) containing 15 mM imidazole. The resin was subsequently resuspended in 10 ml of IMAC buffer containing 50 mM imidazole, and then poured into a column. The column was then eluted step-wise with 10 ml aliquots of IMAC buffer (50 mM Tris-HCl pH 7.5, 250 mM NaCl, 10% glycerol) containing 100, 200, 350 and 500 mM imidazole. The 200 mM imidazole elutes containing the complex was pooled together and dialyzed against 50 mM Tris-HCl pH 7.5, 50 mM NaCl, 10% glycerol. Subsequently the complex was purified using a 1 ml Source 15Q column (GE Life Sciences), eluting with a linear gradient of 50 mM-2 M NaCl. The peak fraction from the Source 15Q column was further purified by size exclusion chromatography using Superdex 200 10/300 GL (GE Healthcare) using buffer B (50 mM Tris-HCl pH 7.5, 5% glycerol, 150 mM NaCl).

Transcription Coupled DNA Cleavage Assay in the Presence of a Transcription Elongation Inhibitor.

The Darst Laboratory (The Rockefeller University) kindly provided the CBR703 inhibitor. Elongation complexes (ECs) were reconstituted as described in the main experimental procedure. Assembled ECs were either incubated with CBR703 (final concentration of 1 µM) or 10% DMSO at 37° C. for 10 minutes. In all cases, Cas10-Csm complex was added to a final concentration of 15 ng/µl. Transcription was initiated with the addition of 2.5 mM of RNTPs. All the following steps were performed at 37° C. For reactions containing a labeled RNA primer, rNTPs were added to the EC and the Cas10-Csm complex was added 10 minutes after transcription start. Samples were taken at 30, 60 and 120 minutes. Likewise, for the DNA cleavage time course experiments, rNTPs were added to the EC prior to the addition of Cas10-Csm complex. After addition of Cas10-Csm, the samples were collected at timed intervals of 30, 60, 90 and 120 minutes, and in control experiments where each of the components of the reaction were omitted, a single time point was taken at 120 minutes. The reactions were quenched by mixing with Proteinase K (NEB) and 20 mM EDTA. The DNA/RNA samples were then extracted using phenol-chloroform-isoamyl alcohol (25:24:1), ethanol precipitated and resuspended into loading buffer (90% formamide). The DNA products were heater at 95° C. for 5 min before loading onto the gel. Cleavage products were resolved on a 12% denaturing polyacrylamide gels containing 7 M urea and visualized by phosphorimaging (Typhoon, GE Life Sciences).

TABLE 4

DNA oligonucleotides used in this study (5'-3').

| Name | Sequence |
|---|---|
| A248 | CCTCCTTATAAAATTAGTATAATTATAGCAC (SEQ ID NO: 146) |
| A67 | GTGACCTCCTTGCCATTGTC (SEQ ID NO: 147) |
| NP36 | TATACTTCGGCATACGTGTTCTCGTTATCTTGTTCATATTTATC (SEQ ID NO: 148) |
| NP37 | GATAAATATGAACAAGATAACGAGAACACGTATGCCGAAGTATA (SEQ ID NO: 149) |
| oGG164 | TGAGACCAGTCTCGGAAGCTCAAAGGTCTCTTAAATCTAACAACACTCTAAAAAATTG (SEQ ID NO: 150) |
| oGG165 | GTTCTCGTCCCCTTTTCTTCGGGGTGGGTATCGATCCGATACTTTAACAAATGCCATC (SEQ ID NO: 151) |
| oGG250 | GAACATTCGTCATCTTCAAGTAATGCCTCTAAATCAATA (SEQ ID NO: 152) |
| oGG251 | GATCTATTGATTTAGAGGCATTACTTGAAGATGACGAAT (SEQ ID NO: 153) |
| PS153 | GGTAAATCAAAACTAACTAACAAATACATTAGTTTCCCACCTCTATCATC (SEQ ID NO: 154) |
| PS154 | GATGATAGAGGTGGGAAACTAATGTATTTGTTAGTTAGTTTTGATTTACC (SEQ ID NO: 155) |
| PS171 | TATTTAGAGAACGTATGCCGAAGTATATAAATCATCAGTACAAAGGTAAGAATCA (SEQ ID NO: 156) |
| PS172 | TGATTCTTACCTTTGTACTGATGATTTATATACTTCGGCATACGTTCTCTAAATA (SEQ ID NO: 157) |
| PS364 | GCGGTAATTTTAATGAGATATTTAGAGAACGTATGCCGAAGTATATAAATCATCAGTACAAAGGTAAGAATCACAGTAAACAGCGCGCGG (SEQ ID NO: 158) |
| PS365 | CCGCGCGCTGTTTACTGTGATTCTTACCTTTGTACTGATGATTTATATACTTCGGCATACGTTCTCTAAATATCTCATTAAAATTACCGC (SEQ ID NO: 159) |
| PS392 | GCGGCGTAGAGAACGTATGCCGAAGTATATAAATCATCAGTACAAAGGTAAGGCGGCG (SEQ ID NO: 160) |
| PS393 | CGCCGCGAATGGCCCTTTGACTACCCCCCCCCCAAGCCGCCCTTTAGAGATCGCCGC (SEQ ID NO: 161) |
| PS396 | GCGCGGCTTACCTTTGTACTGATGATTTATATACTTCGGCATACGTTCTCTAGCGGCG (SEQ ID NO: 162) |
| PS397 | CGCCGCATCTCTTTTCCCCGGCTTCCCCCCCCCCGTAGTCTTTCCCCATTCCCGCGC (SEQ ID NO: 163) |
| PS465 | GAATCTAGTATGATTGGAGCAATTGCTTCTCCTGTAGTTAGAGATTTGCAAACC (SEQ ID NO: 164) |
| PS466 | GGTTTGCAAATCTCTAACTACAGGAGAAGCAATTGCTCCAATCATACTAGATTC (SEQ ID NO: 165) |
| PS532 | GCGGTAATTTTAATGAGATAACGAGAACACGTATGCCGAAGTATATAAATCATCAGTACAAAGGTAAGAATCACAGTAAACAGCGCGCGG (SEQ ID NO: 166) |
| PS533 | CCGCGCGCTGTTTACTGTGATTCTTACCTTTGTACTGATGATTTATATACTTCGGCATACGTGTTCTCGTTATCTCATTAAAATTACCGC (SEQ ID NO: 167) |
| PS556 | CTGCTATATATTCAGGCGGTGCCGCTTTATTTTTAATCGGTGCATGG (SEQ ID NO: 168) |
| PS557 | CCATGCACCGATTAAAAATAAAGCGGCACCGCCTGAATATATAGCAG (SEQ ID NO: 169) |
| PS558 | GGCGAATTTTCAGGTTCAGGTATAAAAACAAGCTTAGG (SEQ ID NO: 170) |
| P5559 | CCTAAGCTTGTTTTTATACCTGAACCTGAAAATTCGCC (SEQ ID NO: 171) |
| W1020 | TGATAAATATAATACTCTAACGCTG (SEQ ID NO: 172) |
| W1021 | ACAGCGTTAGAGTATTATATTTATC (SEQ ID NO: 173) |

TABLE 4-continued

DNA oligonucleotides used in this study (5'-3').

| Name | Sequence | |
|---|---|---|
| W1022 | AATAACATCTTTCATTTTTCCATCC | (SEQ ID NO: 174) |
| W494 | GGGATGGAAAAATGAAAGATGTTA | (SEQ ID NO: 175) |
| W845 | CTTCGGGGTGGGTATCGATCAGAGACCTTTGAGCTTCCGAGAC | (SEQ ID NO: 176) |
| W846 | AAAAGGGGACGAGAACTAAATCTAACAACACTCTAAAAAATTG | (SEQ ID NO: 177) |

TABLE 5

RNA oligonucleotides used in this study (5'-3').

| Name | Sequence |
|---|---|
| nes_target | UGAUUCUUACCUUUGUACUGAUGAUUUAUAUACUUCGGCAUACGUUCUCUAAAUA (SEQ ID NO: 178) |
| NS_ssRNA | GCUGUUAAGUUACUCGAGCACAUCAGUGAUAGCCUUAUUCCCGCUGUGCCUAUAC (SEQ ID NO: 179) |
| nes anti-tag target | UGAUUCUUACCUUUGUACUGAUGAUUUAUAUACUUCGGCAUACGUGUUCUCGUUA (SEQ ID NO: 180) |
| EC Primer 1 | GUUUACUGUG (SEQ ID NO: 181) |
| EC Primer 2 | UUAAUGAGAU (SEQ ID NO: 182) |

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

REFERENCES FOR EXAMPLE 2

Anantharaman, V., Iyer, L. M., and Aravind, L. (2010). Presence of a classical RRM-fold palm domain in Thg1-type 3'-5' nucleic acid polymerases and the origin of the GGDEF and CRISPR polymerase domains. Biol Direct 5, 43.

Artsimovitch, I., Chu, C., Lynch, A. S., and Landick, R. (2003). A new class of bacterial RNA polymerase inhibitor affects nucleotide addition. Science 302, 650-654.

Barrangou, R., Fremaux, C., Deveau, H., Richards, M., Boyaval, P., Moineau, S., Romero, D. A., and Horvath, P. (2007). CRISPR provides acquired resistance against viruses in prokaryotes. Science 315, 1709-1712.

Barrangou, R., and Marraffini, L. A. (2014). CRISPR-Cas systems: prokaryotes upgrade to adaptive immunity. Mol Cell 54, 234-244.

Bolotin, A., Quinquis, B., Sorokin, A., and Ehrlich, S. D. (2005). Clustered regularly interspaced short palindrome repeats (CRISPRs) have spacers of extrachromosomal origin. Microbiology 151, 2551-2561.

Brouns, S. J., Jore, M. M., Lundgren, M., Westra, E. R., Slijkhuis, R. J., Snijders, A. P., Dickman, M. J., Makarova, K. S., Koonin, E. V., and van der Oost, J. (2008). Small CRISPR RNAs guide antiviral defense in prokaryotes. Science 321, 960-964.

Carte, J., Wang, R., Li, H., Terns, R. M., and Terns, M. P. (2008). Cas6 is an endoribonuclease that generates guide RNAs for invader defense in prokaryotes. Genes Dev 22, 3489-3496.

Deng, L., Garrett, R. A., Shah, S. A., Peng, X., and She, Q. (2013). A novel interference mechanism by a type IIIB CRISPR-Cmr module in Sulfolobus. Mol Microbiol 87, 1088-1099.

Deveau, H., Barrangou, R., Garneau, J. E., Labonte, J., Fremaux, C., Boyaval, P., Romero, D. A., Horvath, P., and Moineau, S. (2008). Phage response to CRISPR-encoded resistance in Streptococcus thermophilus. J Bacteriol 190, 1390-1400.

Edgar, R., and Qimron, U. (2010). The Escherichia coli CRISPR system protects from lambda lysogenization, lysogens, and prophage induction. J Bacteriol 192, 6291-6294.

Garneau, J. E., Dupuis, M. E., Villion, M., Romero, D. A., Barrangou, R., Boyaval, P., Fremaux, C., Horvath, P., Magadan, A. H., and Moineau, S. (2010). The CRISPR/Cas bacterial immune system cleaves bacteriophage and plasmid DNA. Nature 468, 67-71.

Gibson, D. G., Young, L., Chuang, R. Y., Venter, J. C., Hutchison, C. A., 3rd, and Smith, H. O. (2009). Enzymatic assembly of DNA molecules up to several hundred kilobases. Nat Methods 6, 343-345.

Hale, C. R., Zhao, P., Olson, S., Duff, M. O., Graveley, B. R., Wells, L., Terns, R. M., and Terns, M. P. (2009). RNA-guided RNA cleavage by a CRISPR RNA-Cas protein complex. Cell 139, 945-956.

Hatoum-Aslan, A., Maniv, I., and Marraffini, L. A. (2011). Mature clustered, regularly interspaced, short palindromic repeats RNA (crRNA) length is measured by a ruler mechanism anchored at the precursor processing site. Proc Natl Acad Sci USA 108, 21218-21222.

Hatoum-Aslan, A., Maniv, I., Samai, P., and Marraffini, L. A. (2014). Genetic Characterization of Antiplasmid Immunity through a Type III-A CRISPR-Cas System. J Bacteriol 196, 310-317.

Hatoum-Aslan, A., Samai, P., Maniv, I., Jiang, W., and Marraffini, L. A. (2013). A ruler protein in a complex for antiviral defense determines the length of small interfering CRISPR RNAs. J Biol Chem 288, 27888-27897.

Heitman, J., Ivanenko, T., and Kiss, A. (1999). DNA nicks inflicted by restriction endonucleases are repaired by a RecA- and RecB-dependent pathway in Escherichia coli. Mol Microbiol 33, 1141-1151.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Lovett, S. T., and Kolodner, R. D. (1989). Identification and purification of a single-stranded-DNA-specific exonuclease encoded by the recJ gene of *Escherichia coli*. Proc Natl Acad Sci USA 86, 2627-2631.

Makarova, K. S., Aravind, L., Wolf, Y. I., and Koonin, E. V. (2011a). Unification of Cas protein families and a simple scenario for the origin and evolution of CRISPR-Cas systems. Biol Direct 6, 38.

Makarova, K. S., Haft, D. H., Barrangou, R., Brouns, S. J., Charpentier, E., Horvath, P., Moineau, S., Mojica, F. J., Wolf, Y. I., Yakunin, A. F., et al. (201 lb). Evolution and classification of the CRISPR-Cas systems. Nat Rev Microbiol 9, 467-477.

Marraffini, L. A., and Sontheimer, E. J. (2008). CRISPR interference limits horizontal gene transfer in staphylococci by targeting DNA. Science 322, 1843-1845.

Marraffini, L. A., and Sontheimer, E. J. (2010). Self versus non-self discrimination during CRISPR RNA-directed immunity. Nature 463, 568-571.

Mojica, F. J., Diez-Villasenor, C., Garcia-Martinez, J., and Almendros, C. (2009). Short motif sequences determine the targets of the prokaryotic CRISPR defence system. Microbiology 155, 733-740.

Mojica, F. J., Diez-Villasenor, C., Garcia-Martinez, J., and Soria, E. (2005). Intervening sequences of regularly spaced prokaryotic repeats derive from foreign genetic elements. J Mol Evol 60, 174-182.

Moore, M. R., Gertz, R. E., Jr., Woodbury, R. L., Barkocy-Gallagher, G. A., Schaffner, W., Lexau, C., Gershman, K., Reingold, A., Farley, M., Harrison, L. H., et al. (2008). Population snapshot of emergent *Streptococcus pneumoniae* serotype 19A in the United States, 2005. J Infect Dis 197, 1016-1027.

Peng, W., Feng, M., Feng, X., Liang, Y. X., and She, Q. (2014). An archaeal CRISPR type III-B system exhibiting distinctive RNA targeting features and mediating dual RNA and DNA interference. Nucleic Acids Res.

Pourcel, C., Salvignol, G., and Vergnaud, G. (2005). CRISPR elements in Yersiniapestis acquire new repeats by preferential uptake of bacteriophage DNA, and provide additional tools for evolutionary studies. Microbiology 151, 653-663.

Ramia, N. F., Tang, L., Cocozaki, A. I., and Li, H. (2014). *Staphylococcus epidermidis* Csm1 is a 3'-5' exonuclease. Nucleic Acids Res 42, 1129-1138.

Roman, L. J., Eggleston, A. K., and Kowalczykowski, S. C. (1992). Processivity of the DNA helicase activity of *Escherichia coli* recBCD enzyme. J Biol Chem 267, 4207-4214.

Semenova, E., Jore, M. M., Datsenko, K. A., Semenova, A., Westra, E. R., Wanner, B., van der Oost, J., Brouns, S. J., and Severinov, K. (2011). Interference by clustered regularly interspaced short palindromic repeat (CRISPR) RNA is governed by a seed sequence. Proc Natl Acad Sci USA 108, 10098-10103.

Sidorenkov, I., Komissarova, N., and Kashlev, M. (1998). Crucial role of the RNA: DNA hybrid in the processivity of transcription. Mol Cell 2, 55-64.

Staals, R. H., Zhu, Y., Taylor, D. W., Kornfeld, J. E., Sharma, K., Barendregt, A., Koehorst, J. J., Vlot, M., Neupane, N., Varossieau, K., et al. (2014). RNA Targeting by the Type III-A CRISPR-Cas Csm Complex of *Thermus thermophilus*. Mol Cell 56, 518-530.

Tamulaitis, G., Kazlauskiene, M., Manakova, E., Venclovas, C., Nwokeoji, A. O., Dickman, M. J., Horvath, P., and Siksnys, V. (2014). Programmable RNA Shredding by the Type III-A CRISPR-Cas System of *Streptococcus thermophilus*. Mol Cell 56, 506-517. van der Oost, J., Westra, E. R., Jackson, R. N., and Wiedenheft, B. (2014). Unravelling the structural and mechanistic basis of CRISPR-Cas systems. Nat Rev Microbiol 12, 479-492.

Westra, E. R., van Erp, P. B., Kunne, T., Wong, S. P., Staals, R. H., Seegers, C. L., Bollen, S., Jore, M. M., Semenova, E., Severinov, K., et al. (2012). CRISPR immunity relies on the consecutive binding and degradation of negatively supercoiled invader DNA by Cascade and Cas3. Mol Cell 46, 595-605.

Zhang, J., Rouillon, C., Kerou, M., Reeks, J., Brugger, K., Graham, S., Reimann, J., Cannone, G., Liu, H., Albers, S. V., et al. (2012). Structure and Mechanism of the CMR Complex for CRISPR-Mediated Antiviral Immunity. Mol Cell 45, 303-313.

We claim:

1. A method for transcription-restricted DNA modification that modifies a DNA sequence in a chromosome of a cell, the method comprising modifying the DNA sequence in the chromosome of the cell only during transcription of said DNA sequence, and wherein the modifying comprises cutting only a non-template strand only within said DNA sequence, by expressing in the cell from a recombinant vector a clustered regularly interspaced short palindromic repeats (CRISPR) system, the CRISPR system comprising nucleotide sequences encoding: i) a CRISPR RNA (crRNA) targeted only to a DNA sequence on a coding strand of the DNA sequence that is transcribed and is operatively linked to a promoter; and CRISPR-associated enzymes (Cas) 10, Cas6, Csm2, Csm3, Csm4, Csm5 and Csm6, the method further comprising determining the DNA sequence that was transcribed and modified.

2. The method of claim 1, wherein the modification is a conditional modification of the DNA such that transcription of the DNA from the promoter is not constitutive transcription.

3. The method of claim 1, wherein the promoter is an inducible promoter.

4. The method of claim 3, further comprising inducing transcription from the inducible promoter such that the DNA modification takes place only during the induced transcription.

5. The method of claim 1, wherein the modification of the DNA sequence confers a change in phenotype of the cell.

6. The method of claim 1, wherein the modification of the DNA sequence is lethal to the cell.

7. The method of claim 1, wherein the DNA sequence encodes a selectable marker, or a detectable marker.

* * * * *